(12) United States Patent
Hoggarth et al.

(10) Patent No.: US 11,707,379 B2
(45) Date of Patent: Jul. 25, 2023

(54) OSTOMY APPLIANCE

(71) Applicant: CONVATEC LIMITED, Deeside (GB)

(72) Inventors: Marcus Hoggarth, London (GB); Oliver Poyntz, London (GB); Kimahni Emsley, London (GB); Daljinder Sanghera, London (GB); Liberty Fearns, London (GB)

(73) Assignee: ConvaTec Limited, Deeside (GB)

( * ) Notice: Subject to any disclaimer, the term of this patent is extended or adjusted under 35 U.S.C. 154(b) by 0 days.

(21) Appl. No.: 17/061,732

(22) Filed: Oct. 2, 2020

(65) Prior Publication Data
US 2021/0100678 A1 Apr. 8, 2021

Related U.S. Application Data

(63) Continuation of application No. PCT/GB2020/052416, filed on Oct. 2, 2020.
(Continued)

(30) Foreign Application Priority Data

Oct. 4, 2019 (GB) ..................... 1914351
Oct. 4, 2019 (GB) ..................... 1914363
(Continued)

(51) Int. Cl.
*A61F 5/445* (2006.01)
*A61F 5/44* (2006.01)

(52) U.S. Cl.
CPC ............ *A61F 5/445* (2013.01); *A61F 5/4404* (2013.01)

(58) Field of Classification Search
CPC ........ A61F 5/445; A61F 5/4404; A61F 5/443; A61F 13/00085; A61F 13/0259; A61F 2013/008
See application file for complete search history.

(56) References Cited

U.S. PATENT DOCUMENTS 3,902,496 A * 9/1975 Eakin ................. A61F 5/445
  604/334
5,250,042 A 10/1993 Torgalkar et al.
(Continued)

FOREIGN PATENT DOCUMENTS

DE 19752598 C1 8/1999
EP 3837520 A1 6/2021
(Continued)

OTHER PUBLICATIONS

International Search Report; European Patent Office; International Application No. PCT/GB2020/052415; dated Dec. 22, 2020; 5 pages.
(Continued)

*Primary Examiner* — Erich G Herbermann
*Assistant Examiner* — Alessandro R Del Priore
(74) *Attorney, Agent, or Firm* — Taft Stettinius & Hollister LLP; Ryan O. White; Derek B. Lavender

(57) ABSTRACT

An ostomy appliance comprising a main body portion comprising an inner wall and an outer wall of flexible sheet material joined together to define a cavity for containing a stomal output;
  the inner wall comprising an inlet for receiving the stomal output into the cavity;
  the ostomy appliance further comprising an outer comfort layer overlying at least a portion of the outer wall;
  wherein the outer comfort layer comprise a first part and a second part which are joined to the outer wall so that the first part partially overlaps the second part in an overlap region, wherein the first part and the second part are separable from each other in the overlap region to form a window opening for viewing the cavity;
(Continued)

wherein the overlap region is angled obliquely to a horizontal direction when the ostomy appliance is orientated as it would be in use.

18 Claims, 27 Drawing Sheets

Related U.S. Application Data

(60) Provisional application No. 62/911,144, filed on Oct. 4, 2019.

(30) Foreign Application Priority Data

| Oct. 4, 2019 | (GB) | 1914375 |
|---|---|---|
| Oct. 4, 2019 | (GB) | 1914379 |
| Oct. 4, 2019 | (GB) | 1914380 |

(56) References Cited

U.S. PATENT DOCUMENTS

| | | | |
|---|---|---|---|
| 6,186,989 B1 * | 2/2001 | Horie | A61F 5/449 |
| | | | 604/345 |
| 8,821,463 B2 | 9/2014 | Grum-Schwensen | |
| 11,033,418 B2 | 6/2021 | O'Brien et al. | |
| 11,076,978 B2 | 8/2021 | Nguyen-Demary et al. | |
| 11,076,979 B2 | 8/2021 | Fattman et al. | |
| 11,096,818 B2 | 8/2021 | Thirstrup et al. | |
| 11,160,681 B2 | 11/2021 | Strobech et al. | |
| 11,337,858 B2 | 5/2022 | Schwartz | |
| 2003/0014023 A1 | 1/2003 | Kanbara | |
| 2005/0159717 A1 | 7/2005 | Holtermann | |
| 2008/0300556 A1 | 12/2008 | Fenton | |
| 2011/0190718 A1 * | 8/2011 | Wheaton | A61F 5/445 |
| | | | 604/332 |
| 2012/0283678 A1 | 11/2012 | Nguyen-DeMary et al. | |
| 2013/0053802 A1 * | 2/2013 | Maidl | A61F 5/445 |
| | | | 604/332 |
| 2013/0096522 A1 * | 4/2013 | Svensby | A61F 5/445 |
| | | | 604/336 |
| 2013/0116643 A1 * | 5/2013 | Wolrich | A61F 5/445 |
| | | | 604/339 |
| 2013/0253455 A1 | 9/2013 | Masters et al. | |
| 2014/0039430 A1 * | 2/2014 | Richmann | A61F 5/443 |
| | | | 604/332 |
| 2015/0320585 A1 * | 11/2015 | Fattman | A61F 5/4407 |
| | | | 604/344 |
| 2017/0156918 A1 * | 6/2017 | Schertiger | A61F 5/448 |
| 2018/0116859 A1 * | 5/2018 | Strøbech | A61F 5/445 |
| 2018/0333290 A1 * | 11/2018 | Jones | A61F 5/441 |
| 2019/0029868 A1 | 1/2019 | Grum-Schwensen et al. | |
| 2021/0177642 A1 | 6/2021 | Andersen et al. | |
| 2021/0212855 A1 | 7/2021 | Hansen et al. | |
| 2021/0228402 A1 * | 7/2021 | Becker | A61F 5/4401 |
| 2021/0268142 A1 | 9/2021 | Lam et al. | |
| 2021/0361464 A1 | 11/2021 | Larsen et al. | |
| 2021/0361466 A1 | 11/2021 | Hansen et al. | |
| 2021/0361467 A1 | 11/2021 | Hansen et al. | |
| 2021/0369197 A1 | 12/2021 | Hansen et al. | |
| 2021/0369484 A1 | 12/2021 | Holden et al. | |
| 2021/0369485 A1 | 12/2021 | Evans | |
| 2021/0369486 A1 | 12/2021 | Holden et al. | |
| 2021/0369488 A1 | 12/2021 | Hansen et al. | |
| 2021/0369489 A1 | 12/2021 | Hansen et al. | |
| 2021/0369490 A1 | 12/2021 | Hansen et al. | |
| 2021/0369493 A1 | 12/2021 | Young et al. | |
| 2021/0369494 A1 | 12/2021 | Holden et al. | |
| 2022/0000652 A1 | 1/2022 | Thirstrup et al. | |
| 2022/0000653 A1 | 1/2022 | Granet et al. | |
| 2022/0008240 A1 | 1/2022 | Strobech et al. | |
| 2022/0079803 A1 | 3/2022 | Windeballe et al. | |
| 2022/0241104 A1 | 8/2022 | Knoedler | |
| 2022/0241105 A1 | 8/2022 | Hansen et al. | |
| 2022/0265457 A1 | 8/2022 | Emborg et al. | |

FOREIGN PATENT DOCUMENTS

| | | |
|---|---|---|
| EP | 3727240 B1 | 12/2021 |
| EP | 3729456 B1 | 12/2021 |
| EP | 3917467 A1 | 12/2021 |
| EP | 3706672 B1 | 1/2022 |
| EP | 3727234 B1 | 1/2022 |
| EP | 3454796 B1 | 2/2022 |
| EP | 3454797 B1 | 2/2022 |
| EP | 3955864 A1 | 2/2022 |
| EP | 3727231 B1 | 3/2022 |
| EP | 3727242 B1 | 3/2022 |
| EP | 3958802 A1 | 3/2022 |
| EP | 3727247 B1 | 4/2022 |
| EP | 3764956 B1 | 5/2022 |
| EP | 3989889 A1 | 5/2022 |
| EP | 3989890 A1 | 5/2022 |
| EP | 3996106 A1 | 5/2022 |
| EP | 3998051 A1 | 5/2022 |
| EP | 3727228 B1 | 6/2022 |
| EP | 4032510 A1 | 7/2022 |
| EP | 4032511 A1 | 7/2022 |
| EP | 4042985 A1 | 8/2022 |
| EP | 4042986 A1 | 8/2022 |
| EP | 4042987 A1 | 8/2022 |
| GB | 1570181 A | 6/1980 |
| GB | 2566722 B | 3/2019 |
| GB | 2566723 B | 3/2019 |
| GB | 2566724 B | 3/2019 |
| GB | 2566725 B | 3/2019 |

OTHER PUBLICATIONS

Written Opinion of the International Searching Authority; European Patent Office; International Application No. PCT/GB2020/052415; dated Dec. 22, 2020; 9 pages.

International Search Report; European Patent Office; International Application No. PCT/GB2020/052414; dated Dec. 8, 2020; 3 pages.

Written Opinion of the International Searching Authority; European Patent Office; International Application No. PCT/GB2020/052414; dated Dec. 8, 2020; 6 pages.

International Search Report; European Patent Office; International Application No. PCT/GB2020/052413; dated Dec. 10, 2020; 3 pages.

Written Opinion of the International Searching Authority; European Patent Office; International Application No. PCT/GB2020/052413; dated Dec. 10, 2020; 5 pages.

International Search Report; European Patent Office; International Application No. PCT/GB2020/052416; dated Jan. 19, 2021; 5 pages.

Written Opinion of the International Searching Authority; European Patent Office; International Application No. PCT/GB2020/052416; dated Jan. 19, 2021; 9 pages.

* cited by examiner

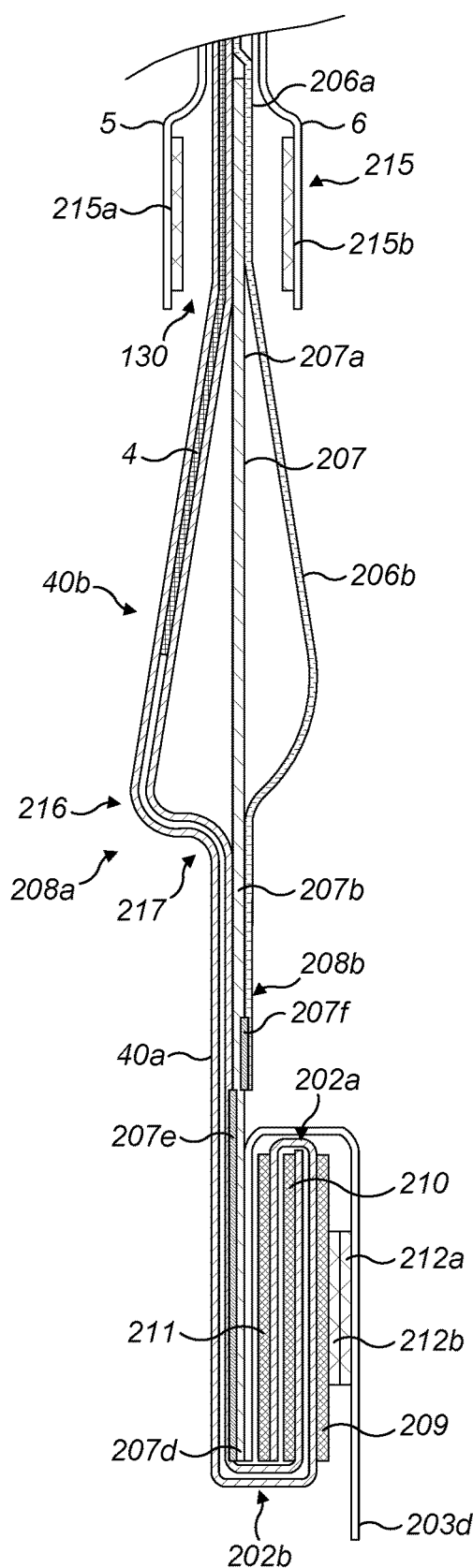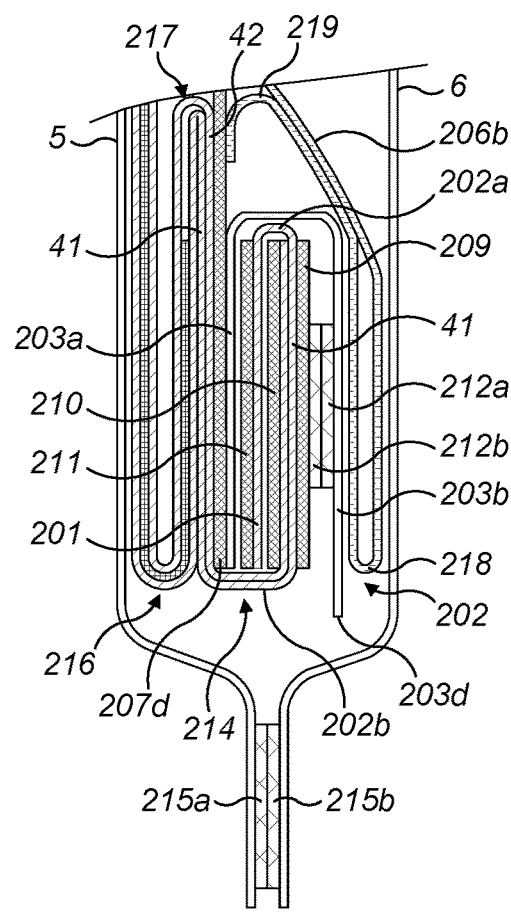
FIG. 18b
FIG. 18c

OSTOMY APPLIANCE

This application is a continuation of International Application No. PCT/GB2020/052416 filed Oct. 2, 2020 and claims the priority of foreign Application Nos. GB1914375.9, GB1914363.5, GB1914379.1, GB1914380.9, GB1914351.0, and U.S. Provisional Application No. 62/911,144, all filed Oct. 4, 2019. The disclosures of which are hereby incorporated herein in their entirety.

TECHNICAL FIELD

The present disclosure relates to an ostomy appliance for managing effluent from a stoma.

BACKGROUND OF THE DISCLOSURE

There are many forms of ostomy appliance which try to provide a secure, comfortable fit for ostomates.

US2011/190718 discloses one such ostomy appliance in the form of an ostomy pouch which comprises a proximal and a distal side wall of flexible sheet material joined together along their peripheral edges to define a cavity there between. The side walls are also joined in at least one location inwardly of the peripheral edges to limit the separation of the proximal and distal side walls. With this construction, the side walls also include a laterally outwardly expandable fold which is formed by at least a portion of at least one of the side walls.

There remains a need for ostomy appliances with enhanced usability for ostomates, particularly in the areas of ease of use and discretion of use.

SUMMARY OF THE DISCLOSURE

In this specification, the term "stomal output" refers to any gases or fluids or solids produced by an ostomate that may be secreted from the stoma or that exit the stoma. The stomal output may comprise stomal gas, stomal liquid and stomal solids.

In this specification, the term "stoma" refers to an opening in the body. Generally the stoma is a surgical opening in the torso of the body. In some instances, the term "stoma" also refers to internal tissue, organs or portions thereof that are exposed by the opening. By way of non-limiting example, internal tissue may be selected from colon, ileum, small intestine, large intestine, jejunum, and duodenum, and combinations thereof. The internal tissue may be an end or a loop of a small or large intestine.

In this specification, the term "ostomate" refers to a subject that may have use of the ostomy appliance disclosed herein. While ostomate usually refers to a subject with a surgical opening, as used herein, "ostomate" may refer to a subject who has a stoma, regardless of whether the stoma was created by surgery or other means.

The term "user" may refer to an ostomate, or to another person assisting the ostomate, for example, with emptying of the stomal output from the cavity.

In this specification, the ostomy appliances disclosed herein may, for example, be used for managing a stoma created by an esophagostomy, a gastrostomy, a cholecystostomy, a choledochostomy, a cecostomy, a colostomy, a duodenostomy, an ileostomy, a jejunostomy, an appendicostomy, a tracheostomy, a urostomy, a nephrostomy, an ureterostomy, or a vesicostomy. The ostomy appliances disclosed herein may be used with additional devices including, but not limited to, a shunt, a catheter, a plug or a fecal management system.

Beneficially, the ostomy appliances of the present disclosure may permit an ostomate to increase the period of use of each ostomy appliance compared to prior art appliances. This may be achieved, for example, by providing an increased cavity volume for the ostomy appliance while maintaining ostomate discretion and comfort. Additionally or alternatively, this may also be achieved by providing means for draining the cavity of stomal output reliably and hygienically so as to increase an ostomate's confidence in reusing to ostomy appliance compared to some prior art appliances. Since the ostomate may be inclined to use each ostomy appliance of the present disclosure for longer, the total number of ostomy appliances used by the ostomate in a given time period may be reduced. This may produce an environmental benefit in reducing the amount of environmental waste produced.

In this specification locations and orientations of features may be described with reference to the ostomy appliance being "in use", "orientated as it would be in use" or similar. Such terms refer to the intended orientation of the ostomy appliance when it is adhered to a body of an ostomate with the ostomate in a standing position, irrespective of whether the ostomy appliance is currently performing such a use or the actual position of the ostomate. The terms "upper" and "lower" and related terms refer to the relative position of a part or portion of the ostomy appliance when orientated as it would be in use. For example, an apex of the ostomy appliance may be referred to as an "upper" apex in use of the ostomy appliance. In such an example, said apex will be intended to be the uppermost apex (in the vertical direction) of the ostomy appliance when attached to the body of a standing ostomate. However the reader skilled in the art will appreciate that before attachment to the ostomate said apex may not always be the uppermost apex and in addition when attached the apex may not always be the uppermost apex if the ostomate adopts a non-standing position, for example lying down.

In this specification the terms "inner" and "outer" refer to the relative position of a part or portion of the ostomy appliance with reference to the body of an ostomate when the ostomy appliance is attached to the body. "Inner" refers to a position relatively closer to the body of the ostomate than a comparative position that is "outer". "Outer" refers to a position relatively further away from the body of the ostomate than a comparative position that is "inner".

In this specification the term "peripheral region" refers to a portion situated on or towards an edge of the item being referred to.

The term "turned up" used herein may include folding or rolling of the components.

The present disclosure provides an ostomy appliance comprising an inner wall and an outer wall of flexible sheet material joined together to define a cavity for containing a stomal output;
  the inner wall comprising an inlet for receiving the stomal output into the cavity;
  at least one peripheral region of the inner wall and the outer wall being foldable inwardly in a first rotational direction into a folded configuration to overlie at least one adjacent region of the inner wall and the outer wall such that the cavity has a first useable volume;
  the at least one peripheral region being unfoldable outwardly in a second rotational direction into an unfolded configuration to uncover the at least one adjacent region such that the cavity has a second useable volume that is greater than the first useable volume;

the ostomy appliance further comprising at least one comfort layer overlying at least one of the inner wall and the outer wall, the at least one comfort layer comprising one or more openings configured to receive a portion of the at least one peripheral region and to releasably retain the at least one peripheral region in its folded configuration.

The ostomy appliance of the present disclosure may beneficially be used discreetly since it may be initially folded into a folded configuration having the first useable volume when first used. The reduced size and footprint of the ostomy appliance in the folded configuration may make it easier for the ostomy appliance to be hidden under the clothing of the ostomate. Further, the reduced size and footprint make increase the ease of movement of the ostomate, for example bending over, turning, or rolling over. The ability of the ostomy appliance to adopt the folded configuration and unfolded configuration may increase the flexibility of use of the ostomy appliance. For example the ostomy appliance may be used with smaller and larger volumes of stomal output. Beneficially an initial reduced size and footprint for the ostomy appliance may be obtained in the folded configuration without reducing the total volume of stomal output that can be contained in the unfolded configuration.

Configuring the at least one peripheral region to move between the folded configuration and the unfolded configuration by folding inwardly in the first rotational direction and folding outwardly in the second rotational direction may beneficially increase the ease of use of the ostomy appliance. The movement required may be simple for the ostomate to achieve without requiring any enhanced degree of manual dexterity.

When the inner wall and the outer wall are folded into the folded configuration they are both folded in the same rotational sense. The first rotational direction and the second rotational direction may be in opposite senses to each other.

The ostomy appliance may be supplied to the ostomate in the folded or unfolded configuration. Preferably the ostomy appliance is supplied in the folded configuration as this may have the benefit of reducing the size and volume of the packaging of the ostomy appliance. The ostomy appliance may be moved between folded and unfolded configurations one or multiple times during the useable life of the ostomy appliance.

Beneficially, the provision of the one or more openings in the at least one comfort layer may provide a simple means for retaining the at least one peripheral region in its folded configuration. As above, this means of retention may be simple for the ostomate to achieve without requiring any enhanced degree of manual dexterity. For example, the use of the one or more openings may avoid the need for fastening or unfastening a clip, button, stud or snap fastening which may be difficult for the ostomate to achieve if they have limited manually dexterity. This problem may be exacerbated in the typical scenario where the ostomy appliance is located on the torso of the ostomate which may make seeing and reaching portions of the ostomy appliance more difficult.

A further benefit of the use of the one or more openings in the at least one comfort layer is that it may avoid the need for a fastening mechanism that comprises a substantial protuberance on the surface of the ostomy appliance. Such a protuberance might be produced, for example, by the addition of an element such as a clip, button, stud or snap fastening, or the addition of one or more elements, such as patches of hook and loop fastening material. Avoiding the use of such protuberances may produce an ostomy appliance that is thinner and easier to conceal beneath the clothing of the ostomate. Further, the lack of such protuberances may increase the comfort of use of the ostomy appliance by reducing or eliminating protruding or rough elements that may dig in to the skin of the ostomate or cause friction against the skin. For example, the use of a snap fastening or patches of hook and loop fastening may lead to discomfort against the skin of the ostomate.

The present disclosure also provides an ostomy appliance comprising a main body portion comprising an inner wall and an outer wall of flexible sheet material joined together to define a cavity for containing a stomal output;

the inner wall comprising an inlet for receiving the stomal output into the cavity;

at least one peripheral region of the main body portion being configured to be foldable inwardly into a folded configuration to overlie at least one adjacent region of the main body portion such that the cavity has a first useable volume;

the at least one peripheral region being unfoldable outwardly into an unfolded configuration to uncover the at least one adjacent region such that the cavity has a second useable volume that is greater than the first useable volume;

wherein the main body portion of the ostomy appliance comprises, when the at least one peripheral region is in the unfolded configuration and the ostomy appliance is orientated as it would be in use, an upper apex pointing upwards, a first lateral apex pointing to a first side, a second lateral apex pointing to a second side opposite to the first side, and a lower apex pointing downwards;

the ostomy appliance further comprising either an ostomy wafer that is located in register with the inlet of the inner wall, or a releasable coupling that is located in register with the inlet of the inner wall and that is configured for coupling with a body fitment component comprising an ostomy wafer.

In some embodiments the ostomy appliance further comprises at least one comfort layer overlying at least one of the inner wall and the outer wall, wherein the at least one comfort layer is shaped and sized to be in register with the main body portion.

Additionally or alternatively, in some embodiments the ostomy wafer or releasable coupling may be located fully within a footprint of the main body portion when the at least one peripheral region is in both the folded configuration and the unfolded configuration such that the ostomy wafer or releasable coupling is hidden from view in use of the ostomy appliance.

Additionally or alternatively, in some embodiments the outer comfort layer comprises a first part and a second part which may be joined to the outer wall so that the first part partially overlaps the second part in an overlap region. Preferably, the first part and the second part may be separable from each other in the overlap region to form a window opening for viewing the cavity.

The present disclosure also provides an ostomy appliance comprising a main body portion comprising an inner wall and an outer wall of flexible sheet material joined together to define a cavity for containing a stomal output;

the inner wall comprising an inlet for receiving the stomal output into the cavity;

the ostomy appliance further comprising an outer comfort layer overlying at least a portion of the outer wall;

wherein the outer comfort layer comprise a first part and a second part which are joined to the outer wall so that the first part partially overlaps the second part in an overlap region, wherein the first part and the second part are separable from each other in the overlap region to form a window opening for viewing the cavity;

wherein the overlap region is angled obliquely to a horizontal direction when the ostomy appliance is orientated as it would be in use.

Additionally or alternatively, the overlap region may extend from at or near a mid-point of one edge to at or near a mid-point of an opposed edge. In an alternative the overlap region may extend horizontally when the ostomy appliance is in use.

Additionally or alternatively, in some embodiments the window opening may extend fully, or substantially fully, across a face of the outer wall.

Additionally or alternatively, in some embodiments, the main body portion of the ostomy appliance comprises, when the ostomy appliance is orientated as it would be in use, an upper apex pointing upwards, a first lateral apex pointing to a first side, a second lateral apex pointing to a second side opposite to the first side, and a lower apex pointing downwards;

wherein the main body portion comprises a first edge which extends between the upper apex and the first lateral apex, a second edge which extends between the upper apex and the second lateral apex, a third edge which extends between the lower apex and the first lateral apex, and a fourth edge which extends between the lower apex and the second lateral apex.

Additionally or alternatively, in some embodiments the first part and the second part of the outer comfort layer may be configured to slide over each other in the overlap region to accommodate expansion of the underlying outer wall.

Additionally or alternatively, in some embodiments the first part and the second part may be joined to each other at a first end and at a second end of the overlap region. Preferably the first part and the second part are welded to each other at the first end and at the second end of the overlap region, preferably as part of the peripheral weld.

Preferably, the external edges of the one or more parts of the outer comfort layer are shaped and sized to be in register with the outer wall.

Additionally or alternatively, in some embodiments the inner wall and/or the outer wall may be provided with one or more pleats which are configured to partially or fully unfold as the cavity receives the stomal output.

The present disclosure also provides an ostomy appliance comprising an inner wall and an outer wall of flexible sheet material joined together to define a cavity for containing a stomal output;

the inner wall comprising an inlet for receiving the stomal output into the cavity;

the inner wall and the outer wall defining a central region, a first lateral wing region and a second lateral wing region;

wherein the outer wall comprises one or more pleats which are configured to partially or fully unfold as the cavity receives the stomal output to promote conformation of the inner wall against a body of an ostamate wearing the ostomy appliance.

The first lateral wing region may for example comprise a first apex that is pointed in a first sideways direction when the ostomy appliance is in use.

The second lateral wing region may for example comprise a second apex that is pointed in an opposite second sideways direction when the ostomy appliance is in use;

Additionally or alternatively, where a separation wall and/or a protective panel is provided these may also be provided with pleats. Preferably at least the outer wall comprises one or more pleats.

Additionally or alternatively, in some embodiments the inner wall may be free of pleats. This may assist in promoting conformation of the inner wall.

Beneficially, the one or more pleats may promote conformation of the inner wall against a body of an ostomate wearing the ostomy appliance. The one or more pleats may be configured to partially or fully unfold as the cavity receives the stomal output to promote displacement of a first lateral wing region (e.g. apex) and a second lateral wing region (e.g. apex) of the ostomy appliance towards the body of the ostomate. In some embodiments, the first lateral wing region (e.g. apex) and the second lateral wing region (e.g. apex) may be two opposed lateral wing regions (or apexes) and the conformation of the inner wall may produce an improved conformation of the inner wall to a torso of the ostomate.

Each pleat may comprise one or more folds of the flexible sheet material of the outer wall, inner wall and/or separation wall. In some embodiments, each pleat may comprise a generally Z-shaped form having two distinct folds.

Additionally or alternatively, in some embodiments the inner wall may be free of pleats.

Additionally or alternatively, in some embodiments the one or more pleats may comprise two pleats which are preferably arranged symmetrically about a vertical midline of the outer wall.

Additionally or alternatively, in some embodiments the one or more pleats are orientated vertically when the ostomy appliance is in use.

Additionally or alternatively, in some embodiments the one or more pleats may be aligned with fold lines of the inner wall and/or the outer wall.

Additionally or alternatively, in some embodiments the ostomy appliance further comprises a separation filter for filtering gases and/or liquids from solid matter contained in the stomal output; wherein the separation filter comprises one or more pleats.

Additionally or alternatively, in some embodiments the one or more pleats of the separation filter may be aligned with, preferably underlying, the one or more pleats of the outer wall.

Additionally or alternatively, in some embodiments the one or more pleats may each be 5 to 8 mm in width.

Additionally or alternatively, in some embodiments a free edge of the inner wall and a free edge of the outer wall may be joined by a peripheral weld and the peripheral weld may comprise an enhanced weld zone in the vicinity of each of the one or more pleats. For example the enhanced weld zone may comprise a weld of increased thickness compared to the peripheral weld outside the enhanced weld zone. For example an upper end and a lower end of each of the one or more pleats may be traversed by one of the enhanced weld zones.

Additionally or alternatively, in some embodiments the outer comfort layer may be free of pleats.

In some embodiments the ostomy appliance may be configured and arranged such that the at least one peripheral region may be spontaneously unfoldable from its folded configuration when the cavity is subject to a build-up of pressure.

Beneficially, configuring the at least one peripheral region to be spontaneously unfoldable may allow the ostomy appliance to adopt its unfolded configuration without intervention from the ostomate. In this way the volume of the cavity may be increased to the second useable volume automatically when needed, for example driven by an increase in an internal pressure of the cavity when subject to input of stomal output.

The ostomy appliance may be returned to the folded configuration by manually refolding the at least one peripheral region and reinserting the portion of the at least one peripheral region into the at least one opening. For example, this may be desired where the stomal output is drained from the cavity.

Additionally or alternatively, in some embodiments the one or more openings of the at least one comfort layer may be configured to receive and to releasably retain an apex of the at least one peripheral region. Thus, the apex may form at least a part of the portion of the at least one peripheral region that is releasably retained in the one or more openings. Preferably, the apex comprises a portion of the inner wall and/or the outer wall and/or the at least one comfort layer.

Beneficially, configuring the one or more openings to receive and releasably retain an apex of the at least one peripheral region may increase the ease of use of the ostomy appliance since the apex may be easier to insert into an opening compared to a straight edge of the ostomy appliance.

Additionally or alternatively, in some embodiments the at least one peripheral region may have a substantially triangular shape with a free edge that comprises an apex directed away from the at least one adjacent region. The apex may be rounded. The radius of curvature of the apex may be about 30 mm.

Additionally or alternatively, in some embodiments the at least one peripheral region may comprise at least one lateral wing region. Additionally or alternatively, in some embodiments the at least one peripheral region may comprise at least two lateral wing regions and the at least one comfort layer may comprise at least two openings. The at least two lateral wing regions may point in opposite lateral directions. Most preferably the at least one peripheral region consists of two lateral wing regions.

Additionally or alternatively, in some embodiments the at least one peripheral region may comprise two lateral wing regions, a first lateral wing region comprising the first lateral apex and a second lateral wing region comprising the second lateral apex.

Additionally or alternatively, in some embodiments the at least one lateral wing region may be foldable about a fold line that extends in a generally vertical direction when the ostomy appliance is orientated as it would be in use.

Additionally or alternatively, the ostomy appliance may further comprise a drain extending from a first apex of a main body portion of the inner wall and the outer wall; wherein the at least two lateral wing regions may comprise at least second and third apexes of the main body portion. Thus, the drain may preferably extend from an apex of the main body portion that does not comprise one of the lateral wing regions. Most preferably, the drain may extend from a lower apex of the main body portion.

Additionally or alternatively, in some embodiments the at least one lateral wing region may each comprise an apex that is pointed sideways when the ostomy appliance is in use.

Additionally or alternatively, in some embodiments the at least one lateral wing region may be foldable about a fold line that extends in a generally vertical direction when the ostomy appliance is in use.

Beneficially, configuring the at least one peripheral region to comprise at least one lateral wing region, preferably at least two lateral wing regions, may enhance the usability of the ostomy appliance. In particular, the lateral wing region or lateral wing regions may provide a relatively flexible portion of the ostomy appliance that may conform better to the body of the ostomate, increasing discretion and comfort. For example, each lateral wing region may be triangular in shape and may be flexible so that the apex lies relatively close to the body of the ostomate even when the cavity is relatively full of stomal output.

Additionally or alternatively, in some embodiments the at least one peripheral region may comprise an upper region and/or a lower region.

Additionally or alternatively, in some embodiments the at least one peripheral region may comprises two, three or four peripheral regions.

Additionally or alternatively, in some embodiments the ostomy appliance in the unfolded configuration is quadrilateral in shape, optionally with rounded apexes. In the unfolded configuration the ostomy appliance is preferably flat. Optionally, the ostomy appliance in the unfolded configuration is square in shape, optionally with rounded apexes. The radius of curvature of the apexes may be about 30 mm.

The ostomy appliance in the unfolded configuration may have at least one dimension that is between 120 mm and 200 mm, preferably 140 mm to 160 mm, for example 145 mm. The at least one dimension may be the length and/or width dimension. Preferably, the ostomy appliance in the unfolded configuration may have at least two dimensions that are both between 120 mm and 200 mm, preferably 140 mm to 160 mm, for example 145 mm. The at least two dimensions may be the length and width dimensions.

Additionally or alternatively, in some embodiments the inner wall and the outer wall in the unfolded configuration are quadrilateral in shape, optionally with rounded apexes. Optionally, the inner wall and the outer wall in the unfolded configuration are square in shape, with four rounded apexes. The radius of curvature of the apexes may be about 30 mm. These configurations may find particular application where the ostomy appliance is a closed, non-drainable appliance.

The inner wall and the outer wall in the unfolded configuration may have at least one dimension that is 120 mm to 200 mm, preferably 140 mm to 160 mm, for example 145 mm. The at least one dimension may be the length and/or width dimension. Preferably, the inner wall and the outer wall in the unfolded configuration may have at least two dimensions that are both 120 mm to 200 mm, preferably 140 mm to 160 mm, for example 145 mm. The at least two dimensions may be the length and width dimensions.

Additionally or alternatively, in some embodiments the inner wall and the outer wall in the unfolded configuration may comprise a main body portion and an elongate drain portion that extends from the main body portion. Preferably, the elongate drain portion may extend from an apex of the main body portion. The main body portion may be a quadrilateral-shaped portion. For example, the main body portion may be a diamond-shaped portion, a rhombus-shaped portion, or a square-shaped portion. These configurations may find particular application where the ostomy appliance is an open, drainable appliance.

The main body portion in the unfolded configuration may have at least one dimension that is 120 mm to 200 mm, preferably 140 mm to 160 mm, for example 145 mm. The at least one dimension may be the length and/or width dimension. Preferably, the main body portion in the unfolded configuration may have at least two dimensions that are both 120 mm to 200 mm, preferably 140 mm to 160 mm, for example 145 mm. The at least two dimensions may be the length and width dimensions.

Additionally or alternatively, in some embodiments the ostomy appliance, or at least the main body portion thereof, when in use may comprise an upper apex which points generally vertically upwards, a lower apex which points generally vertically downwards and opposed lateral apexes which point generally to each side. Preferably, the upper apex may be joined to the opposed lateral apexes by first and second edges and the lower apex may be joined to the opposed lateral apexes by third and fourth edges.

Additionally or alternatively, the main body portion may comprise a first edge which extends between the upper apex and the first lateral apex, a second edge which extends between the upper apex and the second lateral apex, a third edge which extends between the lower apex and the first lateral apex, and a fourth edge which extends between the lower apex and the second lateral apex.

Additionally or alternatively, the first edge, the second edge, the third edge and the fourth edge may be straight.

Additionally or alternatively, the first edge may be orthogonal to the second edge and the third edge, and the second edge may be orthogonal to the first edge and the fourth edge.

Additionally or alternatively, the main body portion may be diamond-shaped, preferably rhombus-shaped.

Additionally or alternatively, in some embodiments the lower apex of the main body portion may be truncated by an intersection with a retractable drain of the ostomy appliance.

Additionally or alternatively, in some embodiments one or more of the upper apex, the lower apex and the opposed side apexes may be rounded. The radius of curvature of the apexes may be about 30 mm.

Additionally or alternatively, in some embodiments the ostomy appliance, or at least the main body portion thereof, may be configured and arranged to be foldable into a substantially hexagonal shape in the folded configuration. One or more corners of the substantially hexagonal shape may be rounded. The radius of curvature of the corners may be about 30 mm.

Additionally or alternatively, in some embodiments the inner wall and the outer wall may be formed from the same flexible sheet material or from different flexible sheet materials.

Additionally or alternatively, in some embodiments the flexible sheet material of the inner wall and/or the outer wall may comprise a single layer or a laminate of a plurality of layers.

Additionally or alternatively, in some embodiments the flexible sheet material of the inner wall and/or the outer wall may comprise polyvinylidene chloride (PVDC) and/or ethylene-vinyl acetate (EVA).

Additionally or alternatively, in some embodiments the inner wall and/or the outer wall may have a thickness of 50 to 150 micrometres, preferably 75 to 100 micrometres.

Additionally or alternatively, in some embodiments the ostomy appliance may comprise an inner comfort layer overlying the inner wall. The inner comfort layer may comprise a single part or multiple parts. Preferably the inner comfort layer comprises a single part.

Additionally or alternatively, in some embodiments the inner comfort layer may cover only a portion of the inner wall. However, preferably the inner comfort layer covers all of the inner wall (except for the inlet for receiving the stomal output into the cavity). Preferably, the inner comfort layer is shaped and sized to be in register with the inner wall.

Additionally or alternatively, in some embodiments the inner comfort layer may be provided with a wafer aperture that is in register with the inlet of the inner wall to permit fluid connection of the inlet of the inner wall to an ostomy wafer.

Additionally or alternatively, in some embodiments the ostomy appliance may comprise an outer comfort layer overlying the outer wall. The outer comfort layer may comprise a single part or multiple parts. Preferably the outer comfort layer comprises multiple parts.

Additionally or alternatively, in some embodiments the at least one comfort layer may be formed from a flexible sheet material. The material of the flexible sheet material may comprise one or more of polyester, nylon, viscose, polyurethane, polyethylene, polypropylene, polyvinylidene chloride (PVDC) and ethylene-vinyl acetate (EVA).

Additionally or alternatively, in some embodiments, the at least one comfort layer may comprise a laminate of two or more layers.

Additionally or alternatively, in some embodiments the at least one comfort layer may comprise at least one fabric layer and at least one film layer. The at least one film layer may be laminated to the at least one fabric layer, and optionally may be laminated to the at least one fabric layer over an entire area of the at least one comfort layer.

Additionally or alternatively, in some embodiments the at least one fabric layer may comprise a woven or a non-woven textile layer. The fabric layer may comprise polyester, nylon, viscose, polyethylene or polypropylene.

Additionally or alternatively, in some embodiments the at least one film layer may comprise polyurethane, polyvinylidene chloride (PVDC) or ethylene-vinyl acetate (EVA).

Additionally or alternatively, in some embodiments the at least one comfort layer may comprise a woven polyester layer. Additionally or alternatively, in some embodiments the at least one comfort layer may comprise ethylene-vinyl acetate (EVA) and/or polyvinylidene chloride (PVDC) and/or polyurethane layers.

Additionally or alternatively, in some embodiments the at least one comfort layer may have a thickness of 50 to 1000 micrometres, preferably 60 to 500 micrometres, more preferably 75 to 300 micrometres.

Additionally or alternatively, in some embodiments the ostomy appliance may comprise an inner comfort layer overlying the inner wall, and the one or more openings may be provided in the inner comfort layer; wherein, in use and in its folded configuration, the at least one peripheral region may be located between the adjacent region and a body of an ostomate wearing the ostomy appliance.

Additionally or alternatively, the one or more openings may be one or more apertures, breaks, gaps, punctures, slits, or slots in the at least one comfort layer. The one or more openings may be provided in an inner comfort layer. The one or more openings may be provided in an outer comfort layer. The one or more openings may be provided in both the inner comfort layer and the outer comfort layer.

Preferably, the one or more openings comprise one or more slits. The slits may be straight slits. The slits may pass through the full thickness of the at least one comfort layer.

In the example where the at least one comfort layer is a laminate, the slits may pass through one or more layers of the laminate.

Additionally or alternatively, in some embodiments the one or more openings may be orientated vertically when the ostomy appliance is in use. Additionally or alternatively, one or more openings may be orientated horizontally when the ostomy appliance is in use. In one example, the at least one comfort layer may comprise two openings. This may be used, for example, where the ostomy appliance comprises two lateral wing regions. Preferably, the two openings may be located symmetrically about a vertical mid-line of the ostomy appliance.

Alternatively, in another example, the at least one comfort layer may comprise three openings, with for example two openings that are orientated vertically when the ostomy appliance is in use and for example one opening that is orientated horizontally when the ostomy appliance is in use. In another example, two vertical openings and two horizontal openings may be provided.

Additionally or alternatively, in some embodiments the at least one peripheral region may comprise a stiffening member. More than one stiffening member may be provided in each at least one peripheral region.

Additionally or alternatively, in some embodiments the at least one adjacent region may comprise a stiffening member. More than one stiffening member may be provided in each at least one adjacent region.

For example, in some embodiments the at least one peripheral region and the at least one adjacent region may each comprise a stiffening member. Alternatively, the at least one peripheral region may comprise a stiffening member but the at least one adjacent region may not comprise a stiffening member. Alternatively, the at least one peripheral region may not comprise a stiffening member but the at least one adjacent region may comprise a stiffening member.

Complementary stiffening members may be provided on both the at least one peripheral region and the at least one adjacent region.

Additionally or alternatively, in some embodiments for each peripheral region, a single stiffening member may be provided that extends from the peripheral region to the respective adjacent region. However, preferably the stiffening members of the at least one peripheral region and the at least one adjacent region may be separated from one another and may comprise two parts.

Additionally or alternatively, in some embodiments the stiffening member of the at least one peripheral region and the stiffening member of the at least one adjacent region may be separated by a gap which may define the location of folding of the at least one peripheral region.

Additionally or alternatively, in some embodiments the stiffening members of the at least one peripheral region and the at least one adjacent region may be located equidistant from a fold line that extends between the at least one peripheral region and the at least one adjacent region.

Additionally or alternatively, in some embodiments the stiffening members of the at least one peripheral region and the at least one adjacent region may be aligned relative to the fold line that extends between the at least one peripheral region and the at least one adjacent region such that the stiffening members of the at least one peripheral region and the at least one adjacent region overlie each other in the folded configuration. For example, the stiffening members of the at least one peripheral region and the at least one adjacent region may be vertically and horizontally aligned with each other.

Additionally or alternatively, in some embodiments the stiffening members may be integrated in, or affixed to, the outer wall. However, preferably the stiffening members are integrated in, or affixed to, the inner wall. Additionally or alternatively, the stiffening members may be covered by the inner comfort layer. Beneficially covering the stiffening members by the inner comfort layer 5 may avoid contact between the skin of the ostomate and the stiffening members.

Additionally or alternatively, in some embodiments the stiffening member may be welded to the inner wall or adhered to the inner wall using an adhesive.

Additionally or alternatively, in some embodiments each stiffening member may have a rectangular shape. Preferably, each stiffening member may be of the same size. The stiffening members may have a length of 10 to 40 mm, a width of 10 to 30 mm and a thickness of 0.25 to 1.00 mm.

Additionally or alternatively, in some embodiments the stiffening members may comprise a planar piece of material, which may preferably be thin and which may preferably be stiffer than a material of the at least one comfort layer. In one example, the stiffening member may comprise a plate, panel or lamina of material.

Additionally or alternatively, in some embodiments the stiffening members may be formed of polystyrene, polypropylene, polyethylene, ethylene vinyl acetate (EVA), thermoplastic polyurethane (TPU) or a combination thereof.

Alternatively or additionally, in some embodiments the one or more stiffening members may comprise one or more welds in the at least one peripheral region and/or the at least one adjacent region. Alternatively or additionally, the one or more stiffening members may comprise local thickening of the flexible sheet material of the at least one peripheral region and/or the at least one adjacent region.

Alternatively or additionally, in some embodiments the one or more stiffening members may comprise a flexible hinge. The flexible hinge may be elastically movable between an unfolded and folded configuration. The flexible hinge may be biased into its folded configuration. For example the flexible hinge may be a piece of resilient polymer that is folded when unloaded. The flexible hinge may be plastically movable between an unfolded and folded configuration. For example, the flexible hinge may be a piece of aluminium foil. The flexible hinge may have bi-stable configurations—folded and unfolded.

Alternatively or additionally, in some embodiments the inner wall and/or the outer wall and/or the inner comfort layer and/or the outer comfort layer may be pre-scored to assist in defining the location of fold lines between the at least one peripheral region and the at least one adjacent region. For example, the inner wall and/or outer wall may be pre-scored.

Alternatively or additionally, in some embodiments the inner comfort layer and/or the outer comfort layer may be provided with permanent creases to help demarcate the location of the fold lines.

Additionally or alternatively, in some embodiments a central region of the at least one comfort layer may be joined to a central region of the respective inner wall or outer wall along a central contact line. Preferably, a central region of the inner comfort layer may be joined to a central region of the inner wall along a central contact line. Additionally or alternatively, in some embodiments the central contact line may be a central weld line. Additionally or alternatively, in some embodiments the central contact line may be located between two openings in the at least one comfort layer. Preferably the central contact line may be equidistant from each of the two openings.

Additionally or alternatively, in some embodiments the second useable volume of the ostomy appliance is between 350 and 600 ml. Additionally or alternatively, in some embodiments the first useable volume is between 150 and 350 ml.

Ostomy appliances are commonly attached to the body by means of an ostomy wafer which includes an adhesive layer or layers. The ostomy wafer typically has an opening for the stoma sometimes referred to as a starter hole which may be cut to a required size by a user before attachment. The ostomy wafer typically comprises an adhesive layer on a body-facing side for adhering the ostomy wafer to the body of the ostomate. Typically, a release liner covers a body-facing side of the ostomy wafer that is removed by the user prior to fitting to the skin. In this specification, the term "ostomy wafer" may be used interchangeably with the terms "adapter," "wafer," "baseplate", or "layered adhesive wafer." In this specification, the term "ostomy wafer" includes ostomy wafers for a "two-piece appliance" and for a "one-piece appliance".

In this specification a "two-piece appliance" refers to an appliance where the ostomy wafer forms part of a separate body fitment component that is attached by a releasable coupling to a pouch appliance. A two-piece appliance permits the body fitment component to be separated from the pouch appliance without damage, so that at least one of the parts continues to be functionally usable. For example, the body fitment component may remain in place on the body of the ostomate.

In this specification a "one-piece appliance" refers to an appliance where the ostomy wafer is permanently attached to the appliance, to the extent that the ostomy wafer cannot easily be separated without risk of damaging the appliance. A one-piece appliance is intended to be used as an integral unit.

Additionally or alternatively, in some embodiments the ostomy appliance further comprises an ostomy wafer that is located in register with the inlet of the inner wall, or a releasable coupling that is located in register with the inlet of the inner wall and that is configured for coupling with a body fitment component comprising an ostomy wafer. Additionally or alternatively, in some embodiments the ostomy wafer may be configured for a one-piece appliance or a two-piece appliance. Additionally or alternatively, in some embodiments the ostomy wafer may extend through the wafer aperture of the inner comfort layer.

Additionally or alternatively, in some embodiments the ostomy wafer may be located at least partially in an upper peripheral region of the ostomy appliance.

Additionally or alternatively, in some embodiments the ostomy wafer or releasable coupling (in the case of a two-piece appliance) may be located fully within a periphery of the ostomy appliance or main body portion thereof when the at least one peripheral region is in both the folded configuration and the unfolded configuration such that the ostomy wafer or releasable coupling is hidden from view in use of the ostomy appliance. Beneficially this may increase the discretion of use of the ostomy appliance by hiding from view the ostomy wafer and/or releasable coupling. In this way only the material of the outer comfort layer is preferably visible in both the folded and unfolded configurations.

Ostomy appliances are commonly configured as closed appliances or open appliances. In this specification a "closed appliance" refers to an appliance where it is not intended that stomal output is drained from the cavity. Thus, a closed appliance may typically be configured as a one-use, disposable and non-reusable appliance. In this specification an "open appliance" refers to an appliance where it is intended that stomal output is drained from the cavity. Thus, an open appliance may be configured as a reusable appliance, such that it can be reused and emptied multiple times whilst attached to the body, although this is not essential. In an open appliance the stomal output may be drained intermittently as instigated by an action of the ostomate or may be drained intermittently or continuously due to the cavity being fluidly connected to a drain, for example a night drain line.

Additionally or alternatively, in some embodiments the cavity of the ostomy appliance may be configured with or without a drain. Thus, the ostomy appliance may be configured as an open or a closed appliance. The ostomy appliance may comprise at least a main body portion comprised of at least a part of the inner wall and the outer wall. Where the ostomy appliance is an open appliance the drain may be additional to the main body portion and may preferably extend from the main body portion.

Additionally or alternatively, in some embodiments where the ostomy appliance is an open appliance the appliance may comprise a retractable drain. Preferably the retractable drain may be movable between a retracted position for storage and an extended position for draining stomal output from the cavity. Additionally or alternatively, in some embodiments the retractable drain may comprise the elongate drain portion that extends from the quadrilateral-shaped portion as described above.

Additionally or alternatively, in some embodiments the ostomy appliance is quadrilateral in shape, optionally with rounded apexes, when the at least one peripheral region is in the unfolded configuration and the retractable drain is in the retracted configuration.

Additionally or alternatively, the retractable drain may be located fully within a footprint of the main body portion when in the retracted configuration.

Preferably, in the retracted position the retractable drain may be accommodated within the periphery of the inner wall and/or outer wall and/or the one or more comfort layers.

Additionally or alternatively, in some embodiments the retractable drain may be accommodated within a void space between the inner wall and the inner comfort layer or between the outer wall and the outer comfort layer.

Additionally or alternatively, the retractable drain in the extended configuration may extend downwards from the lower apex.

Additionally or alternatively, in some embodiments the inner wall and the outer wall may be joined together around a part or the whole of their peripheral edges. Joining the inner wall and the outer wall of flexible sheet material together defines the cavity for containing the stomal output. In this specification, "defines the cavity" means that the shape and/or dimensions and/or the volume of the cavity are at least partially determined by the joining of the inner wall and the outer wall of flexible material. However, it is not essential that said joining provides a fluid-tight seal around a full perimeter of the cavity. As the reader skilled in the art will appreciate, when the ostomy appliance is an open appliance at least one opening from the cavity to the drain will be provided.

The joining may be by use of welding, adhesive or equivalent means. In the case of a closed appliance the peripheral join, for example a peripheral weld, may extend around a full perimeter of the inner wall and the outer wall to create a fluid-tight seal there between. Alternatively, in the case of an open appliance the peripheral join, for example a peripheral weld, may have one or more breaks that may demarcate drainage locations from the cavity.

Additionally or alternatively, in some embodiments the inner wall and the inner comfort layer may be joined together around their peripheral edges and/or the outer wall and the outer comfort layer may be joined together around their peripheral edges. The joining may be by use of welding, adhesive or equivalent means. A single joining operation may be used to join the inner comfort layer, the inner wall, the outer wall and the outer comfort layer together. For example a single weld may be used to join the four layers.

Additionally or alternatively, in some embodiments the inner comfort layer and/or the outer comfort layer may comprise a drainage aperture. The drainage aperture may comprise a gap in a peripheral weld with the inner wall and/or outer wall. Preferably, the drainage aperture is located at a lower apex.

Additionally or alternatively, in some embodiments the cavity may be a single volume or may be sub-divided into two or more volumes. For example, the two or more volumes may be separated by partitions, wall members, filter elements, etc.

Additionally or alternatively, in some embodiments the cavity may be provided with a gas vent for venting of stomal gases from the cavity.

Additionally or alternatively, in some embodiments the ostomy appliance may be provided with an odour filter for reducing the release of unwanted odours from the cavity.

Additionally or alternatively, in some embodiments the ostomy appliance may comprise a separation wall for filtering gases and/or liquids from solid matter contained in the stomal output.

For example, the inner wall may comprise a stomal inlet and the outer wall comprise a gas vent; and the separation wall may be provided between the inner and outer walls forming separate first and second chambers and comprising a liquid and gas permeable separation filter; wherein, in use: the first chamber is arranged to receive stomal output directed into the ostomy appliance via the stomal inlet; the separation filter is arranged to communicate, from the stomal output in the first chamber, stomal liquid and stomal gas to the second chamber; and the gas vent is arranged to allow the stomal gas to migrate from the second chamber to outside of the ostomy appliance.

In another example, the inner wall may comprise a stomal inlet for receiving stomal output and the outer wall may comprise a gas vent; the separation wall may comprise a liquid and gas permeable separation filter; and the ostomy appliance comprises a stomal output flow path for directing stomal output from the stomal inlet to the first chamber, a liquid flow path for directing stomal liquid from the stomal output in the first chamber to the second chamber via the separation filter and a gas flow path for stomal gas to migrate from the stomal output in the first chamber to the gas vent via the separation filter and second chamber.

In use stomal output may be received through the stomal inlet and communicated to the first chamber. The separation filter may filter stomal gas and stomal liquid from the stomal output and communicate the stomal gas and stomal liquid to the second chamber. The gas vent may release the stomal gas from the second chamber.

Additionally or alternatively, in some embodiments the ostomy appliance may comprise a deflector panel for guiding an inflow of the stomal output as it enters the cavity through the inlet.

Additionally or alternatively, in some embodiments the ostomy appliance comprises: a protective structure within the cavity comprising a protective panel attached to the at least one wall and forming a protective chamber around the gas vent, a protective chamber gas inlet for allowing the stomal gas to migrate into the protective chamber and a protective chamber liquid outlet for allowing the stomal liquid to migrate out of the protective chamber.

In use, stomal output comprising stomal liquid and stomal gas may be received in the cavity through the stomal inlet. The stomal gas may be communicated from the rest of the cavity into the protective chamber via the protective chamber gas inlet and may be communicated from the protective chamber to outside of the ostomy appliance via the gas vent. Stomal liquid may be communicated from the rest of the cavity into the protective chamber via the protective chamber gas inlet and/or the protective chamber liquid outlet and may be communicated out of the protective chamber via the protective chamber liquid outlet.

Additionally or alternatively, in some embodiments the ostomy appliance comprises a combination of the separation wall and the protective structure. Thus an ostomy appliance comprising a separation wall in accordance with the present disclosure may further comprise a protective structure located within the second chamber and comprising a protective panel attached to the outer wall and forming a protective chamber around the gas vent. In an addition, in an ostomy appliance comprising a protective structure in accordance with the present disclosure the at least one wall may comprise at least the outer wall and separation wall, preferably also the inner wall. The separation wall may divide the cavity, preferably formed between the inner and outer walls, into separate first and second chambers. The separation wall may comprise the liquid and gas permeable separation filter.

The present disclosure also provides a method of collecting stomal discharge in an ostomy appliance comprising use of an ostomy appliance as described herein. In one embodiment the method comprises attaching an ostomy wafer of a one-piece appliance as described herein over the stoma. In another embodiment the method comprises attaching an ostomy wafer of a body fitment component of a two-piece appliance as described herein over the stoma; and attaching a pouch appliance as described herein to the body fitment component. The pouch appliance may be attached to the body fitment component before or after the ostomy wafer has been attached over the stoma.

BRIEF DESCRIPTION OF THE DRAWINGS

One or more embodiments of the disclosure will now be described, by way of example only, with reference to the accompanying drawings in which:

FIGS. 18a to 18c schematically illustrate a cross-section of the ostomy appliance of FIG. 10 with the retractable drain in a) the extended configuration b) the extended configuration with the closure portion folded and fastened and c) a partial view in the retracted configuration;

DETAILED DESCRIPTION OF THE DISCLOSURE

Figure 1:
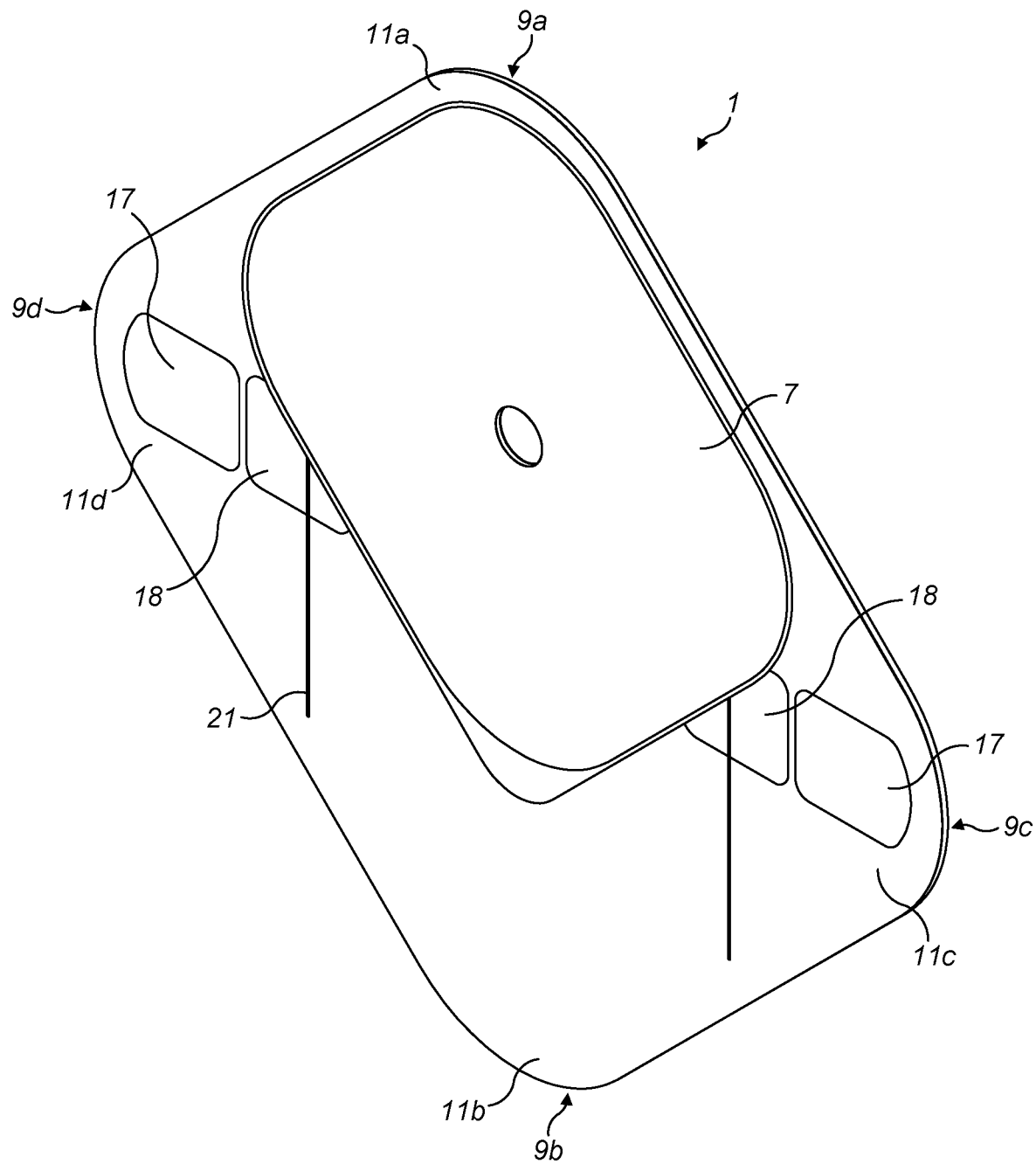
FIG. 1 illustrates a perspective view of an embodiment of ostomy appliance according to the present disclosure.

In the following description, the equivalent reference numerals are used in different embodiments to denote equivalent or similar features.

Unless defined otherwise, all technical and scientific terms used in this specification have the same meaning as is commonly understood by the reader skilled in the art to which the claimed subject matter belongs. It is to be understood that the foregoing summary of the disclosure and the following examples are exemplary and explanatory only and are not restrictive of any subject matter claimed.

The following description is directed to embodiments of the disclosure. The description of the embodiments is not meant to include all the possible embodiments of the disclosure that are claimed in the appended claims. Many modifications, improvements and equivalents which are not explicitly recited in the following embodiments may fall within the scope of the appended claims. Features described as part of one embodiment may be combined with features of one or more other embodiments unless the context clearly requires otherwise.

In this specification, the use of the singular includes the plural unless the context clearly dictates otherwise. In this application, the use of "or" means "and/or" unless stated otherwise. Furthermore, use of the term "including" as well as other forms, such as "include", "includes," and "included," is not limiting.

As used herein, ranges and amounts can be expressed as "about" a particular value or range. About also includes the exact amount. For example, "about 5 mm" means "about 5 mm" and also "5 mm." Generally, the term "about" includes an amount that would be expected to be within experimental error. The term "about" includes values that are within 10% less to 10% greater of the value provided. For example, "about 50%" means "between 45% and 55%." Also, by way of example, "about 30" means "between 27 and 33."

Figure 2:
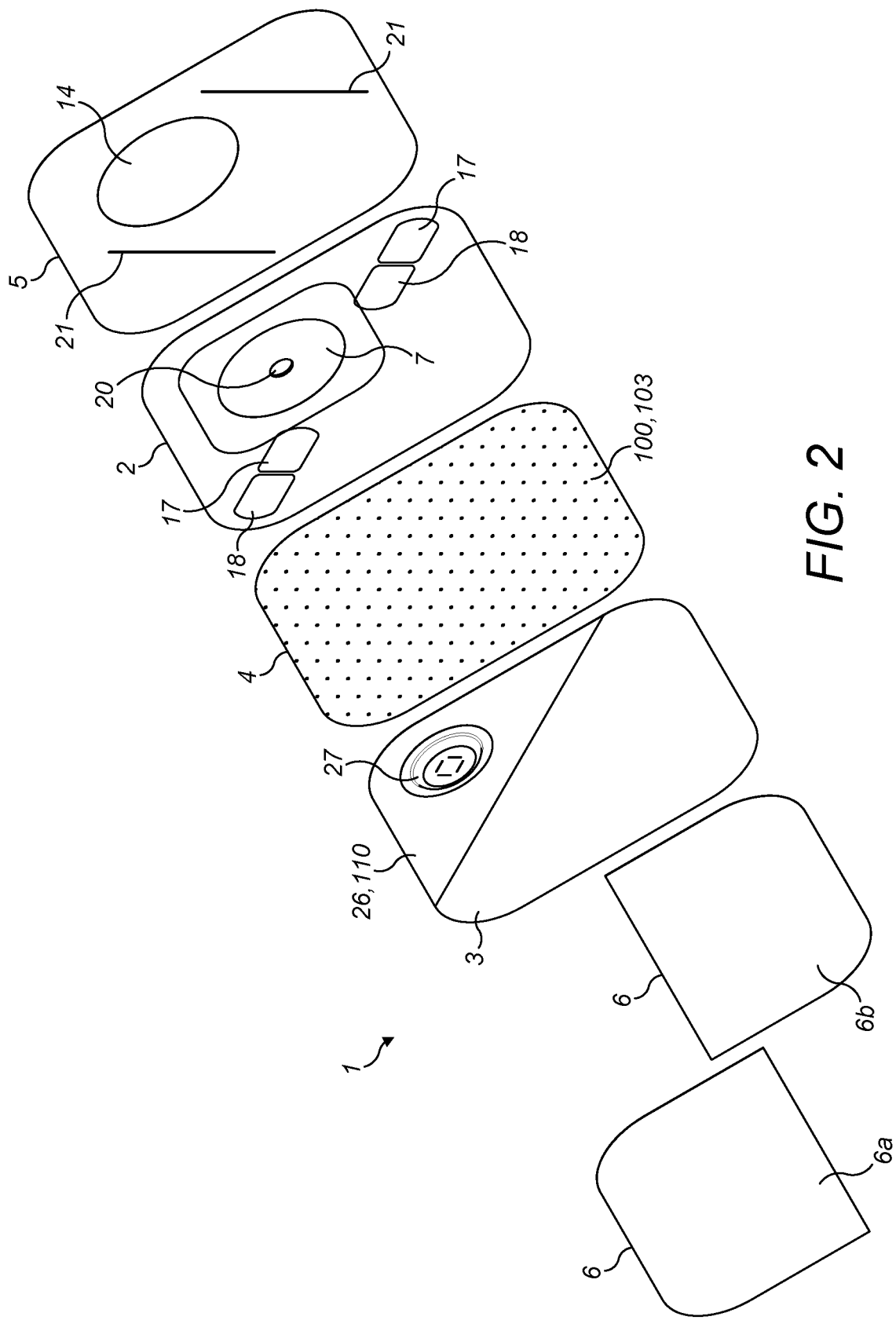
FIG. 2 illustrates an exploded perspective view of components of the ostomy appliance of FIG. 1.

A first example embodiment of an ostomy appliance 1 according to the present disclosure is shown in FIGS. 1 to 6. This example is a closed appliance. As shown in FIGS. 1 and 2, the ostomy appliance 1 may generally comprise an inner wall 2, an outer wall 3, a separation wall 4, an inner comfort layer 5, an outer comfort layer 6 and an ostomy wafer 7. The ostomy appliance 1 of this example is a one-piece appliance wherein the ostomy wafer 7 is permanently attached to the ostomy appliance 1, to the extent that the ostomy wafer 7 cannot easily be separated without risk of damaging the ostomy appliance 1. However, the teachings of this disclosure may also be applied, with suitable alteration where necessary, to two-piece appliance. For example, where the ostomy appliance 1 is a two-piece appliance the inner wall 2, the outer wall 3, the separation wall 4, the inner comfort layer 5 and the outer comfort layer 6 may together form a pouch appliance that in use may be coupled to a body fitment component that comprises the ostomy wafer 7.

The inner wall 2 and the outer wall 3 are joined together to define a cavity for containing a stomal output. The inner wall 2 and the outer wall 3 are of flexible sheet material.

Figure 3:
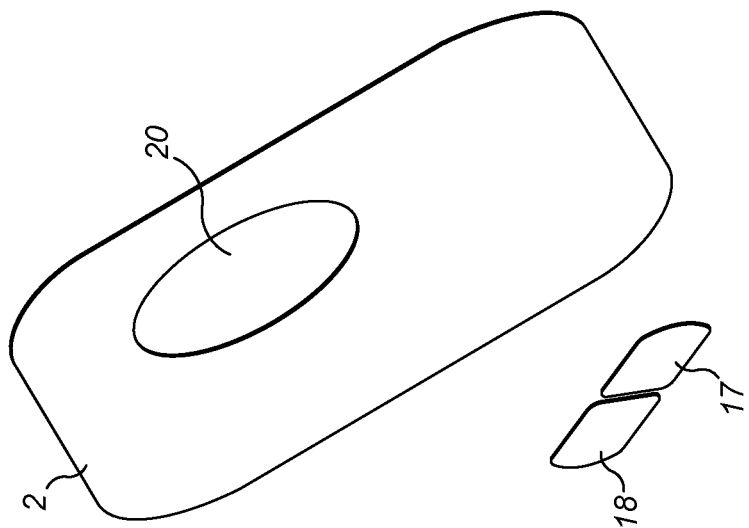
FIG. 3 illustrates an exploded perspective view of some of the components of the ostomy appliance of FIG. 1.
Figure 3:
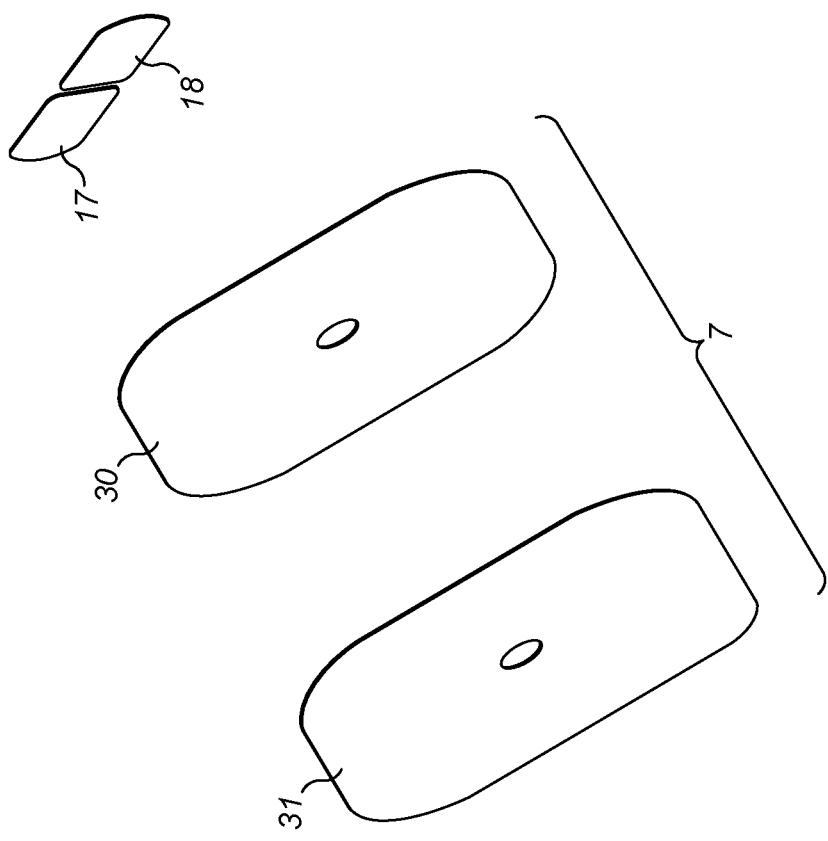

As shown in FIGS. 2 and 3, the inner wall 2 is provided with a stomal inlet 20 for receiving the stomal output into the cavity. The stomal inlet 20 may be an aperture that is cut out of the inner wall 2.

Figure 5:
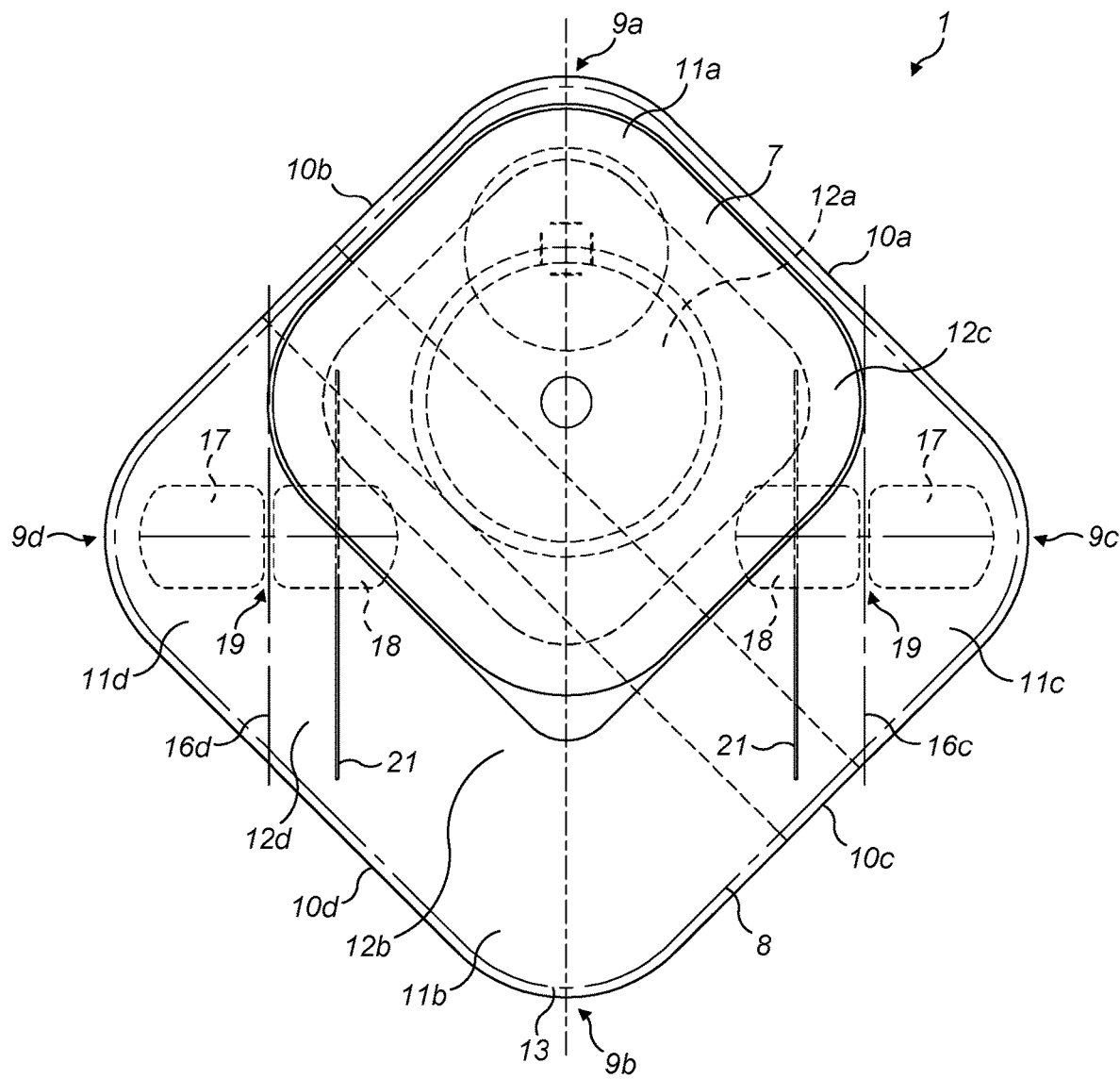
FIG. 5 is a schematic rear view of the ostomy appliance of FIG. 1.
Figure 6:
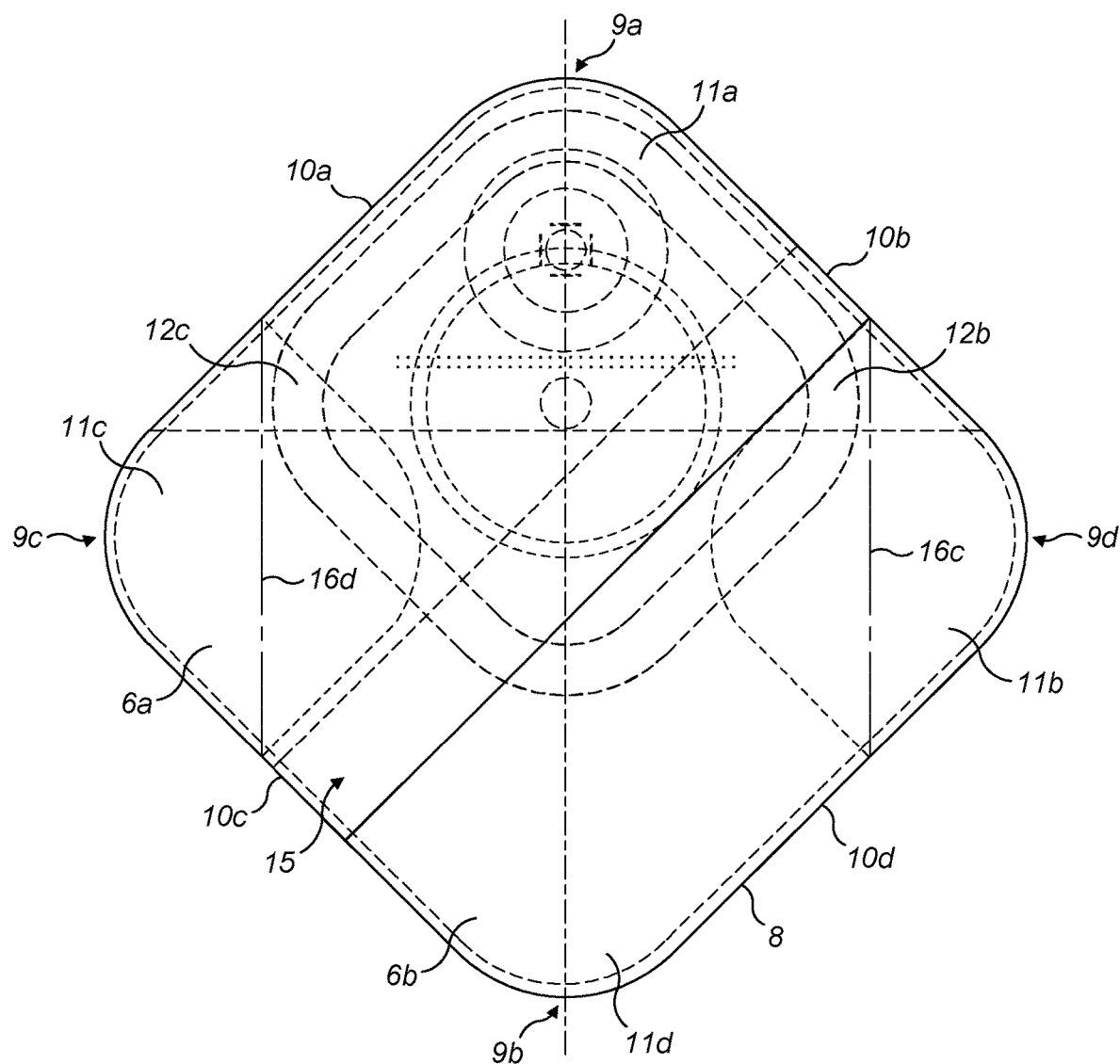
FIG. 6 is a schematic front view of the ostomy appliance of FIG. 1.

The inner wall 2 and outer wall 3 may be joined together around their peripheral edges by use of welding, adhesive or equivalent means. Welding is a preferred method of joining the inner wall 2 and the outer wall 3. As shown in FIGS. 5 and 6, a peripheral weld 8 may extend around a full perimeter of the inner wall 2 and the outer wall 3 to create a fluid-tight seal there between. The peripheral weld 8 may have a width of 1 to 3 mm, preferably about 2 mm.

In the illustrated example of FIG. 2, the inner comfort layer 5 overlies the inner wall 2 and the outer comfort layer 6 overlies the outer wall 3.

The inner comfort layer 5 and the outer comfort layer 6 may be formed of a flexible sheet material. The flexible sheet material may comprise a fabric layer. The fabric layer may be a textile layer. The textile layer may be a woven or a non-woven textile layer. Examples of suitable materials include one or more of polyester, nylon, viscose, polyethylene and polypropylene.

The inner comfort layer 5 and the outer comfort layer 6 may comprise at least one fabric layer and at least one film layer. The at least one fabric layer may comprise a non-woven textile layer but is preferably a woven textile layer. The woven textile layer may comprise one or more of polyester, nylon, viscose, polyethylene and polypropylene. The film layer may comprise one or more of polyurethane, polyethylene (PE), polyvinylidene chloride (PVDC) and ethylene-vinyl acetate (EVA). The at least one film layer may be laminated to the at least one fabric layer, and optionally may be laminated to the at least one fabric layer over an entire area of the inner comfort layer 5 and the outer comfort layer 6.

The inner comfort layer 5 may overlie the inner wall 2. The inner comfort layer 5 may cover only a portion of the inner wall 2. However, it is preferred that the inner comfort layer 5 covers all of the inner wall 2 (except for the stomal inlet 20 of the inner wall 2).

The inner wall 2 and the inner comfort layer 5 may be joined together around their peripheral edges by use of welding, adhesive or equivalent means.

As shown in FIG. 5, a peripheral weld may extend around the perimeter of the inner wall 2 and the inner comfort layer 5. The peripheral weld that joins the inner wall 2 with the inner comfort layer 5 may be the whole or a portion of the peripheral weld 8 that joins the inner wall 2 and the outer wall 3. Optionally, the inner comfort layer 5 may comprise a drainage aperture 13. The drainage aperture 13 may comprise a gap in the peripheral weld. Preferably, the drainage aperture 13 is located at the lower apex 9b.

As shown in FIG. 2, the inner comfort layer 5 is preferably provided with a wafer aperture 14 that is in register with the stomal inlet 20 of the inner wall 2.

The outer comfort layer 6 overlies at least a portion of the outer wall 3. The outer wall 3 and the outer comfort layer 6 may be joined together around their peripheral edges by use of welding, adhesive or equivalent means. A peripheral weld may extend around the perimeter of the outer wall 3 and the outer comfort layer 6. The peripheral weld that joins the outer wall 3 with the outer comfort layer 6 may be the whole or a portion of the peripheral weld 8 that joins the inner wall 2 and the outer wall 3.

In some embodiments, the peripheral weld 8 may be one weld that joins together the inner comfort layer 5, the inner wall 2, the outer wall 3 and the outer comfort layer 6.

The inner wall 2 and the outer wall 3 may be quadrilateral in shape when in an unfolded configuration as show in FIGS. 5 and 6. Preferably, the inner comfort layer 5 and the outer comfort layer 6 are also quadrilateral in shape when in an unfolded configuration as show in FIGS. 5 and 6. Preferably, in the unfolded configuration the inner wall 2 and the outer wall 3 are flat or substantially flat. The figures illustrate a preferred example wherein the inner wall 2, the outer wall 3, the inner comfort layer 5 and the outer comfort layer 6 are square in shape in the unfolded configuration. The inner wall 2 and outer wall 3 may have a length of 120 mm to 200 mm, preferably 140 mm to 160 mm, for example 145 mm. The inner wall 2 and outer wall 3 may have a width of 120 mm to 200 mm, preferably 140 mm to 160 mm, for example 145 mm. The inner comfort layer 5 and the outer comfort layer 6 may have the same external shape and dimensions as the inner wall 2 and the outer wall 3 so that the inner wall 2 and the outer wall 3 are preferably covered up to their edges.

The inner wall 2 and the outer wall 3 may have one or more rounded apexes 9. All of the apexes 9 may be rounded. It is preferred that the inner wall 2 and the outer wall 3 have four rounded apexes 9. The radius of curvature of each rounded apex 9 may be about 30 mm.

When in use (i.e. when worn by an ostomate) the inner and outer walls 2, 3 may comprise an upper apex 9a which points generally vertically upwards, a lower apex 9b which points generally vertically downwards and opposed lateral apexes 9c, 9d which point generally to each side, as shown by way of example in FIG. 5. The upper apex 9a may be joined to the opposed lateral apexes 9c, 9d by first and second edges 10a, 10b and the lower apex 9b may be joined to the opposed lateral apexes 9c, 9d by third and fourth edges 10c, 10d. In this configuration the inner wall 2 and the outer wall 3 may be considered to be 'diamond-shaped'. One or more of the upper apex 9a, the lower apex 9b and the opposed lateral apexes 9c, 9d may be rounded, for example as described above.

One or more of the first, second, third and fourth edges 10a-d may be straight, i.e. the edge 10a-d may be straight from a first apex at one end of the edge to a second apex at an opposite end of the edge. Where the apex 9 is rounded, the edge 10a-d may be straight between the rounded apex (es) 9.

The outer comfort layer 6 may comprise multiple parts. The external shape and dimensions of the multiple parts when taken together may be the same as that of the outer wall 3. For example, the outer comfort layer 6 may comprise a first part 6a and a second part 6b which may be joined to the outer wall 3 so that the first part 6a partially overlaps the second part 6b in an overlap region 15 as shown in FIG. 6. The first part 6a and the second part 6b may be separable from each other in the overlap region 15 to form a window opening for viewing the cavity. The overlap region 15 may extend obliquely from at or near a mid-point of the first edge 10a to at or near a mid-point of the fourth edge 10d. Alternatively, the overlap region 15 may extend obliquely from at or near a mid-point of the second edge 10b to at or near a mid-point of the third edge 10c. In another alternative the overlap region 15 may extend horizontally when the ostomy appliance 1 is in use.

According to the present disclosure, as shown in FIGS. 5 and 6, the inner wall 2 and the outer wall 3 comprise at least one peripheral region 11a-d which may be configured to be folded in use between a folded configuration and an unfolded configuration. The inner wall 2 and the outer wall 3 may comprise more than one peripheral region 11, for example, two, three or four peripheral regions 11a-d.

The at least one peripheral region 11a-d may have a substantially triangular shape with a free edge that comprises the apex 9. The upper apex 9a may be in an upper peripheral region 11a, the lower apex 9b may be in a lower peripheral region 11b and the opposed lateral apexes 9c, 9d may be in left and right peripheral regions 11d, 11c as shown in FIG. 5.

Figure 7:
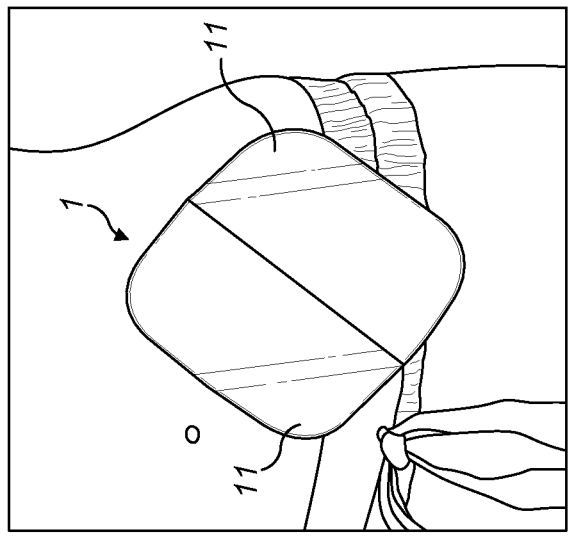
FIG. 7 is a series of views illustrating use of an ostomy appliance according to the present disclosure.
Figure 7:
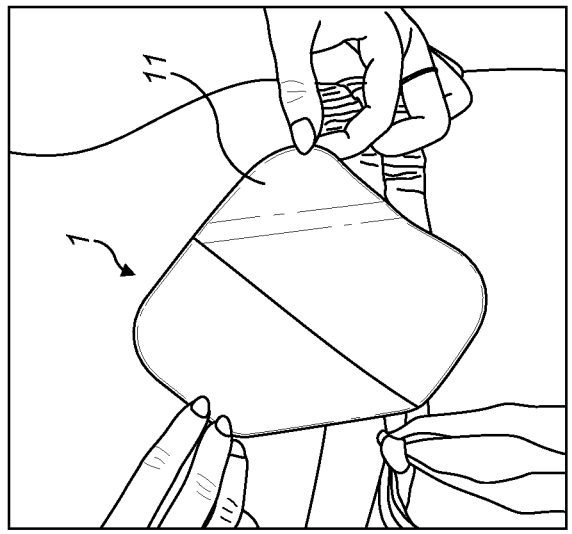
Figure 7:
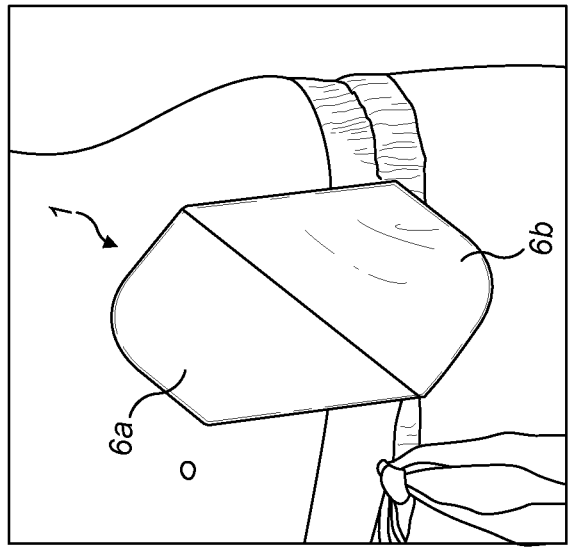
Figure 8:
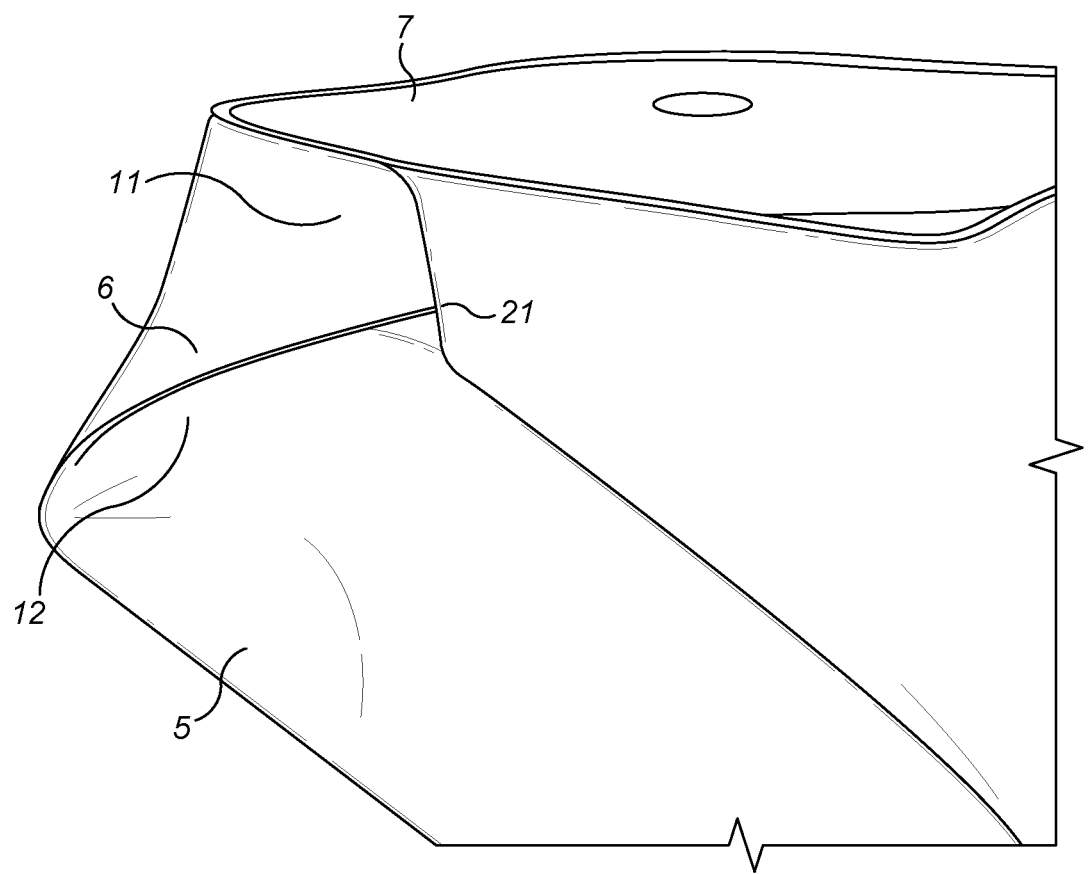
FIG. 8 is a close up perspective view of a part of an ostomy appliance according to the present disclosure.

The at least one peripheral region 11a-d may comprise at least one lateral wing region and preferably comprises at least two lateral wing regions 11c, 11d, for example being the left and right peripheral regions 11d, 11c. The at least one lateral wing region 11c, 11d may each comprise an apex 9c, 9d that is pointed sideways when the ostomy appliance 1 is in use as shown in FIG. 7.

According to the present disclosure the inner wall 2 and the outer wall 3 comprise at least one adjacent region 12a-d. Each of the peripheral regions 11a-d may be located next to an adjacent region 12a-d. A dedicated adjacent region 12a-d may be provided for each peripheral region 11*a-d*. Alternatively, an adjacent region 12*a-d* may be adjacent more than one peripheral region 11*a-d*. The one or more adjacent regions 12*a-d* may be located towards or in a central region of the inner wall 2 and the outer wall 3.

In the illustrated example of FIGS. 2 and 3, two peripheral regions 11*c*, 11*d* are provided—a left lateral wing region 11*d* (as viewed in FIG. 5) and a right lateral wing region 11*c*. In this example two adjacent regions 12*a-d* are provided, one next to each of the left and right lateral wing regions—a left adjacent region 12*d* and a right adjacent region 12*c*.

Each peripheral region 11*a-d* may be foldable about a fold line that extends between the peripheral region 11*a-d* and its adjacent region 12*a-d*. The at least one lateral wing region 11*c*, 11*d* may be foldable about a fold line 16*c*, 16*d* that extends in a generally vertical direction when the ostomy appliance 1 is in use. Optionally, an upper and/or a lower peripheral region 11*a*, 11*b* may be foldable about a fold line that extends in a generally horizontal direction when the ostomy appliance 1 is in use.

The flexible sheet material of the inner wall 2 and the outer wall 3 may be formed of polyurethane, polyethylene (PE), polyvinylidene chloride (PVDC) and/or ethylene-vinyl acetate (EVA). The flexible sheet material may have a thickness of 50 to 150 micrometres, preferably 75 to 100 micrometres.

Figure 1A:
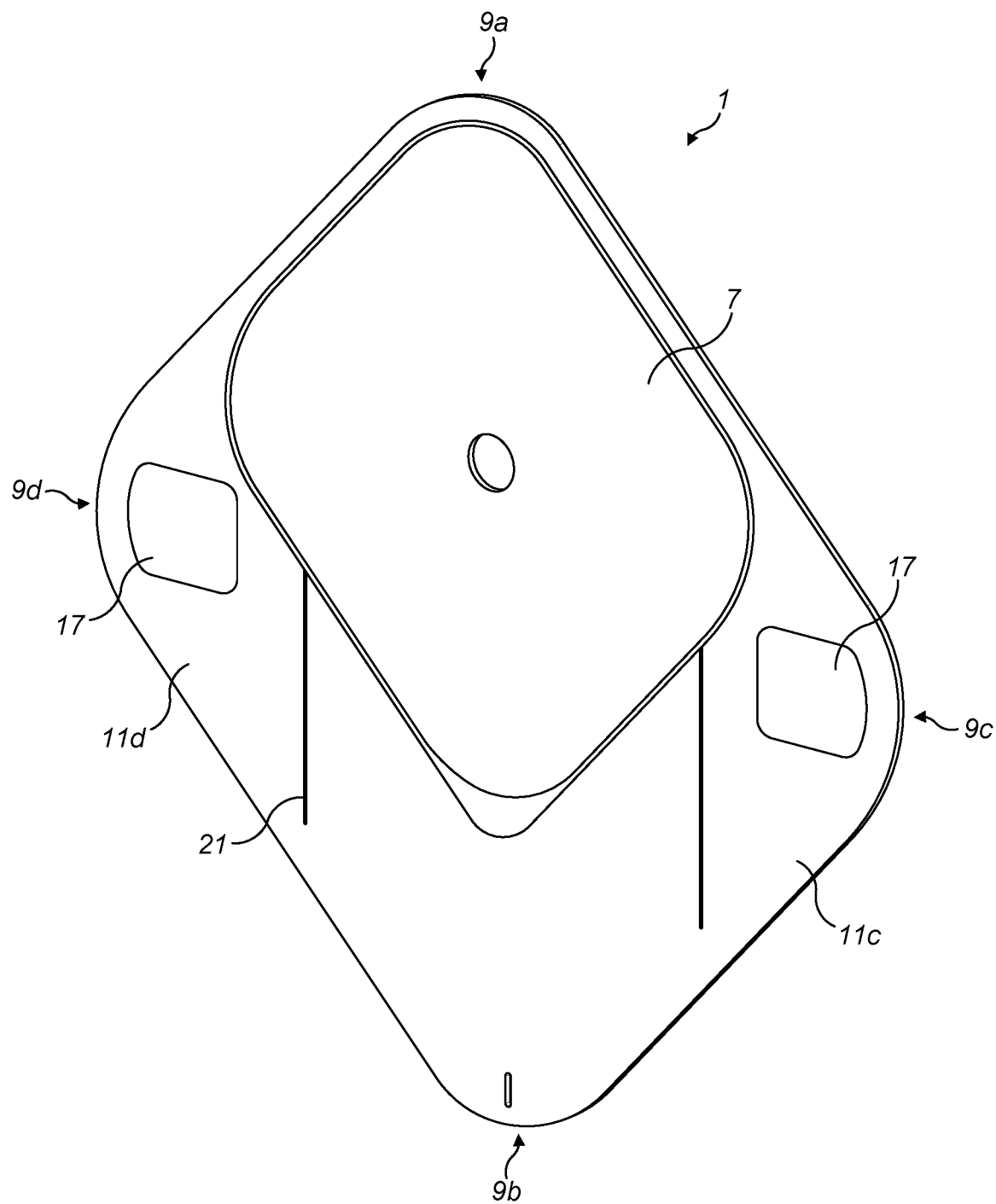
FIG. 1A illustrates a perspective view of another embodiment of ostomy appliance according to the present disclosure.

As shown in FIGS. 1 to 3, the at least one peripheral region 11*a-d* may comprise a stiffening member 17. Additionally or alternatively, the at least one adjacent region 12*a-d* may comprise a stiffening member 18. Complementary stiffening members 17, 18 may be provided on both the peripheral region 11*a-d* and the adjacent region 12*a-d* as shown in FIG. 1. Alternatively, stiffening members 18 may be provided only on the at least one peripheral region 11*a-d* and not on the at least one adjacent region 12*a-d* as shown in FIG. 1A. In a further non-illustrated alternative, stiffening members 17 may be provided only on the at least one adjacent region 12*a-d* and not on the at least one peripheral region 11*a-d*.

The one or more stiffening members 17, 18 are preferably covered by the inner comfort layer 5 to avoid contact between the skin of the ostomate and the stiffening members 17, 18.

In a non-illustrated variant, for each peripheral region 11, a single stiffening member may be provided that extends from the peripheral region 11*a-d* to the respective one adjacent region 12*a-d*. However, preferably and as illustrated the stiffening members 17, 18 of the at least one peripheral region 11*a-d* and the at least one adjacent region 12*a-d* may be separated from one another and may comprise two parts. The stiffening members 17, 18 of the at least one peripheral region 11*a-d* and the at least one adjacent region 12*a-d* may be separated by a gap 19 which may define the location of folding of the at least one peripheral region 11*a-d*.

The stiffening members 17, 18 of the at least one peripheral region 11*a-d* and the at least one adjacent region 12*a-d* may be located equidistant from the fold line 16*c-d* that extends between the at least one peripheral region 11*a-d* and the at least one adjacent region 12*a-d*.

Each stiffening member 17, 18 may have a rectangular shape. Each stiffening member 17, 18 may be of the same size. The stiffening members 17, 18 may have a length of 10 to 40 mm, a width of 10 to 30 mm and a thickness of 0.25 to 1.00 mm. The stiffening members 17, 18 may be formed of one or more of polystyrene, polypropylene, polyethylene. ethylene vinyl acetate (EVA) and/or thermoplastic polyurethane (TPU).

The stiffening members 17, 18 may be integrated in, or affixed to, the outer wall 3 but is preferably integrated in, or affixed to, the inner wall 2. In some embodiments each stiffening member 17, 18 is adhered to the inner wall 2 using an adhesive. The stiffening members 17, 18 may be located on an inner or an outer face of the inner wall 2.

In the example of FIG. 2, the stiffening members 17, 18 are each a rectangular piece of polystyrene measuring 30 mm by 20 mm by 0.50 mm that is adhered to the inner wall 2.

Alternatively or additionally, the one or more stiffening members may comprise one or more welds in the at least one peripheral region 11*a-d* and/or the at least one adjacent region 12*a-d*. Alternatively or additionally, the one or more stiffening members may comprise local thickening of the flexible sheet material of the at least one peripheral region 11*a-d* and/or the at least one adjacent region 12*a-d*.

In a non-illustrated variant, the one or more stiffening members may comprise a flexible hinge. The flexible hinge may be elastically movable between an unfolded and folded configuration. The flexible hinge may be biased into its folded configuration. For example the flexible hinge may be a piece of resilient polymer that is folded when unloaded. The flexible hinge may be plastically movable between an unfolded and folded configuration. For example, the flexible hinge may be a piece of aluminium foil. The flexible hinge may have bi-stable configurations—folded and unfolded.

One or more openings may be provided in the inner comfort layer 5 and/or the outer comfort layer 6 which are configured to receive a portion of the at least one peripheral region 11*a-d* of the inner wall 2 and outer wall 3 and to releasably retain the at least one peripheral region 11*a-d* in its folded configuration. The one or more openings may be so configured by one or more of their location, size and orientation. In some embodiments the one or more openings are provided in the inner comfort layer 5. In the following, the one or more openings will be described as being only in the inner comfort layer 5. However, openings of the same type as described may also or alternatively be provided in the outer comfort layer 6.

The one or more openings may be slits 21 in the inner comfort layer 5. The slits 21 may be straight slits. The slits 21 may pass through the full thickness of the inner comfort layer 5. Where the inner comfort layer 5 is a laminate, the slits 21 may pass through one or more layers of the laminate. The slits 21 may be orientated vertically when the ostomy appliance 1 is in use. The slits 21 may be orientated horizontally when the ostomy appliance 1 is in use. The inner comfort layer 5 may comprise two slits 21. The two slits 21 may be located symmetrically about a vertical mid-line of the ostomy appliance 1.

Alternatively, the inner comfort layer 5 may comprise three slits 21, with some slits 21 that are orientated vertically when the ostomy appliance 1 is in use and some slits 21 that are orientated horizontally when the ostomy appliance 1 is in use. In one example, two vertical slits 21 and one horizontal slits 21 are provided. In another example, two vertical slits 21 and two horizontal slits 21 are provided.

In a non-illustrated embodiment, a central region of the inner comfort layer 5 may be joined to a central region of the inner wall 2 along a central contact line. The central region may be located in between the one or more openings of the inner comfort layer 5. The central contact line may be located between the two slits 21 in the inner comfort layer 5 and preferably equidistant from each of the two slits 21, and preferably orientated parallel to the two slits 21. The central contact line may be a central weld line.

One or more layers of the ostomy appliance 1 may be pre-scored to assist in defining the location of fold lines 16c-d between the at least one peripheral region 11a-d and the at least one adjacent region 12a-d. For example, the inner wall 2 and/or outer wall 3 may be pre-scored.

One or more layers of the ostomy appliance 1 may be provided with additional means to assist in defining the location of fold lines 16c-d between the at least one peripheral region 11a-d and the at least one adjacent region 12a-d. For example, the inner comfort layer 5 and/or the outer comfort layer 6 may be provided with permanent creases to demarcate the location of the fold lines.

The ostomy wafer 7 may be located in register with the stomal inlet 20 of the inner wall 2. The ostomy wafer 7 may extend through the wafer aperture 14 of the inner comfort layer 5. The ostomy wafer 7 may be located in the upper peripheral region 11a of the inner wall 2 and the outer wall 3. The periphery of the ostomy wafer 7 preferably does not extend beyond the periphery of the inner wall 2 and the outer wall 3 in the unfolded configuration.

Figure 4:
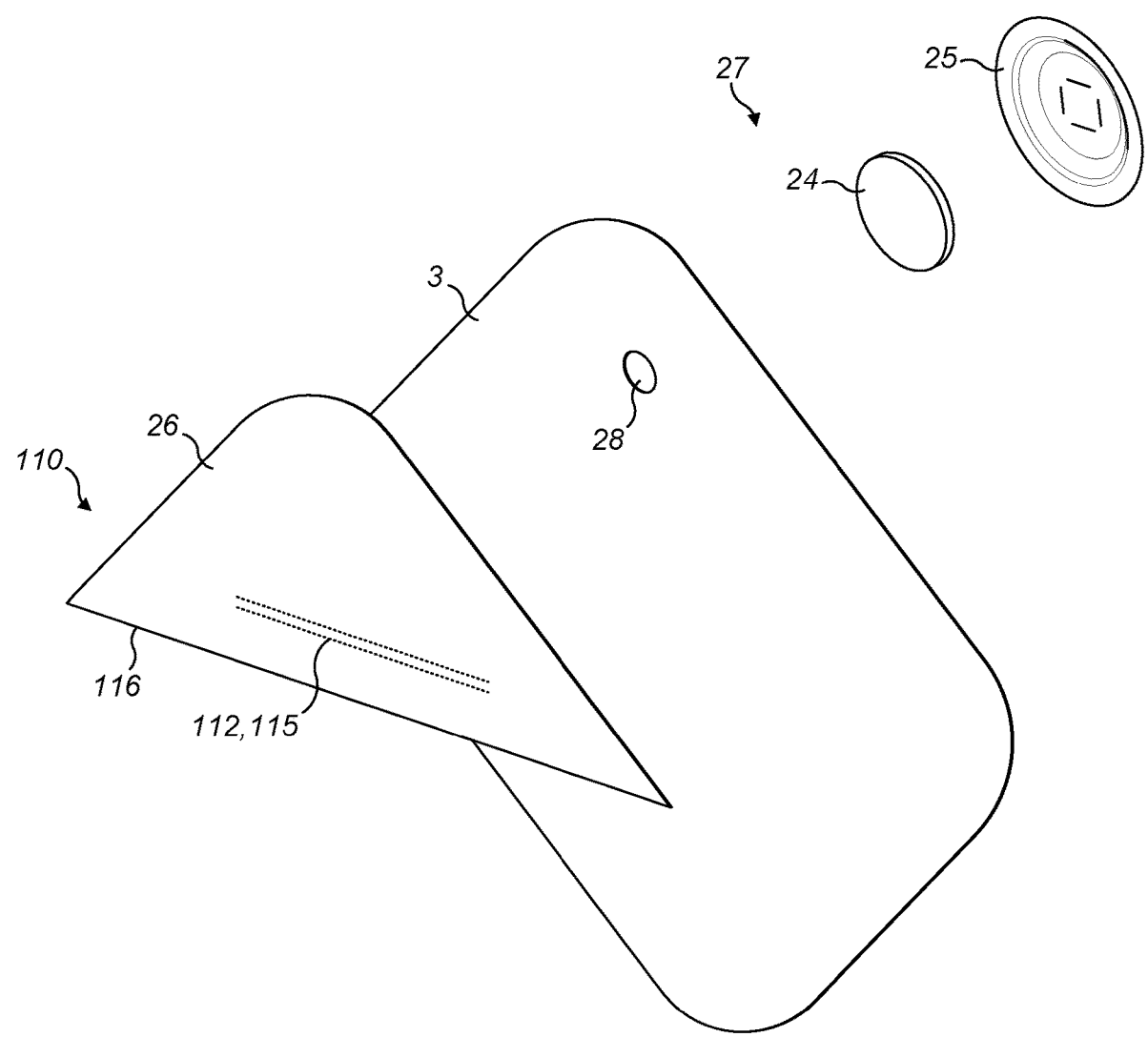
FIG. 4 illustrates an exploded perspective view of some more of the components of the ostomy appliance of FIG. 1.

The ostomy appliance 1 may be provided with a gas vent 27 for venting of stomal gases from the cavity. The ostomy appliance 1 may comprise a gas vent filter 24, which may be an odour filter, for example a charcoal or activated carbon filter, for reducing the release of unwanted odours from the cavity. As shown in FIG. 4, the gas vent filter 24 may form a part of the gas vent 27, which may comprise at least one gas vent aperture 28 located in the outer wall 3. The gas vent filter 24 may be covered by a filter cap 25 and the gas vent filter 24 and/or filter cap 25 may be located on the outer wall 3 over the at least one gas vent aperture 28. The at least one gas vent aperture 28 may permit the passage of gas from the cavity towards an exterior of the ostomy appliance through the gas vent filter 24 and filter cap 25.

Figure 17:
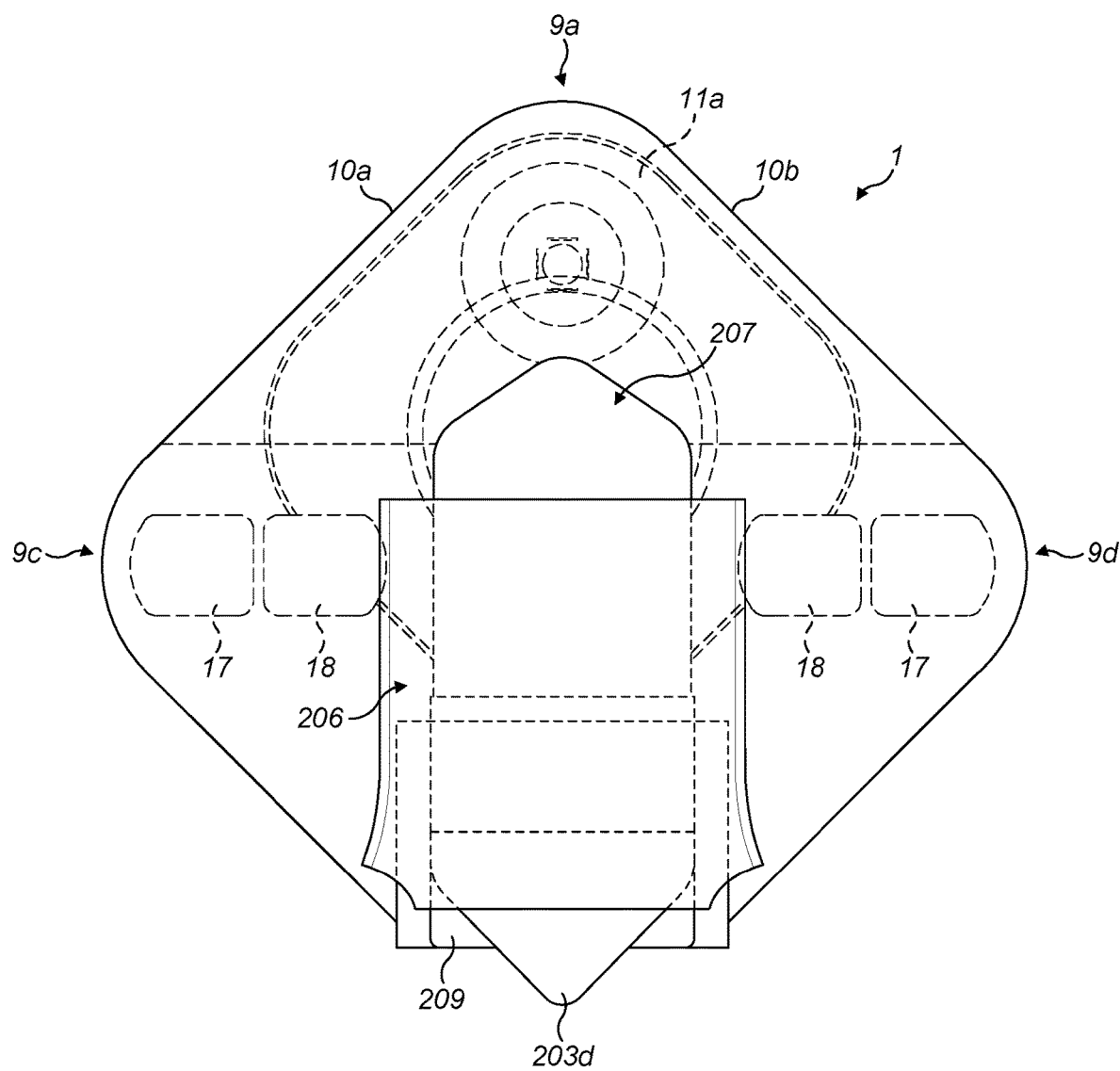
FIG. 17 illustrates a schematic view of the retractable drain of the ostomy appliance of FIG. 10 in the retracted configuration with the comfort layer omitted.

The gas vent 27 may be located, in use, in the upper half or more preferably upper quarter of the ostomy appliance 1. In particular, the centre of the at least one gas vent aperture 28 may be located, in use, above the centre of the stomal inlet 20. Preferably the entire perimeter of the at least one gas vent aperture 28 is located, in use, above the entire perimeter of the stomal inlet 20 as shown in FIG. 17. The term "above" is intended to mean that the at least one gas vent aperture 28 is located in use uppermost of the stomal inlet 20 along a line parallel to the inner and outer walls 2, 3 when in a flat configuration.

As shown in FIG. 2, the separation wall 4 may be located between the inner wall 2 and the outer wall 3. The separation wall 4 comprises a separation filter 100 for filtering stomal gases and/or stomal liquids from stomal solids contained in the stomal output. The separation filter 100 may thus prevent stomal solids from contacting the gas vent 27 and clogging or otherwise impairing the functionality of the gas vent filter 24.

The cavity of the ostomy appliance 1 may be sub-divided into two volumes by the separation wall 4 to form first and second chambers 101, 102 as best illustrated in FIG. 17. The first chamber 101 may extend between the separation wall 4 and the inner wall 2 and the second chamber 102 may extend between the separation wall 4 and the outer wall 3. The first and second chambers 101, 102 may have substantially the same volume or they may have different volumes. The second chamber 102 may have a larger volume than the first chamber 101, particularly if pleats 50 are present and are unfolded (as discussed further below).

The separation wall 4 may be joined to the inner wall 2 and outer wall 3 at or adjacent to a part or the whole of their peripheral edges, preferably by use of welding, adhesive or equivalent means. Welding is a preferred method of joining and the peripheral weld that joins the inner wall 2, outer wall 3 and separation wall 4 may be the whole or a portion of the peripheral weld 8 that joins the inner wall 2 and the outer wall 3. As shown in FIGS. 5 and 6, the peripheral weld 8 may extend around a full perimeter of the inner wall 2, outer wall 3 and separation wall 4 to create a fluid-tight seal there between. Therefore, the joining of the separation wall 4 with the inner and outer walls 2, 3 may be such that the first and second chambers 101, 102 are sealed from one another other than via the separation filter 100.

The separation wall 4 may have the same external shape and dimensions as the inner wall 2 and the outer wall 3 so that the separation wall 4 extends entirely across all of the surface area of the inner and outer walls 2, 3. However, the separation wall 4 may instead be joined around at least part of its peripheral edge to only one of the inner and outer walls 2, 3. Therefore, the separation wall 4 may extend across at least 50% or at least 75% of the surface area of the inner and/or outer walls 2, 3. The separation wall 4 may at least partially extend across a lower half or lower quarter of the ostomy appliance 1 and may, as illustrated, extend entirely across the inner and outer walls 2, 3 and particularly between the peripheral weld 8 joining the inner and outer walls 2, 3.

The separation wall 4 may comprise a flexible sheet material, which may be formed of polyurethane, polyethylene (PE), polyvinylidene chloride (PVDC) and/or ethylene-vinyl acetate (EVA). The flexible sheet material of the separation wall 4 may have a thickness of 50 to 150 micrometres, preferably 75 to 100 micrometres.

The separation wall 4 may comprise a hydrophobic and/or oleophobic coating applied to the flexible sheet material and/or the flexible sheet material may be hydrophobic and/or oleophobic.

The separation filter 100 is liquid and gas permeable such that stomal liquid and stomal gas can migrate through the separation filter 100 to the second chamber 102 from the stomal output in the first chamber 101. The separation filter 100 may be substantially impermeable to the stomal solids in the stomal output such that the stomal solids substantially remain within the first chamber 101. Thus the separation filter 100 may effectively separate the stomal output into stomal solids in the first chamber 101 and stomal liquid and stomal gas in the second chamber 102.

The separation filter 100 may comprise at least one wall aperture 103 and preferably an array of wall apertures 103. The separation filter 100 may be otherwise substantially impermeable to gas and liquid other than through the at least one wall aperture 103. The at least one wall aperture 103 may be laser perforated in the separation wall 4. The maximum diameter of each wall aperture 103 may be in the range of from about 0.03 mm to about 0.8 mm, from about 0.06 mm to about 0.8 mm or from about 0.1 mm to about 0.4 mm inclusive. The spacing between adjacent wall apertures 103 in the array may be in the range of from about 0.8 mm to about 2.2 mm or from about 1 mm to about 2 mm. The wall apertures 103 of the array may comprise a stochastic and/or regular distribution. Preferably the entire array has a regular distribution as shown in FIG. 2, although the array may have an entirely stochastic distribution or part of the array may comprise a stochastic distribution and part of the array may comprise a regular distribution.

The separation filter 100 and preferably array of wall apertures 103 may extend across at least 50%, at least 75% or at least 90% of the surface area of the separation wall 4. As illustrated in FIG. 2, the array of wall apertures 103 may extend entirely across the separation wall 4. The separation filter 100 may extend across at least the lower half or lower quarter of the separation wall 4 and/or inner and outer walls 2, 3. The separation filter 100 may extend across at least the upper half or upper quarter of the separation wall 4 and/or inner and outer walls 2, 3. The separation filter 100 may not extend into the region of the peripheral weld 8 and, prior to assembly, the separation wall 4 comprises a peripheral region without any wall apertures 103.

Figure 22:
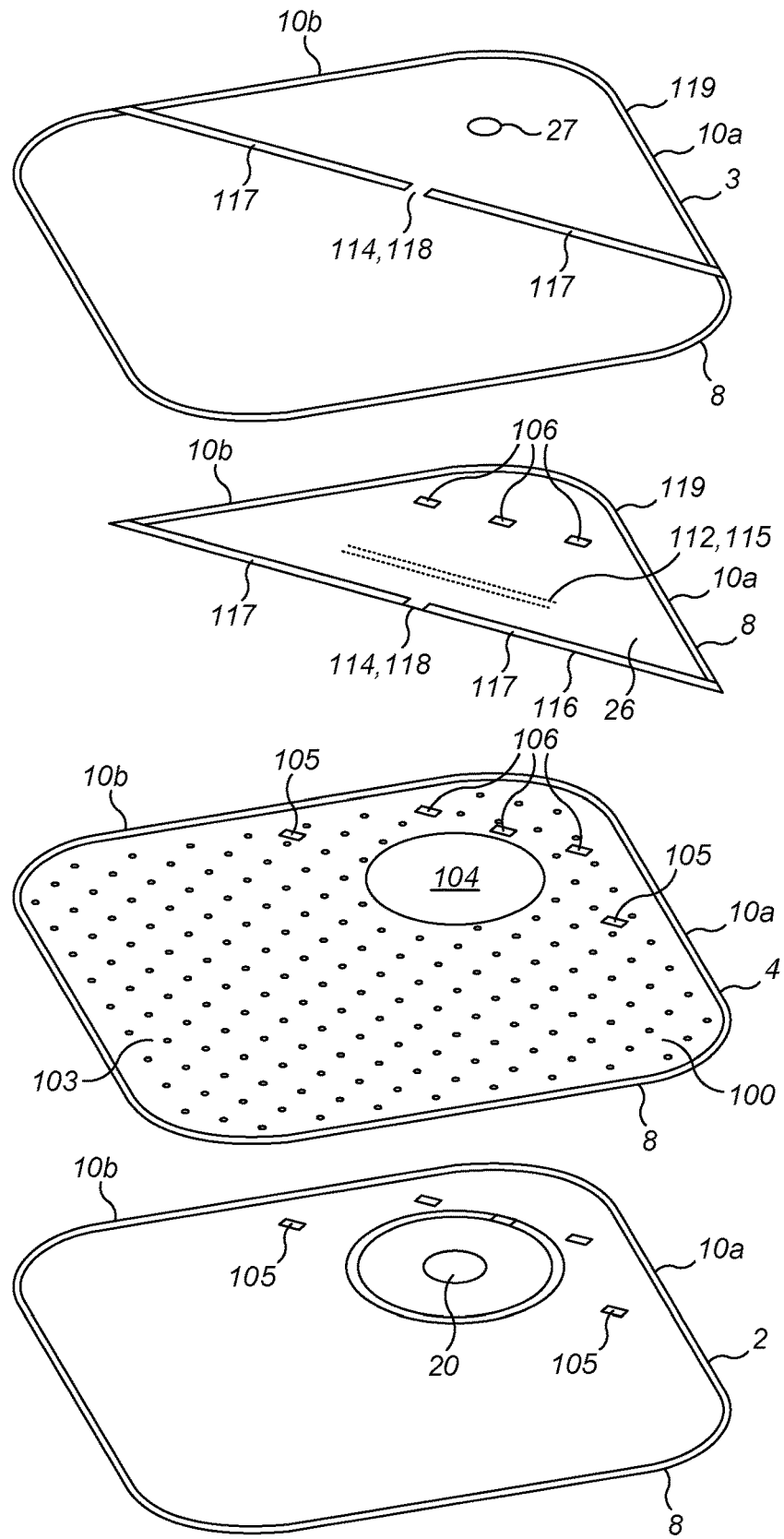
FIG. 22 illustrates an exploded perspective view of components of a further embodiment of an ostomy appliance showing a further embodiment of a separation wall and exemplary locations of attachment regions and seals.

FIG. 22 illustrates a further embodiment of the ostomy appliance 1, similar to that of FIG. 1, when in an exploded configuration and in which the separation filter 100 extends across part of the separation wall 4. In particular, the separation wall 4 comprises a non-perforated area 104 at least partially, in this example entirely, surrounded by the separation filter 100 and the wall apertures 103. The non-perforated area 104 comprises only the separation wall 4 without wall apertures 103 or other perforations therethrough. The non-perforated area 104 may be aligned with and adjacent to the stomal inlet 20 in the assembled ostomy appliance 1. The surface area of the non-perforated area 104 may be at least, preferably at least 110% of, the area of the stomal inlet 20. The non-perforated area 104 and stomal inlet 20 may be round as illustrated.

Figure 21:
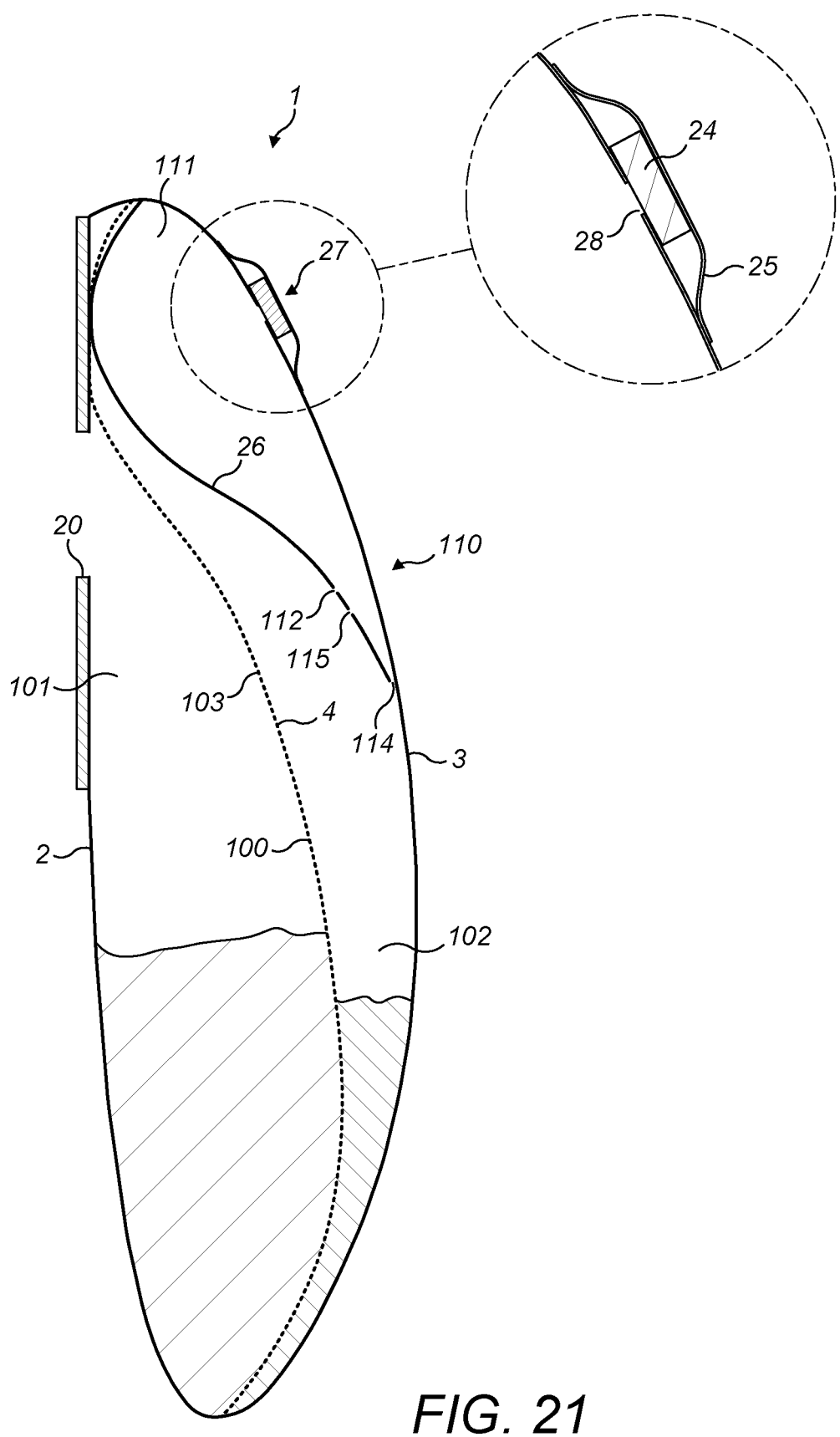
FIG. 21 illustrates a cross-sectional side view of the ostomy appliance of FIG. 1.

The ostomy appliance 1 may further comprise a protective structure 110 comprising a protective panel 26 for substantially protecting the gas vent 27 from liquid located in the cavity and second chamber 102. The protective panel 26 is attached to at least one wall 2, 3, 4, which as in the illustrated embodiment of FIG. 21 may be at least the outer wall 3 and more preferably the inner wall 2, outer wall 3 and separation wall 4. The protective panel 26 may define a protective chamber 111 around the gas vent 27 and the protective chamber 111 may be located within the cavity and second chamber 102. The protective structure 110 may comprise a protective chamber gas inlet 112 for allowing the stomal gas to migrate into the protective chamber 111 from the second chamber 102. The stomal gas may thus migrate through the protective chamber 111 to the gas vent 27 such that it can exit the ostomy appliance 1.

The protective structure 110 may also comprise a protective chamber liquid outlet 114 for allowing stomal liquid to migrate out of the protective chamber 111. Some stomal liquid may undesirably migrate into the protective chamber 111 when the ostomy appliance 1 is oriented with its outer wall 3 facing downwards such that gravity directs liquid through the protective chamber gas inlet 112. The protective chamber liquid outlet 114 may enable such stomal liquid to exit the protective chamber 111 back into the second chamber 102. Stomal gas entering the protective chamber 111 may force the stomal liquid out through the protective chamber liquid outlet 114.

The protective panel 26 may be substantially triangular in shape and thus have the same shape as upper portions of the inner and outer walls 2, 3. The edges of the protective panel 26 may extend from the upper apex 9a along the first and second edges 10a, 10b towards the opposed lateral apexes 9c, 9d. The protective panel 26 may comprise a lower edge 116, which may be straight, extending between the first and second edges 10a, 10b. The lower edge 116 may extend to between 25% and 50% of the length of the outer wall 3 from the upper apex 9a.

The protective chamber gas inlet 112 may be located in the protective panel 26 and may comprise at least one panel aperture 115, preferably a plurality of panel apertures 115, preferably an array of panel apertures 115, through the protective panel 26. The at least one panel aperture 115 may be laser perforated through the protective panel 26. The maximum diameter of each panel aperture 115 may be in the range of from about 0.03 mm to about 0.8 mm, from about 0.06 mm to about 0.8 mm or from about 0.1 mm to about 0.4 mm inclusive. The spacing between adjacent panel apertures 115 in the array may be may be in the range of from about 0.8 mm to about 2.2 mm or from about 1 mm to about 2 mm and may be about 1.5 mm. The array may be up to about 70 mm or about 100 mm wide and up to about 4 mm or about 2 mm high.

Preferably, as illustrated, the array comprises at least two lines of panel apertures 115 extending parallel to one another. The lines of the array may extend substantially parallel to the protective chamber liquid outlet 114 and the lower edge 116 of the protective panel 26.

The protective chamber liquid outlet 114 may be formed between the protective panel 26 and the outer wall 3. As best shown in the embodiment of FIG. 22, at or adjacent to its lower edge 116, the protective panel 26 may be attached to the outer wall 3 at a plurality of attachment regions 117 and the protective chamber liquid outlet 114 may comprise a least one outlet gap 118 between the plurality of attachment regions 117. The attachment regions 117 may be between opposing surfaces of the protective panel 26 and outer wall 3 as illustrated. The plurality of attachment regions 117 and the at least one outlet gap 118 therebetween may extend substantially parallel to, adjacent to and/or along the lowermost edge of the protective panel 26. The plurality of attachment regions 117 preferably comprises welding between the outer wall 3 and protective panel 26. The at least one outlet gap 118 may be at least about 3 mm wide and may be about 5 mm wide. The plurality of attachment regions 117 may be at least about 2 mm high and may be about 3 mm high. The protective panel 26 may be sealed by a protective panel seal 119 along its upper apex 9a to the outer wall 3 and, optionally, the inner wall 2 between the ends of the plurality of attachment regions 117 and around the gas vent 27. The protective panel seal 119 may form part of the peripheral seal 8.

The protective panel 26 may comprise a substantially impermeable sheet other than in the region of the protective chamber gas inlet 112. The protective panel 26 may therefore comprise a flexible sheet material, which may be formed of polyurethane, polyethylene (PE), polyvinylidene chloride (PVDC) and/or ethylene-vinyl acetate (EVA). The flexible sheet material of the protective panel 26 may have a thickness of 50 to 150 micrometres, preferably 75 to 100 micrometres.

The protective chamber gas inlet 112 may be located between the protective chamber liquid outlet 114 and the gas vent 27 (i.e. when the appliance 1 is viewed in plan view above the outer wall 3). In use, the protective chamber gas inlet 112 and protective chamber liquid outlet 114 may be located below the gas vent 27 (i.e. the gas vent 27 is located uppermost of the protective chamber gas inlet 112 and protective chamber liquid outlet 114 along a line parallel to the inner and outer walls 2, 3 when in a flat configuration). Thus the likelihood of liquid entering the protective chamber 111 and contacting the gas vent 27 is reduced. As a result, the plurality of attachment regions 117 may be located, in use, lower than the protective chamber gas inlet 112 and gas vent 27.

The spacing between the protective chamber gas inlet 112 and protective chamber liquid outlet 114 may be in the range of about 10 mm to about 20 mm or about 10 mm to about 15 mm and may be for example about 12 mm, about 12.5 mm or about 14 mm. The spacing between the protective chamber liquid outlet 114 and centre of the gas vent 27 may be in the range of about 25 mm to about 40 mm or about 30 mm to about 38 mm and may be about 34 mm.

FIG. 22 further illustrates a preferred arrangement in which the separation wall 4 is attached to the inner wall 2 by at least one first attachment region 105. The protective panel 26, separation wall 4 and inner wall 2 may be attached by at least one second attachment region 106. If the separation wall 4 is not present the at least one second attachment region 106 may attach the protective panel directly to the inner wall 2. In addition, in some embodiments the at least one second attachment region 106 may not attach the separation wall 4 and inner wall 2. The first and second attachment regions 105, 106 hold the separation wall 4 to the inner wall 2 when the ostomy appliance 1 is inflated by the stomal output entering through the stomal inlet (which may comprise any gases or fluids or solids produced by an ostomate) and allow an open volume to form between the separation wall 4 and protective panel 26 and/or outer wall 3. The at least one second attachment region 106 holds the protective panel 26 to the separation wall 4 and inner wall 2 when the ostomy appliance is inflated and allows an open volume to form between the protective panel 26 and outer wall 3.

The first and/or second attachment regions 105, 106 may be discrete areas of attachment and may be separated from, and may be at least about 7 mm from, the first and second edges 10a, 10b of the inner walls 2. The ostomy appliance 1 may comprise at least two first attachment regions 105 and/or up to five attachment regions 105. The ostomy appliance 1 may comprise at least two second attachment regions 106 and/or up to four second attachment regions 106. At least one wall aperture 103 may be located between the first and/or second attachment regions 105, 106 and the peripheral weld 8 and/or first and second edges 10a, 10b of the separation wall 4. The first and/or second attachment regions 105, 106 may comprise at least one weld, tack weld, spot weld, adhesive or other such attachment means. The first and/or second attachment regions 105, 106 may have a maximum dimension of less than about 10 mm, less than about 7 mm or of about 5 mm and may be substantially rectangular. The first and/or second attachment regions 105, 106 may be located in the upper half of the inner and separation walls 2, 4. At least one of the first and second attachment regions 105, 106 may be located above the gas vent 27 and as illustrated in FIG. 22 all of the first and second attachment regions 106 may be located above the gas vent 27. The second attachment regions 106 may be located above the first attachment regions 106. The at least one second attachment region 106 may be located above the non-perforated area 104 and the first attachment regions 105 may be located on either side of the non-perforated area 104.

As shown in FIG. 3, the inner wall 2, separation wall 4, the stiffening members 17, 18 and the ostomy wafer 7 may be assembled into a first sub-assembly. The ostomy wafer 7 may comprise an adhesive 30 and a release liner 31. The ostomy wafer 7 may be mounted to the inner wall 2 by a suitable means, for example, by use of adhesive. The stiffening members 17, 18 may then be adhered to the inner wall 2, preferably to an external face of the inner wall 2 not facing into the cavity by a suitable means, for example, by use of adhesive.

As shown in FIG. 4, the outer wall 3, the protective panel 26, the gas vent filter 24 and the filter cap 25 may be assembled into a second sub-assembly. The protective panel 26 may be joined to the outer wall 3 by means of a plurality of the plurality of attachment regions 117. The gas vent filter 24 and filter cap 25 may be joined to an exterior face of the outer wall 3 by a suitable means, for example by use of an adhesive.

The first subassembly and the second subassembly may then be assembled together with the inner comfort layer 5 and the outer comfort layer 6 to form the ostomy appliance. Preferably the first attachment regions 105 are applied to attach the inner and separation walls 2, 4. Preferably the second attachment regions 106 are applied to attach the inner and separation walls 2, 4 and the protective panel 26. Preferably welding of the peripheral weld 8 is used to join together the first subassembly, the second subassembly, the inner comfort layer 5 and the outer comfort layer 6.

In use, the ostomy appliance 1 may be mounted to the body of the ostomate using the ostomy wafer 7. As shown in FIG. 7, the ostomy appliance 1 may adopt an unfolded configuration and a folded configuration. Preferably in both the unfolded configuration and the folded configuration the periphery of the ostomy wafer 7 does not extend beyond the periphery of the inner wall 2 and the outer wall 3 such that the ostomy wafer 7 is hidden from view.

Advantageously, the ostomy appliance 1 may be mounted to the ostomate with the lower apex 9b lowermost, e.g. closest to the ground when the ostomate is standing. It has been found that the combination of a cavity formed from an inner wall 2 and an outer wall 3 of rectangular, preferably square, shape which are orientated with one apex 9 lowermost may provide beneficial shaping of the ostomy appliance 1 when filled. In particular, it has been found that the edges 10a-d of the inner wall 2 and outer wall 3 may be subjected to less crinkling when the cavity is filled and also that the opposed lateral apexes 9c, 9d may be able to lie closer to the body of the ostomate when the cavity is filled. This can lead to a reduced degree of pulling on the ostomy wafer 7 and a reduction in the visual bulk of the ostomy appliance 1 beneath clothing.

In addition, it has been found advantageous to position one apex 9 lowermost where the ostomy appliance 1 is intended to be mounted to the torso region of the ostomate. In this way discretion may be enhanced as the ostomy appliance 1 may more easily be perceived by third parties as a loose article of clothing, e.g. a shirt tail, rather than a medical device.

In the folded configuration the cavity may have a first useable volume which may be 120 to 400 ml. In the unfolded configuration the cavity may have a second useable volume which may be 350 to 650 ml.

Typically, a user after first mounting the ostomy appliance 1 will configure the ostomy appliance 1 into its folded state. The ostomy appliance 1 can be brought into the folded state by folding the inner wall 2 and the outer wall 3 as well as the inner comfort layer 5 and the outer comfort layer 6 of one or more of the peripheral regions 11a-d inwardly or outwardly into their folded configuration to overlie the at least one adjacent region 12a-d as shown in FIG. 7. This folding involves an 'external' fold (towards or away from the body of the ostomate) of the inner wall 2 and the outer wall 3 (and where present the inner comfort layer 5 and the outer comfort layer 6) such that the inner wall 2 (I) and the outer wall 3 (O) are each rotated about the fold line 16c-d in the same sense, i.e. either both the inner wall 2 and the outer wall 3 being folded towards the body of the ostomate or both the inner wall 2 and the outer wall 3 being folded away from the body of the ostomate. For example, in the case of an external fold towards the body of the ostomate, after the external fold has been completed, the wall layers are ordered OIIO when listed from an outer side of the ostomy appliance to an inner side of the ostomy appliance (where 'O' stands for an outer wall layer and 'I' stands for an inner wall layer). In another example, in the case of an external fold away the body of the ostomate, after the external fold has been completed, the wall layers are ordered IOOI when listed from an outer side of the ostomy appliance to an inner side of the ostomy appliance. This is in contrast to the formation of a pocket where the inner wall 2 and outer wall 3 are pushed 'internally' to form a pocket. In the case of a pocket the wall layers are ordered OOII when listed from an outer side of the ostomy appliance to an inner side of the ostomy appliance.

When in use and in its folded configuration, the at least one peripheral region 11a-d may preferably be located between the adjacent region 12a-d and a body of an ostomate wearing the ostomy appliance 1.

A portion of the at least one peripheral region 11a-d may be inserted into one of the openings, for example slits 21, to releasably retain the at least one peripheral region 11a-d in its folded configuration. The one or more openings of the at least one comfort layer 5, 6 may be configured to receive and to releasably retain an apex 9 of the at least one peripheral region 11a-d.

In some embodiments both lateral wing regions 11c, 11d may be folded inwardly. The ostomy appliance 1 may thus be folded into a substantially hexagonal shape in its folded state as shown in leftmost view of FIG. 7.

In some embodiments only one lateral wing region 11c, 11d is folded inwardly. Additionally or alternatively, other peripheral regions 11a, 11b may be folded inwardly, for example the lower peripheral region 11b encompassing the lower apex 9b may be folded upwardly and/or the upper peripheral region 11a encompassing the upper apex 9a may be folded downwardly. Additional openings in the inner comfort layer 5 may be provided to retain these other peripheral regions, for example horizontally-orientated openings.

Advantageously, the stiffening members 17, 18 may act to rigidify the one or more peripheral regions 11a-d to make them easier to fold and to improve retention in the openings, for example slits 21. Further, the stiffening members 17, 18 may advantageously help to define and control the location of fold lines 16c-d.

The central contact line (where present) may assist in promoting retention of the at least one peripheral region 11a-d in the openings, for example slits 21, of the inner comfort layer 5 by restricting relative movement between the inner comfort layer 5 and the inner wall 2. In particular, the central contact line may limit lateral relative movement of the layers.

In its folded state the ostomy appliance 1 can receive a quantity of stomal output while retaining the one or more peripheral regions 11a-d in their folded configuration. Advantageously, during this period of use the ostomy appliance 1 may be more discreet due to its reduced footprint. In some embodiments the ostomy appliance 1 provides a relatively slim width due to the folded lateral wing regions 11c, 11d which is more easily hidden under clothing.

As the cavity continues to fill a point will be reached where the one or more peripheral regions 11a-d will be unfolded so that the ostomy appliance 1 is brought into its unfolded configuration. The at least one peripheral region 11a-d may be spontaneously unfoldable from its folded configuration when the cavity is subject to a build-up of pressure. The build-up of pressure may be due to an increase in gas pressure and/or fluid pressure. Advantageously, the unfolding may take place without manual intervention by the ostomate, i.e. solely under the driving force of the build-up of internal pressure in the cavity which overcomes the retaining force imparted by the inner comfort layer 5 on the at least one peripheral region 11a-d.

Thus, as the cavity fills the at least one peripheral region 11a-d can 'spring' or 'slide' or 'pop' free of the opening in the inner comfort layer 5 allowing the at least one peripheral region 11a-d to unfold and increase the useable volume of the cavity.

Advantageously, the user may also choose to manually unfold the at least one peripheral region 11a-d which promotes user-control of their ostomy appliance 1.

Figure 9:
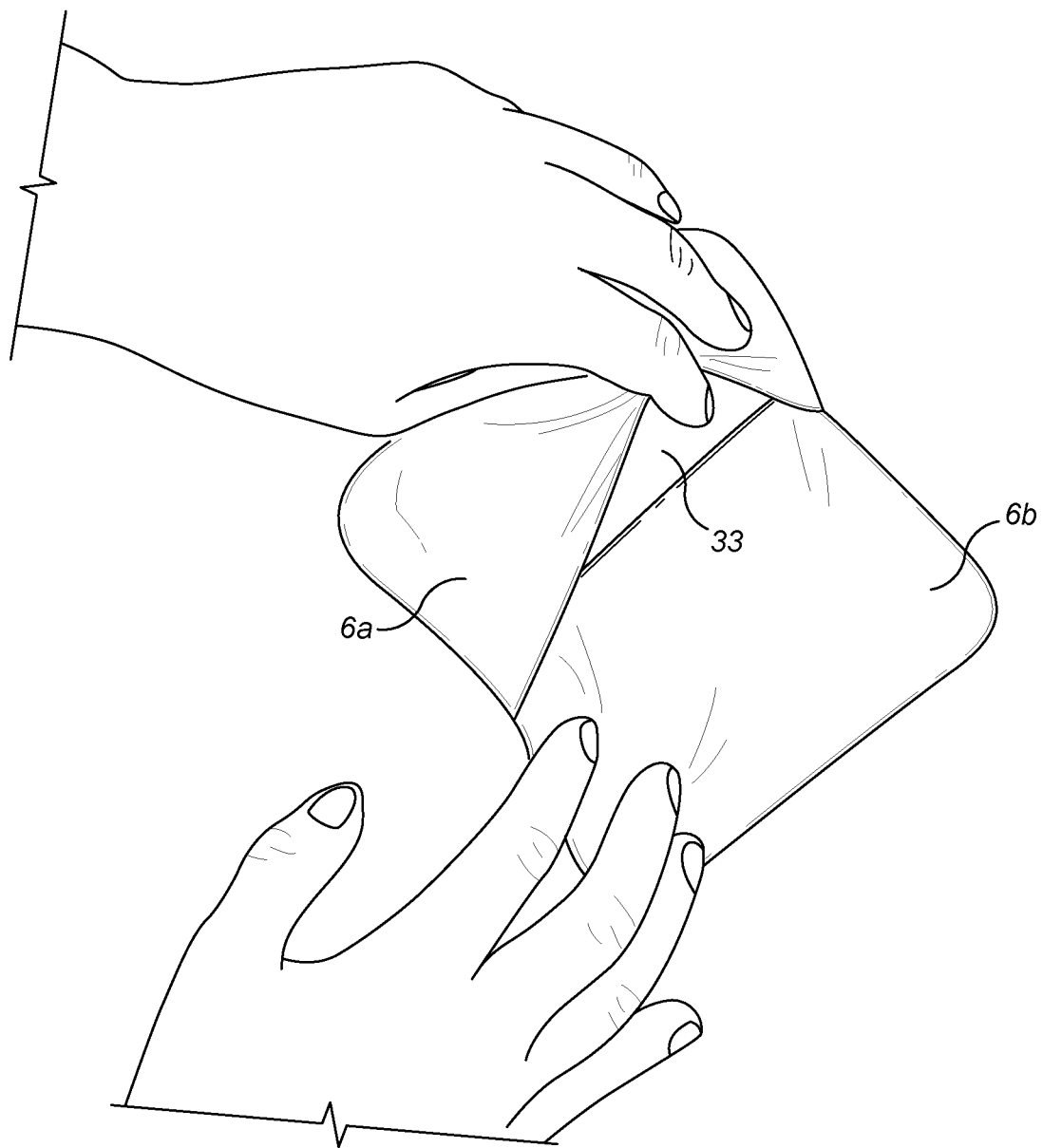
FIG. 9 a view illustrating use of an ostomy appliance according to the present disclosure.

During use, the user can inspect the cavity by pulling apart the first part 6a and the second part 6b of the outer comfort layer 6 to open a window opening 33 as shown in FIG. 9. The oblique angling of the window opening 33 may beneficially maximise the size of the window opening 33 and may also provide a more ergonomic orientation of the window opening 33 when the ostomy appliance 1 is mounted to the torso of an ostomate.

In use, inside the cavity stomal output is received in the first chamber 101 from the stomal inlet 20. Stomal liquid and stomal gas are filtered through the separation filter 100 to the second chamber 102 whilst the stomal solids remain in the first chamber 101. The stomal liquid substantially remains within the second chamber 102 (although residual amounts will also remain in the first chamber 101) and the stomal gas is able to exit the ostomy appliance 1 via the gas vent 27. The stomal solids are substantially prevented from reaching the gas vent 27 by the separation filter 100. The protective structure 110 receives the gas through the protective chamber gas inlet 112 and communicates the gas through the protective chamber 111 to the gas vent 27. The gas exits the ostomy appliance 1 through the at least one gas vent aperture 28, the gas vent filter 24 and the filter cap 25. Any stomal liquid that reaches the protective chamber 111 can exit via the protective chamber liquid outlet 114 and thus any contact it may have with the gas vent 27 may be minimised.

A second example embodiment of an ostomy appliance 1 according to the present disclosure is shown in FIGS. 10 to 19. Only those features that differ in this embodiment compared to the previous embodiment will be described in detail in the following description. For features that are common to one or more embodiments, reference should be made to the description as a whole.

Compared to the first embodiment of ostomy appliance 1, the ostomy appliance 1 of the second embodiment is configured as an open appliance and further comprises a retractable drain 40. FIGS. 10 to 15 show the retractable drain 40 in an extended configuration.

Figure 14:
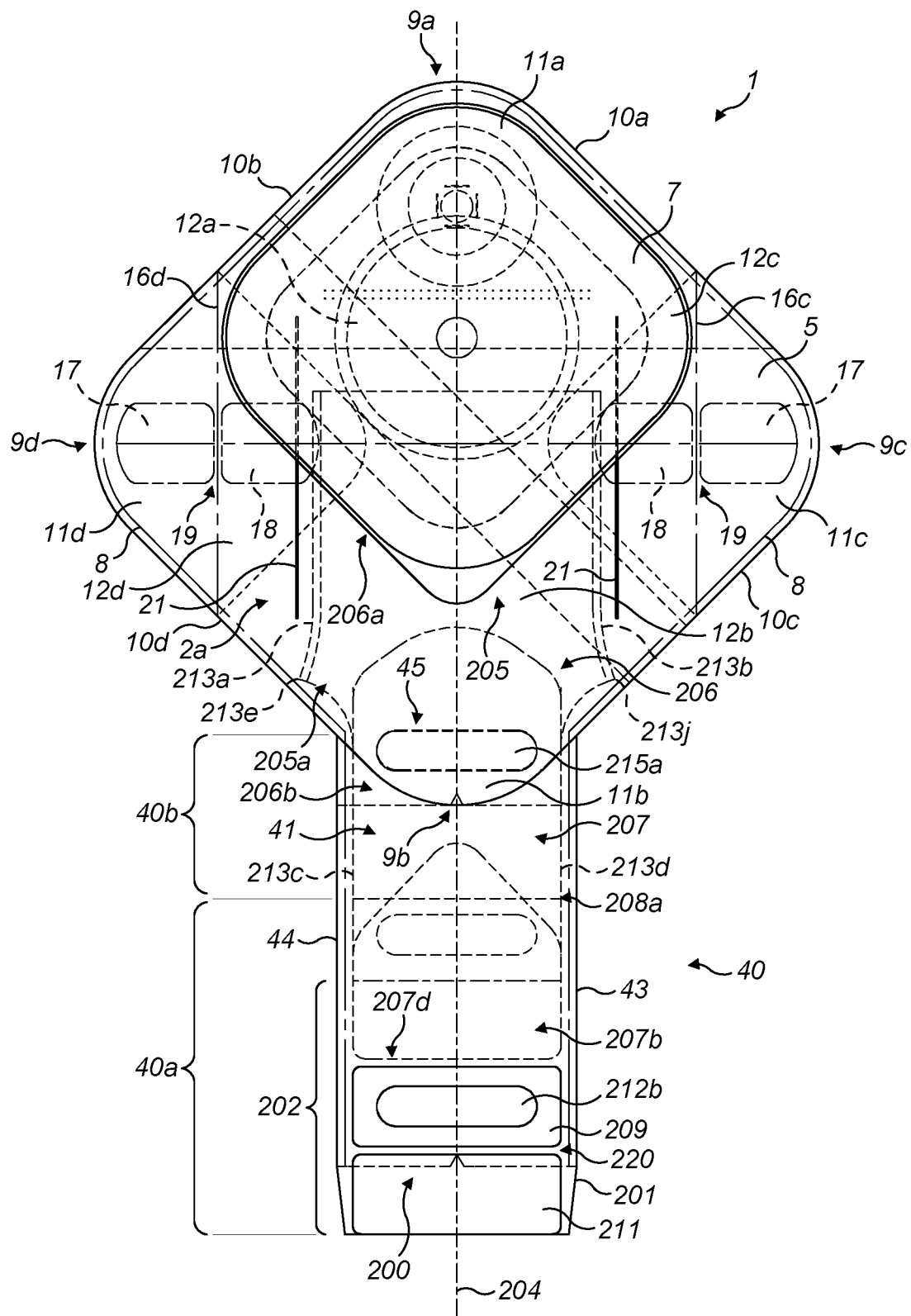
FIG. 14 illustrates a schematic rear view of the ostomy appliance of FIG. 10.

The retractable drain 40 may take the general form of an elongate extension of the inner wall 2 and the outer wall 3 that together define an elongate drain passage that extends from the cavity to an outlet opening 200 located at a lower end of the retractable drain as shown in FIG. 14.

Figure 12:
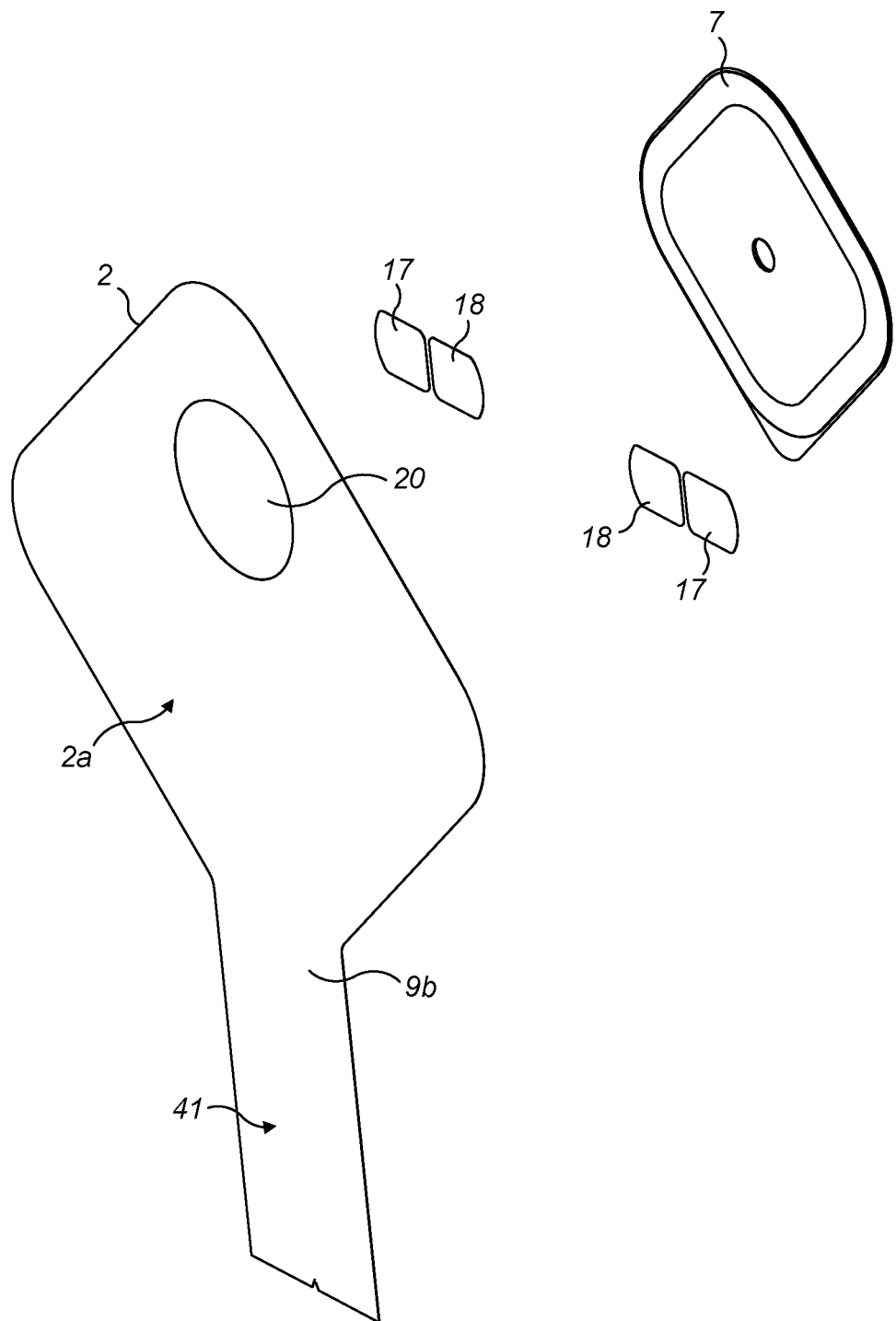
FIG. 12 illustrates a schematic exploded perspective view of some of the components of the ostomy appliance of FIG. 10.
Figure 13:
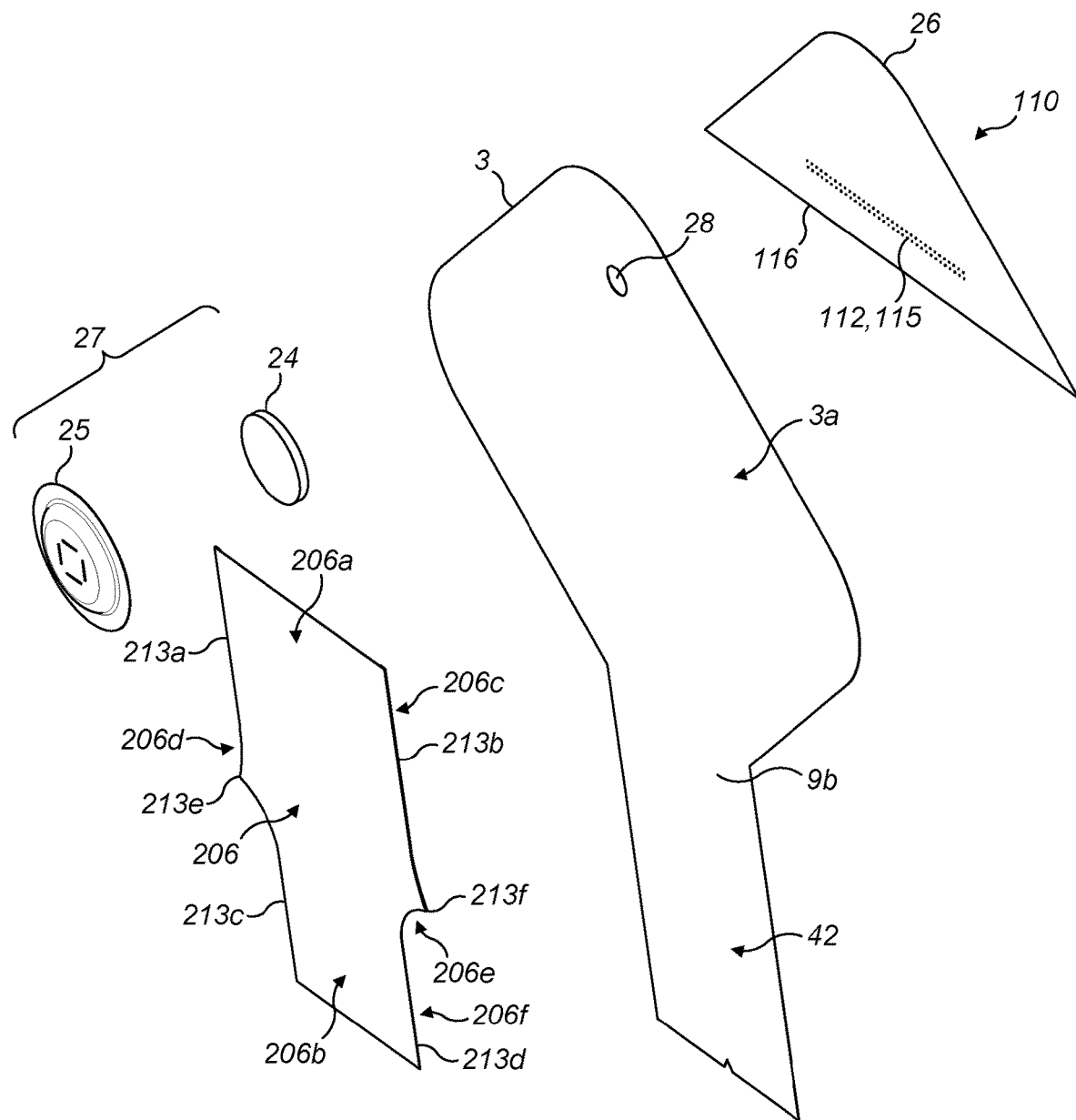
FIG. 13 illustrates a schematic exploded perspective view of some further components of the ostomy appliance of FIG. 10.

As shown in FIG. 12, the inner wall 2 may comprise a main body portion 2a and an inner drain portion 41. Likewise, as shown in FIG. 13, the outer wall 3 may comprise a main body portion 3a and an outer drain portion 42. The inner drain portion 41 may extend from the main body portion 2a of the inner wall 2. The outer drain portion 42 may extend from the main body portion 3a of the outer wall 3. The inner drain portion 41 and the main body portion 2*a* may be formed from the same, integral, sheet of flexible sheet material, for example by cutting or stamping them out of sheet material as a single part. Likewise, the outer drain portion 42 and the main body portion 3*a* may be formed from the same, integral, sheet of flexible sheet material, for example by cutting or stamping them out of sheet material as a single part.

The main body portions 2*a*, 3*a* may be a quadrilateral-shaped portions. For example, the main body portions 2*a*, 3*a* may each be a diamond-shaped portion, a rhombus-shaped portion, or a square-shaped portion.

The main body portions 2*a*, 3*a* of the inner wall 2 and outer wall 3 may be joined together around their peripheral edges by use of welding, adhesive or equivalent means. Welding is a preferred method of joining the inner wall 2 and the outer wall 3. As shown in FIG. 14, a peripheral weld 8 may extend around at least a portion of the perimeter of the main body portions 2*a*, 3*a* of the inner wall 2 and the outer wall 3 to create a fluid-tight seal there between. The peripheral weld 8 may have a width of 1 to 3 mm, preferably about 2 mm.

Preferably the retractable drain 40 extends from at or near a lower apex 9*b* of the main body portions 2*a*, 3*a* as shown in FIG. 14.

The inner drain portion 41 and/or the outer drain portion 42 may be generally rectangular along the majority of their length.

Figure 15:
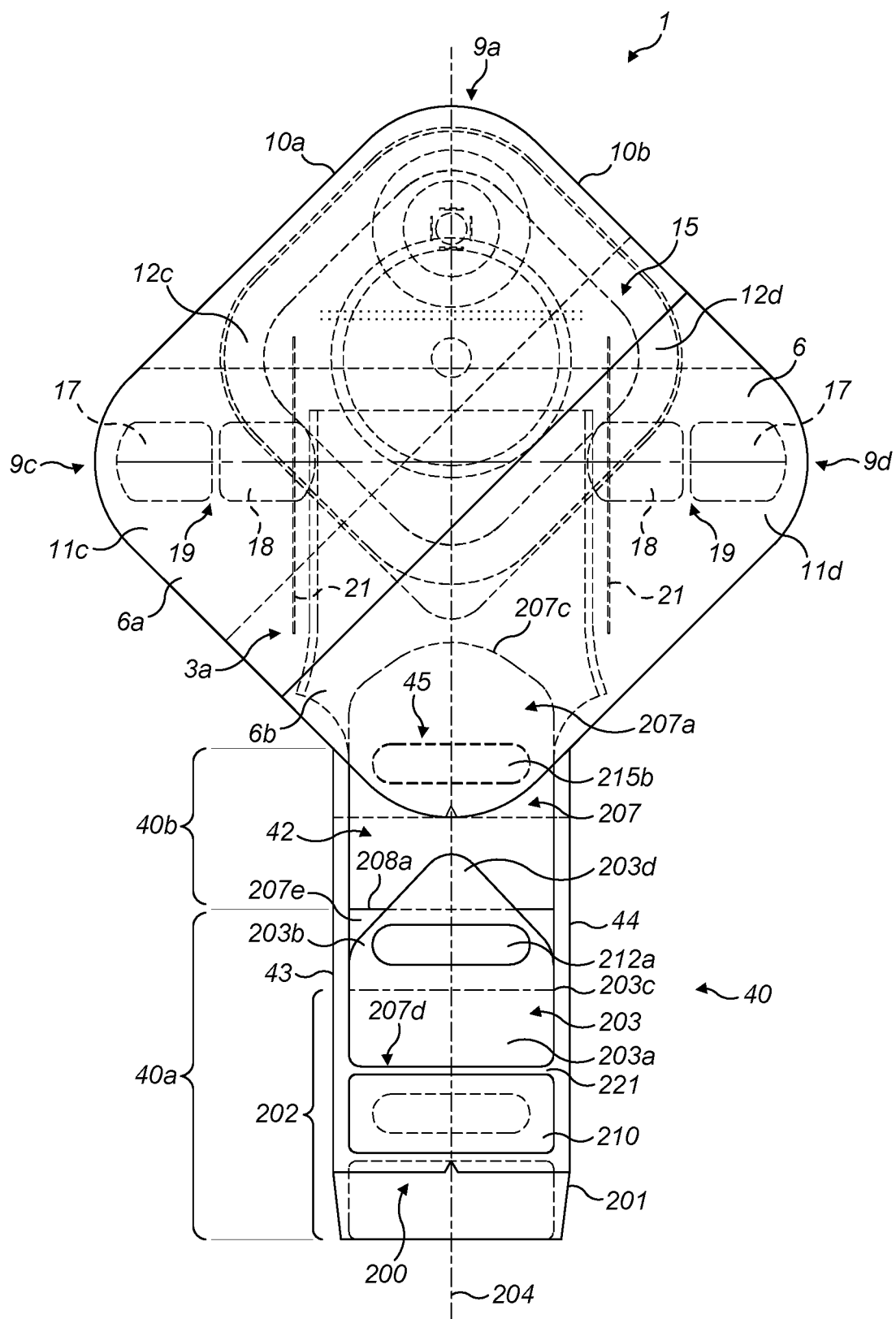
FIG. 15 illustrates a schematic front view of the ostomy appliance of FIG. 10.

Lateral edges 43, 44 of the retractable drain 40 may be generally parallel to each other, such that the retractable drain 40 has a constant width along a majority of its length, and optionally along all of its length. The inner drain portion 41 may extend further from the cavity (i.e. have a longer length) than the outer drain portion 42, forming a lip 201 at the outlet opening 200 of the retractable drain 40 as shown in FIGS. 14 and 15.

The outer and/or inner drain portion 41, 42 may have converging sides at their lower ends adjacent the outlet opening 200. In the illustrated example of FIG. 14 the lateral edges 43, 44 are parallel along their length and the lip 201 has a tapered shape.

The inner drain portion 41 may be joined to the outer drain portion 42 at their respective lateral edges 43, 44 to form a fluid tight seal. The join may be formed by use of welding, adhesive or equivalent means. Welding is a preferred method of joining the inner drain portion 41 and the outer drain portion 42.

The joins between the inner drain portion 41 and the outer drain portion 42 may preferably comprise a continuation of the peripheral join extending around the main body portions 2*a*, 3*a*. For example, the peripheral weld 8 may start adjacent to the outlet opening 200 on a left hand side of the ostomy appliance 1 (as viewed in FIG. 14) and extend as a continuous weld up the lateral edge 43, clockwise around the four sides of the main body portions 2*a*, 3*a* and down the lateral edge 44 to a point adjacent to the outlet opening 200 on a right hand side of the ostomy appliance 1 (as viewed in FIG. 14).

Communication between the cavity and the elongate drain passage may be via a drain inlet 45 that may be defined as the point of transition between the cavity and the retractable drain 40. The drain inlet 45 may function to allow passage of stomal output from the cavity into the retractable drain 40 when the retractable drain 40 is in the extended configuration. The outlet opening 200 may to allow outflow of the stomal output from the retractable drain 40 when the retractable drain 40 is in the extended configuration.

The inner comfort layer 5 and the outer comfort layer 6 may define an opening 130 therebetween as shown in FIG. 18*b* through which the retractable drain 40 is moveable between the extended configuration and the retracted configuration. The ostomy appliance 1 may comprise a closure 215 for closing the opening 130, the closure 215 being operable to retain the retractable drain 40 when the retractable drain 40 is in the retracted configuration. The closure 215 may comprise a first closure element 215*a* arranged on the inner comfort layer 5 and a second closure element 215*b* arranged on the outer comfort layer 6. The first closure element 215*a* and the second closure element 215*b* may comprise any suitable fastener elements, for example hook-and-loop type fastener elements.

The separation wall 4 may be joined to the inner wall 2 and outer wall 3 at or adjacent to a part or the whole of the peripheral edges of the main body portions 2*a*, 3*a*, preferably by use of welding, adhesive or equivalent means. Welding is a preferred method of joining and the peripheral weld that joins the inner wall 2, outer wall 3 and separation wall 4 may be the whole or a portion of the peripheral weld 8 that joins the inner wall 2 and the outer wall 3. As shown in FIG. 14, the welding of the separation wall 4 may extend around the four edges of the main body portions 2*a*, 3*a*. This portion of the weld may join both the inner wall 2 and the outer wall 3 to the separation wall 4. A lower portion of the separation wall 4 may extend into an upper portion of the retractable drain 40 as shown in FIG. 18. The welding of the edges of the separation wall 4 may also extend down into the retractable drain 40 to join the edges of the lower portion of the separation wall 4 to the edges of the inner wall 2 and the outer wall 3. However, the lowermost edge of the separation wall 4 is left unattached from the inner wall 2 and the outer wall 3. In this way the folding of the retractable drain 40 when moved into the retracted configuration folds the inner wall 2, outer wall 3 and the separation wall 4 such that the first and second chambers 101, 102 are sealed from each other (other than via the separation filter 100). However, the lowermost edge being unattached permits stomal output from the first chamber 101 and the second chamber 102 to enter the retractable drain 40 when the retractable drain 40 is in its extended configuration.

Figure 10:
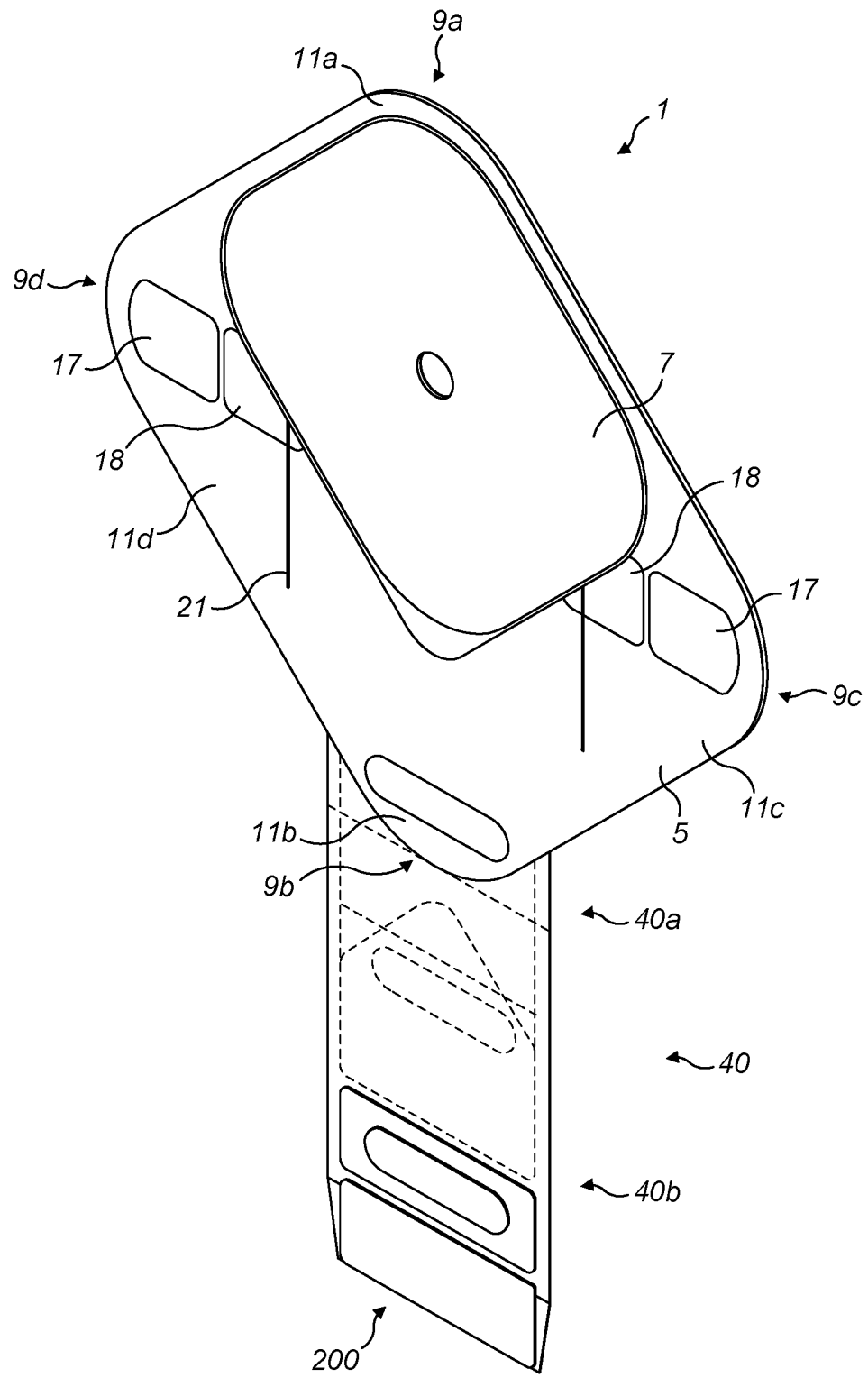
FIG. 10 illustrates a schematic perspective view of another embodiment of ostomy appliance according to the present disclosure in an extended configuration with a closure portion unfastened and unfolded.

The retractable drain 40 is movable between a retracted configuration for storage, as shown in FIG. 17, and the extended configuration, as shown in FIG. 10, for draining stomal output from the cavity. In the retracted configuration the retractable drain 40 may be accommodated within the periphery of the main body portion 2*a* of the inner wall 2 and/or the main body portion 3*a* of the outer wall 3 and/or the one or more comfort layers 5, 6. The retractable drain 40 may be accommodated within a void space between the main body portion 2*a* of the inner wall 2 and the inner comfort layer 5 or between the main body portion 3*a* of the outer wall 3 and the outer comfort layer 6. Movement of the retractable drain 40 into the retracted configuration will be described in more detail below.

The retractable drain 40 may comprise a lower section 40*a* and an upper section 40*b* as shown in FIG. 14.

The retractable drain 40 may comprise a closure portion 202 which may comprise a part of the lower section 40*a* of the retractable drain 40. The closure portion 202 may comprise a section of the retractable drain 40 which extends up from the outlet opening 200 to an upper limit 203*c* as shown in FIG. 15. The length of the closure portion 202 may be from one-third to one-half of the length of the retractable drain 40.

The closure portion 202 may be configured to be folded or otherwise turned up on itself to close off the outlet opening 200 while the retractable drain 40 is in the extended configuration.

The closure portion 202 may be folded into a plurality of segments having approximately equal segment lengths and separated by folds. The closure portion 202 may therefore be successively folded one or more times such that the segments overlie each other. Preferably, the closure portion 202 may be configured to be folded to form a plurality of folds across the width of the retractable drain 40 to inhibit and preferably prevent passage of stomal output out of the outlet opening 200. For example, the segments and fold lines may have appropriate lengths and locations respectively such that the closure portion 202 can be folded or rolled repeatedly in the same sense, folding forwards and upwards towards the upper end of the retractable drain 40 with each fold. The folds may be generally perpendicular to an elongate axis 204 of the retractable drain 40 and extend across the whole width of the retractable drain 40 to close off the drain passage at each fold location.

Passage of stomal output through the closure portion 202 may initially be inhibited by folding the lip 201 over to close the outlet opening 200 of the retractable drain 40.

One or more pursing strips 209-211 may be provided on the closure portion 202. The pursing strips 209-211 may function to both provide localised rigidity to the retractable drain 40 and also to define the locations and orientations of the segments and folds of the closure portion 202.

The pursing strips 209-211 may comprise strips of material attached to the retractable drain 40. The pursing strips 209-211 may be formed from a material, preferably a flexible material, having a higher rigidity than the material of the retractable drain 40 and having some resilience such that once attached to the retractable drain 40 the pursing strips 209-211 can each be squeezed laterally to arch the pursing strip (and therefore the attached drain material) and thereby open the elongate drain passage.

As shown in FIGS. 14 and 15, a first pursing strip 209 may be attached to the inner drain portion 41. A second pursing strip 210 may be attached to the outer drain portion 42. A lip pursing strip 211 may be attached to the inner drain portion 41 below the first pursing strip 209 and adjacent to the outlet opening 200 of the retractable drain 40. Preferably, the lip pursing strip 211 may be arranged on the lip 201.

As shown in FIG. 14, a longitudinal gap 220 may be provided between a lower edge of the first pursing strip 209 and an upper edge of the lip pursing strip 211. The longitudinal gap 220 may define the location of a first fold 202a of the closure portion 202.

The first and second pursing strips 209, 210 may be positioned at the same point along the retractable drain 40 such that they are arranged directly opposite each other. They may therefore be laterally squeezed together to form a pair of opposing arcs, opening the drain passage to facilitate flow of the stomal output through the elongate drain passage.

Preferably, each of the pursing strips 209-211 may extend the same distance along a length of the retractable drain 40.

A first fastener 203 may be used to fasten the closure portion 202 in place in its folded state. The first fastener 203 may be arranged on the retractable drain 40, adjacent to or overlapping the closure portion 202.

As shown in FIG. 15, the first fastener 203 may comprise a first flange 203a and a second flange 203b. The second flange 203b may extend from the first flange 203a, the first flange 203a and the second flange 203b may be one integral piece and may meet at a fold line such that the second flange 203b is rotatable about the fold line.

The first flange 203a may be attached to the retractable drain 40 while the second flange 203b hangs free of the retractable drain 40. The first flange 203a may extend across the width of the retractable drain 40 and be attached to the retractable drain 40 at an attachment point, line or zone. The first flange 203a may be attached within an upper region of the closure portion 202. An upper limit of the attachment point, line or zone may coincide with the upper limit 203c of the closure portion 202. The attachment of the first flange 203a may preferably be formed using an adhesive or by welding.

The fold line between the first flange 203a and the second flange 203b may be located coincident with the upper limit 203c. The second flange 203b may be a free flange (i.e. may be unattached to the retractable drain 40 except by its connection to the first flange 203a). When folded down, the second flange 203b may extend from the upper limit 203c towards the outlet opening 200 such that it extends over the closure portion 202.

The first fastener 203 may include a pull tab 203d for gripping by the user to slide the retractable drain 40 from the retracted configuration to the extended configuration. In the illustrated embodiment, a free end of the second flange 203b may comprise the pull tab 203d.

The second flange 203b may comprise a first fastening element 212a for attachment to a corresponding second fastening element 212b arranged on the closure portion 202. The second fastening element 212b may be attached to the inner drain portion 41 or the first pursing strip 209, such that after the closure portion 202 is folded upwards to close the outlet opening 200, the second fastening element 212b is arranged on an outer face of the retractable drain 40 for fastening to the first fastening element 212a. The first fastening element 212a and the second fastening element 212b may comprise any suitable fastener elements, for example hook-and-loop type fastener elements.

The first fastener 203 may be formed from a flexible sheet material. The flexible sheet material may be more rigid than the flexible sheet material of the inner drain portion 41 and/or the outer drain portion 42.

As described above, the closure portion 202 may comprise a plurality of segments, the segments having approximately equal segment lengths and being separated by fold lines. The length of the second flange 203b may be longer than one segment length but shorter than two segment lengths such that when the closure portion 202 is unfolded, the pull tab 203d does not extend to or beyond the outlet opening 200 of the retractable drain 40 and when the closure portion 202 is folded, the pull tab 203d extends beyond a distal end 214 of the folded retractable drain 40 as shown in FIG. 18b.

The ostomy appliance 1 may further comprise a guide panel 206 and a push element 207 to assist in movement of the retractable drain 40 between its extended and retracted configurations.

Figure 11:
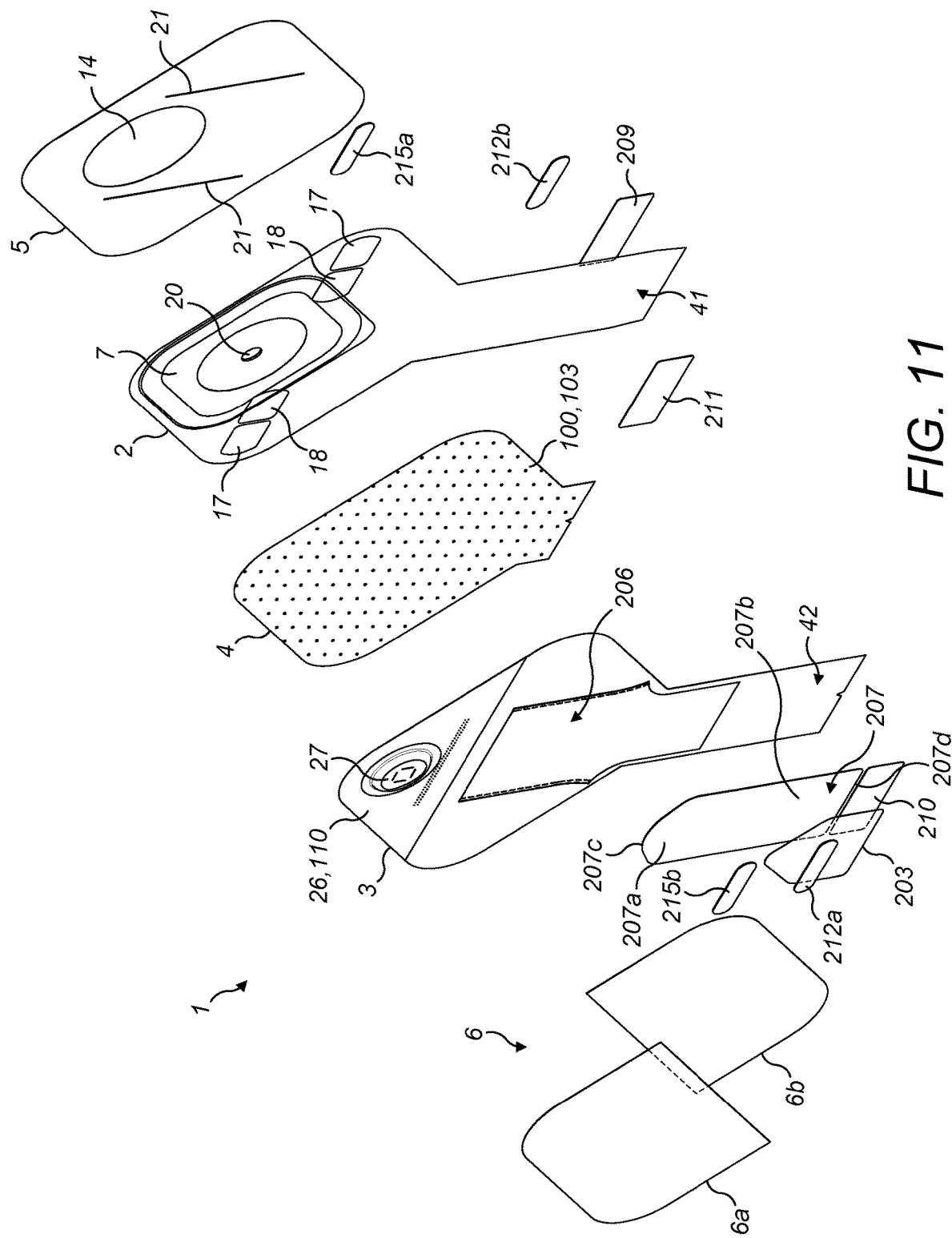
FIG. 11 illustrates a schematic exploded perspective view of components of the ostomy appliance of FIG. 10.

As shown in FIG. 11, the guide panel 206 may be arranged on the outer wall 3. The guide panel 206 may comprise flexible sheet material. The material may be the same as the flexible sheet material of the inner wall 2 and/or the outer wall 3.

As shown in FIG. 13, the guide panel 206 may comprise an upper portion 206a which may be arranged on the main body portion 3a of the outer wall 3 and a lower portion 206b which may extend down from the upper portion 206a to overlie an upper region of the retractable drain 40.

The upper portion 206a may have an upper section 206c extending down from an upper edge of the guide panel 206 of uniform width and a lower section 206d which is flared in that its width increases compared to the uniform width of the upper section 206c. The upper section 206c may transition smoothly into the lower section 206d as shown in FIG. 14 such that lateral edges 213a and 213b of the upper portion 206a may each have the form of a straight edge with a smoothly outwardly-curved lower end.

The lower portion 206b may have a lower section 206f extending up from a lower edge of the guide panel 206 of uniform width and an upper section 206e which is flared in that its width increases compared to the uniform width of the lower section 206f. The lower section 206f may transition smoothly into the upper section 206e as shown in FIG. 15 such that lateral edges 213c and 213d of the lower portion 206b may each have the form of a straight edge with a smoothly outwardly-curved upper end.

The lateral edges 213a, 213b of the upper portion 206a may meet the lateral edges 213c, 213d of the lower portion 206b at apexes 213e and 213f.

The upper portion 206a of the guide panel 206 may be attached to the outer face of the outer wall 3 along the lateral edges 213a, 213b of the upper portion 206a. The attachment may be formed by any suitable means, for example by welding or using an adhesive. The upper portion 206a of the guide panel 206 may be positioned to overlie the cavity when viewed from the front (as arranged when the ostomy appliance 1 is being worn).

The lateral edges 213c, 213d of the lower portion 206b are preferably not attached to the retractable drain 40 along all, or a majority of their length.

The upper portion 206a may define a channel 205 between the upper portion 206a of the guide panel 206 and the outer wall 3. The channel 205 may therefore be arranged outside the cavity. The sides of the channel 205 may be demarcated by the attachment of the lateral edges 213a, 213b. A lowermost point of the lateral edges 213a, 213b may define a location of a mouth 205a of the channel 205 as shown in FIG. 14. The mouth 205a may be located at the transition point between the upper portion 206a and the lower portion 206b of the guide panel 206. For example the mouth 205a may be located at the level of the lowermost point of attachment of the upper portion 206a of the guide panel 206 to the outer wall 3. In particular, the mouth 205a may be located at the level of the apexes 213e and 213f as shown in FIG. 14.

The guide panel 206 as a whole may be aligned with the elongate axis 204 of the retractable drain 40 and the upper portion 206a may have a length selected such that the channel 205 has a length sufficient to receive and retain greater than 50% of, optionally greater than 75%, optionally greater than 90%, optionally substantially all of the length of the retractable drain 40 when the retractable drain 40 is in the retracted configuration.

The channel 205 may have a constant width along a majority of its length. This channel width may be marginally wider than the width of the retractable drain 40, such that at least a portion of the retractable drain 40 may in use be slidingly received in the channel 205, with limited lateral movement. For example, the channel 205 may be 2 to 5 mm wider than external width of the retractable drain 40, typically 2 to 3 mm wider. The retractable drain 40 may thereby be constrained to move into the channel 205 in a direction substantially parallel with the elongate axis 204.

As shown in FIG. 11, the push element 207 may comprise an elongate strip of sheet material having higher rigidity than the flexible sheet materials of the inner wall 2, the outer wall 3 and/or the guide panel 206. The push element 207 may be a generally planar.

The push element 207 may comprise an upper section 207a and a lower section 207b. The upper section 207a may have a rounded upper edge 207c. The lower section 207b may have a straight lower edge 207d. On assembly of the ostomy appliance 1, the upper section 207a may be slidingly received in the channel 205 and the lower section 207b may be fixedly attached to the lower section 40a of the retractable drain 40 and/or the lower portion 206b of the guide panel 206 as explained further below.

The width of the push element 207 may be the same or less than the width of the retractable drain 40 and therefore may have a width narrower than the constant width of the channel 205 such that the push element 207 may be slidingly received in the channel 205. The width of the push element 207 may be 85 to 100% of the width of the retractable drain 40. The width of the channel 205 may thereby restrict lateral movement of the push element 207 as it moves into the retracted configuration and ensure that it moves in line with the elongate axis 204.

The lower section 207b of the push element 207 may be attached to the retractable drain 40, in particular to the lower section 40a of the retractable drain 40 and preferably to the outer drain portion 42 of the outer wall 3. Preferably the push element 207 is only attached to the retractable drain 40 at the lower section 207b. The push element 207, for example the lower section 207b thereof, may be attached to the retractable drain 40 at an attachment 207e as shown in FIG. 15. The attachment 207e may be a point, line or zone of attachment. The attachment 207e may use, for example, adhesive or welding. The attachment 207e may extend over a majority or a whole of the lower section 40a of the retractable drain 40.

An upper limit 208a of the attachment 207e may be located at an intermediate point of the retractable drain 40 which may be the intersection between the upper section 40b and the lower section 40a of the retractable drain 40. For example, the upper limit 208a may be located approximately half-way along the length of the retractable drain 40 when the retractable drain 40 is in the extended configuration with the closure portion 202 folded and fastened.

The attachment 207e is preferably in the form of an attachment zone extending across all or substantially all of the width of the push element 207 from the upper limit 208a of the attachment 207e to the lower edge 207d of the lower section 207b of the push element 207. The whole face of the lower section 207b may be attached to the retractable drain 40.

Once assembled and in the extended configuration, the upper section 207a of the push element 207 may extend upwards from the upper limit 208a of the attachment 207e to be slidingly received in the channel 205 wherein the rounded upper edge 207c of the push element 207 extends through the mouth 205a of the channel 205 sliding between the outer wall 3 and the guide panel 206.

The upper section 207a is preferably unattached to the retractable drain 40. The upper limit 208a may therefore represent the uppermost position on the retractable drain 40 at which the push element 207 is attached to the retractable drain 40 (when the retractable drain 40 is in the extended configuration). The upper section 207a may have a length configured to be long enough such that at least a part of the upper section 207a is still received in the channel 205 when the retractable drain 40 is in the extended configuration.

The first fastener 203 may be directly attached, for example using adhesive, to the push element 207, preferably to the lower section 207b of the push element 207. As noted above, the push element 207 may be directly attached to the outer drain portion 42 of the outer wall 3. The first fastener 203 may thereby be indirectly attached to the outer wall 3.

The first fastener 203 and the push element 207 may be arranged such that the first fastener 203 is operable to fasten the closure portion 202 in a folded or otherwise turned-up state when the retractable drain 40 is in the extended configuration. The first fastener 203 may be arranged to hang below the upper limit 208a of the attachment 207e of the push element 207 to the retractable drain 40. The fastening of the first fastener 203 may therefore be independent of the position of the upper section 207a of the push element 207 in the channel 205. The first fastener 203 may thereby be configured to be operable independently of the position of the push element 207. The first fastener 203 and the push element 207 may be formed as separate components. In particular, this enables the fastening and unfastening of the first fastener 203 when the retractable drain 40 is in the extended configuration.

The lower portion 206b of the guide panel 206 may be attached to the retractable drain 40 at an intermediate location along the retractable drain 40. Additionally or alternatively, as shown in FIG. 18b, the lower portion 206b of the guide panel 206 may be attached to the lower section 207b of the push element 207 which, as noted above, may itself be attached to the retractable drain 40.

Figure 18A:
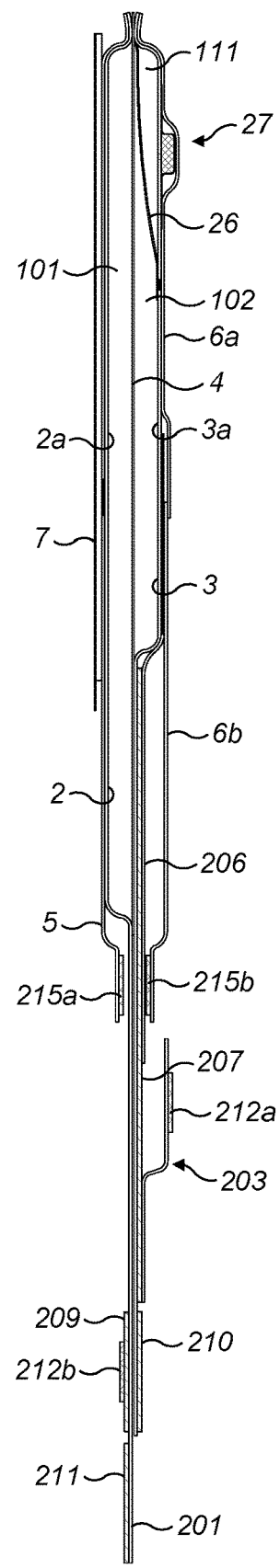

The lower portion 206b, for example a lower end thereof, may be attached to the retractable drain 40 and/or the push element 207 at an attachment 207f as shown in FIG. 18b. The attachment 207f may be a point, line or zone of attachment. The attachment 207f may use, for example, adhesive or welding. Note, the attachments 207e and 207f are shown schematically in FIG. 18b but omitted, for clarity, from FIGS. 18a and 18c.

An upper limit 208b of the attachment 207f may be located at an intermediate point of the retractable drain 40. For example, the upper limit 208b may be located approximately half-way along the length of the retractable drain 40 when the retractable drain 40 is in the extended configuration with the closure portion 202 folded and secured. The attachment 207f may be positioned opposite the location of the attachment 207e.

The lower portion 206b of the guide panel 206 may thereby act as a tether, preventing movement of the push element 207 fully out of the channel 205 on extension of the retractable drain 40. The attachment 207f may preferably extend across the width of the retractable drain 40 and/or the push element 207, thereby assisting in maintaining the alignment of the retractable drain 40 and push element 207 within the channel 205 during retraction of the retractable drain 40.

The lower section 207b of the push element 207 may overlap the closure portion 202 of the retractable drain 40. The overlap may have a length which is the same as or longer than the length of a fold segment of the closure portion 202. As shown in FIG. 15, a longitudinal gap 221 may be provided between the lower edge 207d of the push element 207 and an upper edge of the second pursing strip 210. The longitudinal gap 221 may define the location of a second fold 202b of the closure portion 202.

Therefore, once the closure portion 202 is folded, the segments of the closure portion 202 below the second fold 202b may overlie the lower section 207b of the push element 207, and the lower edge 207d of the push element 207 may be arranged adjacent the distal end 214 of the folded retractable drain 40.

The functioning of the retractable drain 40 will now be described starting with the retractable drain 40 in the extended configuration as shown in FIGS. 10 to 15.

Figure 16A:
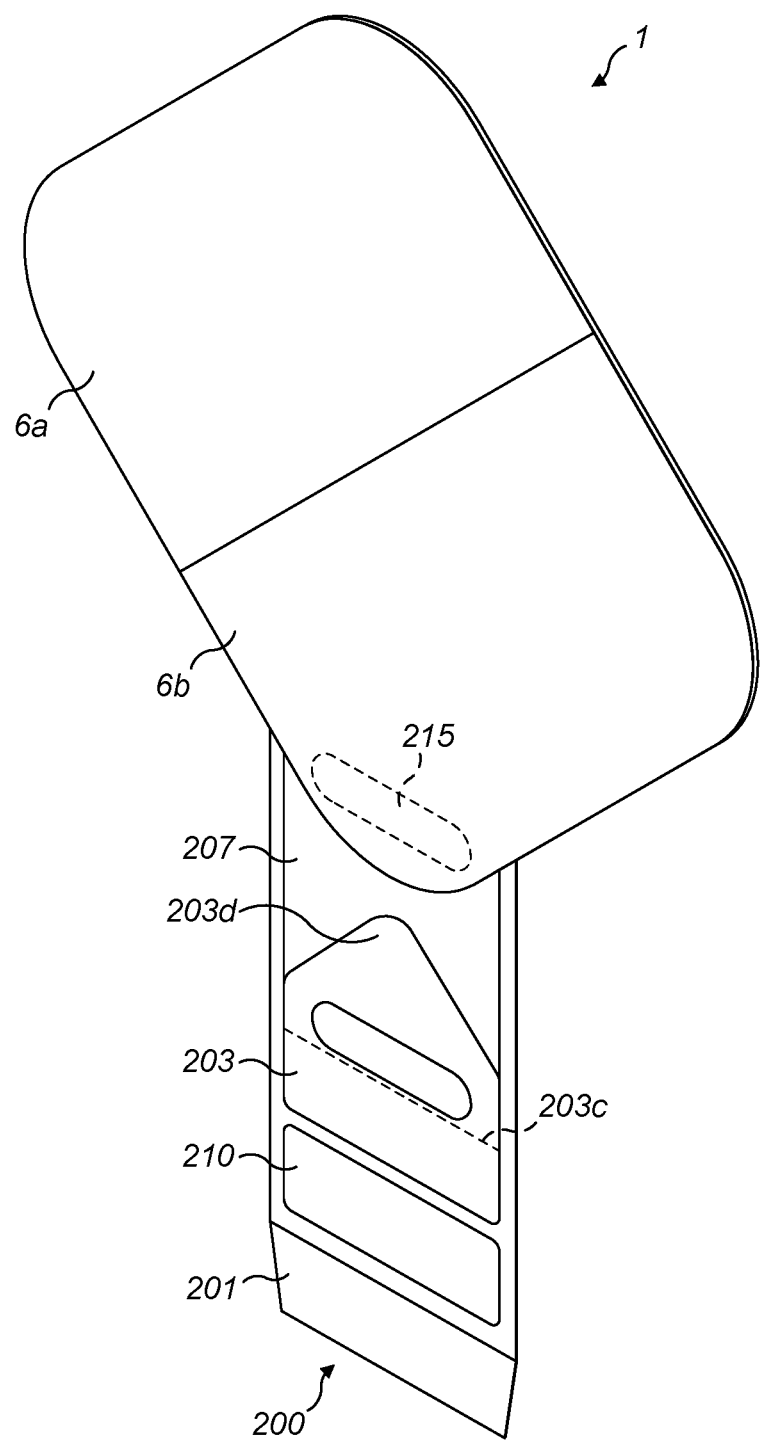
FIGS. 16a to 16d schematically illustrate the retractable drain of the ostomy appliance of FIG. 10 in a) the extended configuration b) the extended configuration with the closure portion folded c) the extended configuration with the closure portion folded and fastened and d) the retracted configuration.

In the extended configuration, as shown in FIGS. 16a and 18a, the retractable drain 40 may extend through the opening 130 and the retractable drain 40 and its closure portion 202 may be entirely unfolded such that stomal output may move from the cavity down the elongate drain passage of the retractable drain 40 and out of the outlet opening 200. Passage of the stomal output out of the outlet opening may be facilitated by pressing on the pursing strips 209-211 to hold open the outlet opening 200 and/or to curve the lip 201 into a chute shape to guide the exiting flow of stomal output.

Figure 16B:
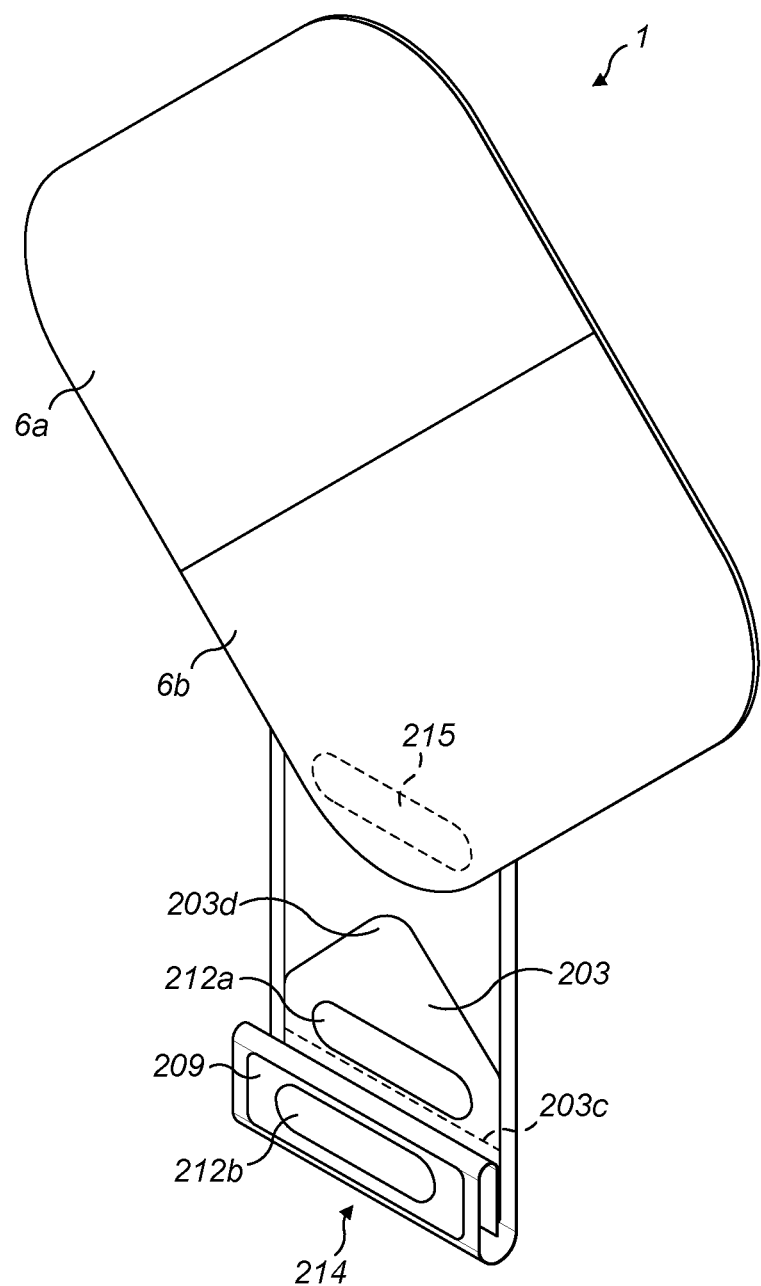
Figure 16C:
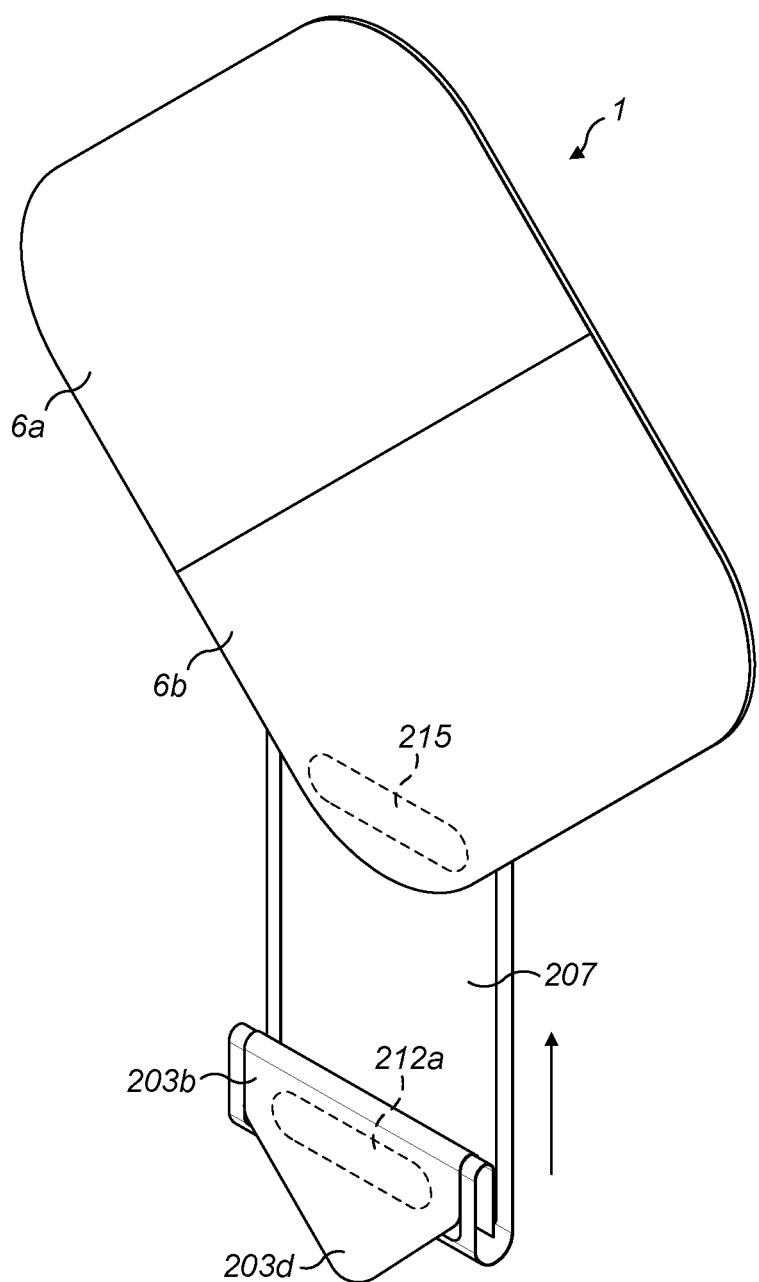
Figure 16D:
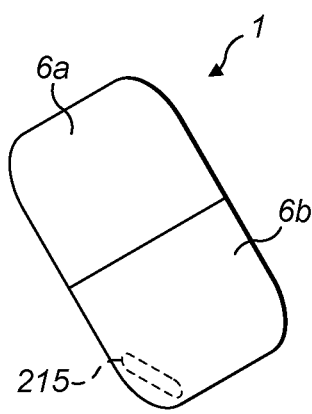

After emptying the cavity, the outlet opening 200 may be sealed to prevent flow of stomal output out of the retractable drain 40. As shown in FIGS. 16 to 18, with the retractable drain 40 in the extended configuration, the outlet opening 200 may first be sealed by operation of the closure portion 202 which may be folded over at least once, and preferably a plurality of times. For example, the lip 201 may first be folded upwards about the first fold 202a to overlie the first pursing strip 209. Next the lip 201 and the next segment bearing the first pursing strip 209 and second pursing strip 210 may be folded upwards, about the second fold 202b to overlie the first flange 203a and lower section 207b of the push element 207 as shown in FIG. 16b. The second flange 203b of the first fastener 203 may then be folded over to fasten the closure portion 202 in its folded position by securing together the first and second fastening element 212a, 212b as shown in FIG. 16c. The user may then, if desired, let go of the retractable drain 40 if needed without stomal output being released through the outlet opening 200.

To move the retractable drain 40 into the retracted configuration after folding and fastening of the closure portion 202, the user may grip the folded and fastened end of the retractable drain 40 and push upwards such that the push element 207 moves further up into the channel 205 as shown in FIG. 18b.

Movement of the push element 207 may be used to create one more folds in the retractable drain 40 so as to shorten its length in the retracted configuration and to close off the elongate drain passage.

Due to the attachment 207e between the push element 207 and the outer drain portion 42, the resulting upward movement of the push element 207 causes the lower section 40a of the retractable drain 40 to be carried up and the unattached upper section 40b of the retractable drain 40 to start to bend away from the push element 207 as shown in FIG. 18b resulting in the formation of a first fold 216 and a second fold 217 in the retractable drain 40.

As the push element 207 moves up the second fold 217 will start to form at the location of the upper limit 208a since the upper section 40b is unattached to the push element 207 and is thus free to move away therefrom. The associated first fold 216 forms intermediate the upper end of the retractable drain 40 and the second fold 217 as shown in FIGS. 18b and 18c.

At the same time upward movement of the push element 207 may likewise cause the formation of a first fold 218 and a second fold 219 in the lower portion 206b of the guide panel 206 as shown in FIG. 18b. The second fold 219 will start to form at the location of the upper limit 208b since lower portion 206b above the upper limit 208b is unattached to the push element 207 and is thus free to move away therefrom. The associated first fold 218 forms intermediate the upper end of the lower portion 206b and the second fold 219 as shown in FIG. 18b.

Continued upward movement of the push element 207 may thus cause the retractable drain 40 to double back on itself and the lower portion 206b of the guide panel 206 to double back on itself.

In the fully retracted configuration as shown in FIG. 18c, the retractable drain 40 may comprise a generally Z-shaped form by virtue of the fully formed first fold 216 and second fold 217.

The first fold 216 and the second fold 217 preferably extend fully across the retractable drain 40 such that the first and second folds 216, 217 close off the elongate drain passage and inhibit drainage of stomal output through the retractable drain 40. As can be seen in FIG. 18c, the lower end of the separation wall 4 extends below the final location of the first fold 216 such that the second fold 216 may effectively seal of the lower end of the first and second chambers 101, 102 when the retractable drain 40 is in its retracted configuration.

The first and second folds 216, 217 may be folded in opposite senses such that the upper section 40b of the retractable drain 40 overlies the cavity adjacent to the main body portion 3a of the outer wall 3 and the lower section 40a of the retractable drain 40 overlies the upper section 40b, such that all of the retractable drain 40 directly or indirectly overlies the main body portion 3a of the outer wall 3.

In the retracted configuration, the first fold 216 may have rolled up the upper section 40b of the retractable drain 40 to be located at or adjacent the drain inlet 45. The second fold 217 may be located approximately halfway along the length of the retractable drain 40 such that in the retracted configuration the distal end 214 of the retractable drain 40 (with the closure portion 202 folded) is arranged adjacent to the first fold 216 as shown in FIG. 18c.

The channel 205 may have a depth between the guide panel 206 and the outer wall 3 configured such that the retractable drain 40 is a tight sliding fit in the channel 205 in the depth direction when the retractable drain 40 is in the retracted configuration.

The folds 216, 217 formed in the retractable drain 40 as it moves into the retracted configuration may thereby be formed generally perpendicular to the length of the retractable drain 40. This may also assist in ensuring that greater than 50% of, optionally greater than 75%, optionally greater than 90%, optionally substantially all of the length of the retractable drain 40 (with the closure portion 202 folded) may be received within the channel 205 in the retracted configuration.

The channel 205 of the upper portion 206a of the guide panel 206 may have a length which is at least half the length of the retractable drain 40 when the retractable drain 40 is in the extended configuration with the closure portion 202 folded. Preferably, the channel 205 may have a length marginally longer than the length of the push element 207 such that a majority of or substantially all of the push element 207 may be received in the channel 205 in the retracted configuration.

Further example embodiments of an ostomy appliance 1 according to the present disclosure are described below. Only those features that differ in this embodiment compared to the previous embodiments will be described in detail in the following description. For features that are common to one or more embodiments, reference should be made to the description as a whole.

Figure 19A:
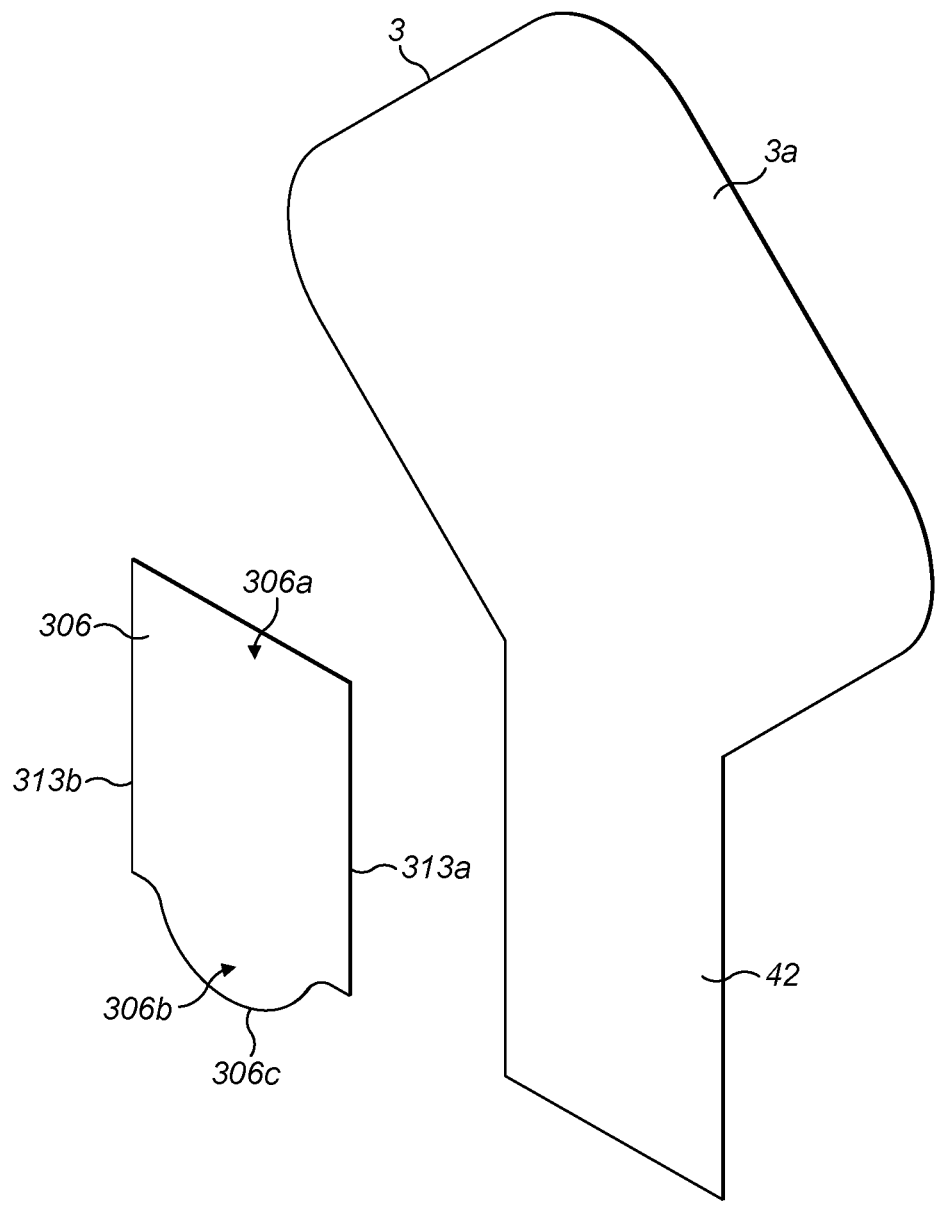
FIGS. 19a and 19b illustrate a schematic views of a another embodiment of ostomy appliance according to the present disclosure with a retractable drain in an extended configuration.
Figure 19B:
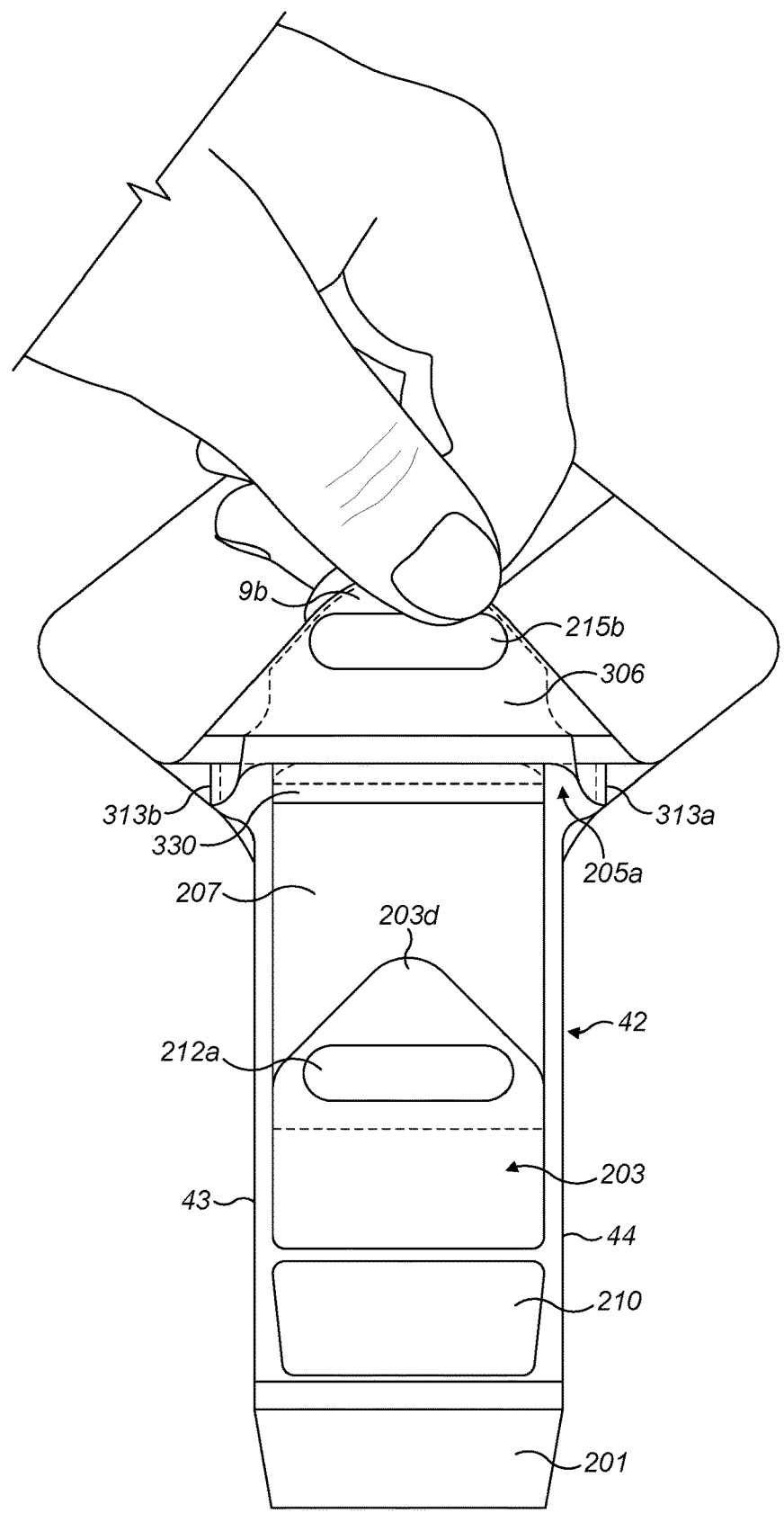

In any embodiment, the lower portion 206b of the guide panel 206 may take a different form to that shown in FIGS. 10 to 18. An alternative form of guide panel is shown in FIGS. 19a and 19b. The guide panel 306 may comprise an upper portion 306a defining the channel 205 as in the embodiment of FIGS. 10 to 18 demarcated between lateral edges 313a and 313b of the upper portion 306a. The mouth 205a of the channel 205 may be located at the transition point between the upper portion 306a and the lower portion 306b of the guide panel 306.

The lower portion 306b of the may have a lower edge 306c shaped such that it does not extend outside the outer comfort layer 6 in use. The lower portion 306b may therefore have a truncated shape compared to the lower portion 206b of guide panel 206. The lower edge 306c may be shaped to match the curve of the lower apex of the outer comfort layer 6. The lower portion 9b may be attached to the lower apex of the outer comfort layer 6, for example by use of adhesive or by welding, at or adjacent to the opening 130 of the comfort layer. Opening of the closure 215 to open opening 130 may tend to open out the mouth 205a of the channel 205, facilitating extension and retraction of the retractable drain 40 in use.

The lower portion 306a may be unattached to the drain 40. A separate tether may be provided for tethering the push element 207 in the channel 205. The separate tether may be attached to the drain by an attachment 330 formed, for example, by use of adhesive or by welding.

In any embodiment, the outlet opening 200 of the retractable drain 40 may be configured for connection of a night bag or other appliance for receiving stomal output from the retractable drain 40.

Other features of the ostomy appliance, for example the shape and construction of the ostomy appliance inner and outer walls and comfort layer, may vary from those shown in the illustrated embodiment.

In any embodiment, the retractable drain may alternatively be formed as a one-piece tube rather than from two sheets joined by lateral welds. The retractable drain may be integrally formed with the inner wall and/or the outer wall of the appliance. Alternatively, or in addition, one or more parts of the retractable drain may be formed from flexible sheet material or other material separately to the formation of the inner wall and/or the outer wall, and assembled by any suitable means, for example by welding or using adhesives.

The fastening elements illustrated are hook-and-loop type elements. Alternatively, any form of suitable fastener elements may be used (for example, poppers, zippers or adhesives).

The channel may be formed on the inner wall rather than outer wall of the cavity.

The guide panel is preferably formed separately to the comfort layer. Alternatively, the guide panel may comprise a portion of the comfort layer. Alternatively, or in addition, the guide panel may be arranged on the inner wall or the outer wall and attached to the comfort layer instead of or as well as being attached to the wall.

In addition or alternatively to the closure 215 and first fastener 203, alternative means of sealing the outlet opening 200 in the extended configuration may be provided. In any embodiment, the upper limit 208a of the attachment of the push element 207 to the retractable drain 40 may be arranged approximately halfway along the length of the retractable drain 40 with the outlet opening 200 of the drain sealed in the extended configuration.

One or both comfort layers 5, 6 may optionally be omitted or formed from alternative materials to display the outer wall 3 and/or inner wall 2, for example for hospital use.

In the illustrated embodiment, the closure portion 202 is configured to be turned up by folding. Alternatively, or additionally, in any embodiment the closure portion 202 may be turned up by rolling.

Figure 20:
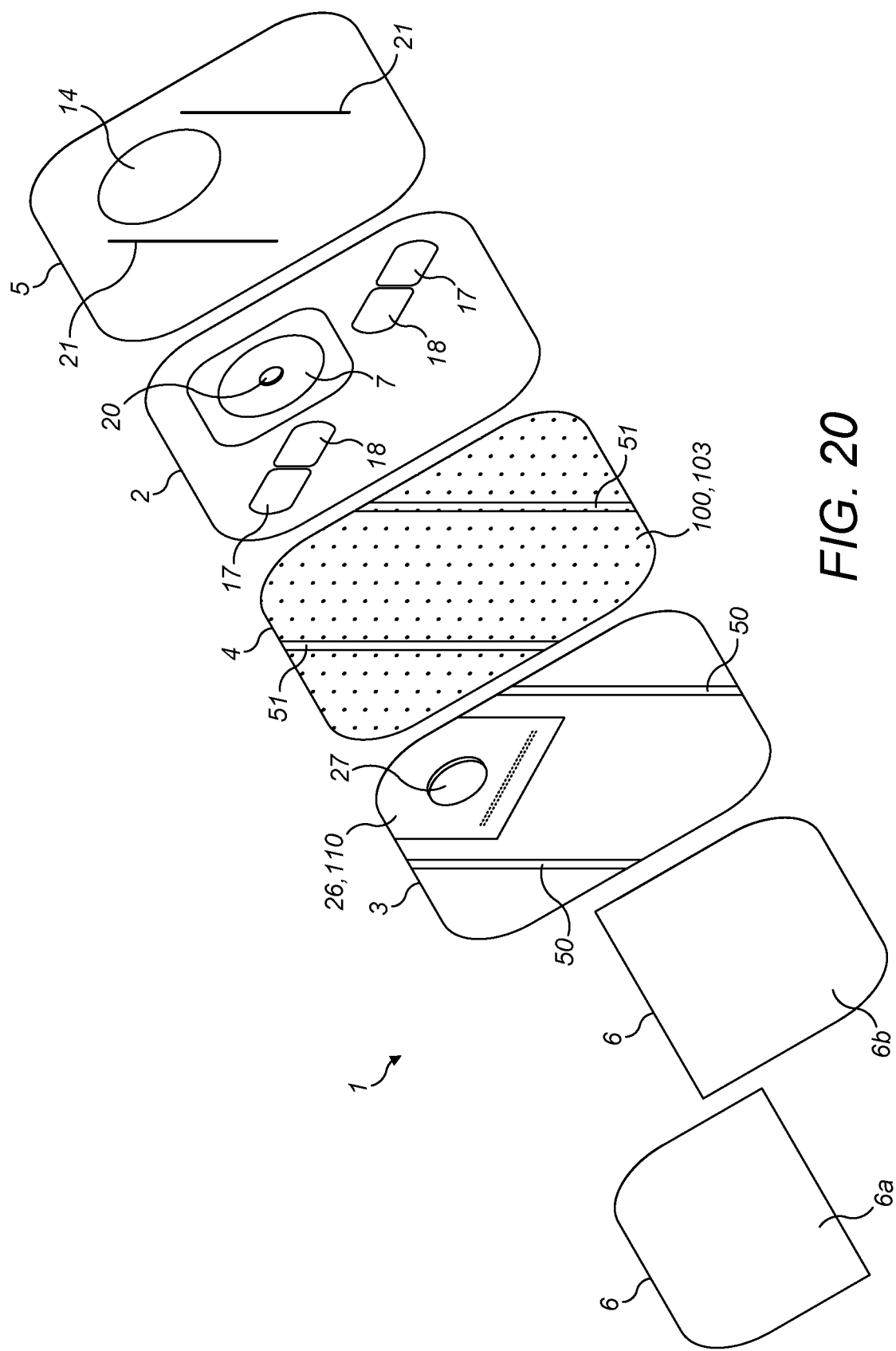
FIG. 20 illustrates an exploded perspective view of another embodiment of ostomy appliance according to the present disclosure.

A further embodiment of an ostomy appliance 1 according to the present disclosure is shown in FIG. 20.

Compared to the first embodiment of ostomy appliance 1, one or more components of the ostomy appliance 1 may be provided with one or more pleats to permit, enhance, control and/or configure expansion of the ostomy appliance 1 as the cavity fills with the stomal output. As shown in FIG. 20, the outer wall 3 may be provided with one or more pleats 50 which are configured to partially or fully unfold as the cavity receives the stomal output to promote conformation of the inner wall 2 against a body of an ostomate wearing the ostomy appliance 1.

Each pleat 50 may comprise one or more folds of the flexible sheet material of the outer wall 3. Each pleat 50 may comprise a generally Z-shaped form having two distinct folds. The one or more pleats 50 may be configured to partially or fully unfold as the cavity receives the stomal output to promote displacement of a first apex and a second apex towards the body of the ostomate. In some embodiments, the first apex and the second apex are the opposed lateral apexes 9c, 9d and the conformation of the inner wall 2 involves an improved conformation of the inner wall 2 to a torso of the ostomate.

The inner wall 2 may be free of pleats. This may assist in promoting conformation of the inner wall 2.

In some embodiments the one or more pleats 50 comprise two pleats 50 which are arranged symmetrically about a vertical midline of the outer wall 3 as shown in FIG. 16. The pleats 50 may be aligned with the fold lines 16c-d of the inner wall 2 and the outer wall 3.

The one or more pleats 50 may each be 5 to 8 mm in width.

Additionally or alternatively, as shown in FIG. 20, the separation wall 4 may be provided with one or more pleats 51 which are configured to partially or fully unfold as the cavity, particularly the first chamber 101, receives the stomal output to promote conformation of the inner wall 2 against a body of an ostomate wearing the ostomy appliance 1. The one or more pleats 51 may have the same design and construction as the one or more pleats 50. The one or more pleats 51 may comprise two pleats 51 which are arranged symmetrically about a vertical midline of the separation wall 4 as shown in FIG. 20. The pleats 51 may be aligned with the fold lines 16c-d of the inner wall 2 and the outer wall 3 as well as the pleats 50 of the outer wall 3.

In some embodiments a free edge of the inner wall 2 and/or a free edge of the outer wall 3 and/or a free edge of the separation wall 4 may be joined by a peripheral weld 8 and the peripheral weld 8 may comprise an enhanced weld zone in the vicinity of each of the one or more pleats 50 of the outer wall 3 and/or the one or more pleats 51 of the separation wall 4. In one example the enhanced weld zone comprises a weld of increased thickness compared to the peripheral weld 8 outside the enhanced weld zone. It may be preferred that an upper end and a lower end of each of the one or more pleats 50 of the outer wall 3 and/or the one or more pleats 51 of the separation wall 4 is traversed by one of the enhanced weld zones.

In examples where the outer wall 3 comprises one or more pleats 50 which are configured to partially or fully unfold as the cavity receives the stomal output, the first part 6a and the second part 6b of the outer comfort layer 6 may be configured to slide over each other in the overlap region 15 to accommodate expansion of the underlying outer wall 3.

The first part 6a and the second part 6b may be joined to each other at a first end and at a second end of the overlap region 15. In some embodiments the first part 6a and the second part 6b are welded to each other at the first end and at the second end of the overlap region 15, preferably as part of the peripheral weld 8.

These beneficial effects may be further increased by the provision of the one or more pleats 50 in the outer wall 3 as discussed above.

EXAMPLES

The following table presents example configurations of an ostomy appliance 1 according to the present disclosure. These examples are not intended to be limiting on the present disclosure in any way or to limit the scope of the appended claims. Rather, the examples are provided to aid a better understanding of the present disclosure.

The examples refer to features described in further detail elsewhere in the present disclosure. The skilled reader will understand that reference should be made to said further description where necessary for a fuller understanding of the examples. Where said further description refers to optional characteristics of said features then the skilled reader will understand that the following examples may optionally also include one or more of said optional characteristics.

General Construction

In the following examples in the table, the ostomy appliance 1 is a one-piece ostomy appliance 1 wherein the ostomy wafer 7 is permanently attached to the ostomy appliance 1, to the extent that the ostomy wafer 7 cannot easily be separated without risk of damaging the ostomy appliance 1. However, as noted above the teachings of this disclosure may also be applied, with suitable alteration where necessary, to two-piece appliances. The ostomy appliance 1 of the following examples is particularly suited as an ileostomy appliance but is not limited to this function.

In the following examples in the table, the ostomy appliance 1 comprises an inner wall 2 and an outer wall 3 which are diamond-shaped having four apexes—an upper apex 9a which points generally vertically upwards, a lower apex 9b which points generally vertically downwards and opposed lateral apexes 9c, 9d which point generally to each side. In examples where a retractable drain 40 is present this extends from the lower apex 9b. The apexes 9a-9d are rounded with a radius of curvature of about 30 mm.

In the following examples in the table, the inner wall 2 and the outer wall 3 comprise a left lateral wing region 11d terminating in lateral apex 9d and a right lateral wing region 11c terminating in lateral apex 9c. As described above, the lateral wing regions 11c, 11d are foldable about fold lines 16c, 16d to overlie adjacent regions 12c, 12d in a folded configuration of the ostomy appliance 1.

In this table, the term "Wall Size" refers to the length of the sides of the inner wall 2 and the outer wall 3. The 'length' is measured as the perpendicular distance between opposite sides of the inner wall 2/outer wall 3. In the following examples in the table the length of each side is the same, i.e. the inner wall 2 and the outer wall 3 are generally square-shaped but with rounded corners as noted above.

In this table, the term "Separation Filter" refers to whether a separation wall 100 as described above is present. The separation wall 100, where present, is located between the inner wall 2 and the outer wall 3. The separation wall 4 comprises a separation filter 100 for filtering stomal gases and/or stomal liquids from stomal solids contained in the stomal output.

The inner wall 2 and outer wall 3 are formed from EVA/PVdC multi-layered film of 75 micrometres thickness. The separation wall 100 (where present) is formed from PE film of 51 micrometres thickness or EVA (with 4.5% VA) film of 50 micrometres thickness.

The following examples may comprise at least an inner comfort layer 5 as described above that comprises two vertical slits 21 as described above for receiving the lateral apexes 9c, 9d of the inner wall 2 and the outer wall 3 when the ostomy appliance 1 is in its folded configuration.

In this table, the term "Type" refers to the nature of the ostomy appliance: "Closed" refers to an ostomy appliance that does not comprise a drain. "Open" refers to an ostomy appliance that comprises a drain. The drain may be a retractable drain. The retractable drain may be a retractable drain 40 as described above.

In this table, the term "Wafer Size" refers to the length of the sides of the ostomy wafer 7. The 'length' is measured as the perpendicular distance between opposite sides of the ostomy wafer. In the following examples in the table the length of each side is the same, i.e. the ostomy wafer 7 is square-shaped but with rounded corners as shown in the appended figures.

In this table, the term "Wafer Type" refers to the configuration of the ostomy wafer 7: "Flat" refers to an ostomy wafer 7 that is flat in shape. "Convex" refers to an ostomy wafer 7 that is convex in shape. "Flexible" refers to an ostomy wafer 7 that is flexible.

In this table, the term "Wafer Aperture Type" refers to the nature of the aperture in the ostomy wafer 7: "Pre-Cut" refers to the presence of a pre-formed aperture in the ostomy wafer 7 for engaging in, on, over or against the stoma of an ostomate. "Cut-To-Fit" refers to an ostomy wafer 7 configured to allow an ostomate to cut an aperture therein for engaging in, on, over or against their stoma. In this way the aperture may be tailored to the specific requirements of each ostomate.

In this table, the term "Aperture Size" refers to the diameter of the pre-formed aperture in the ostomy wafer 7 in the case of a Pre-Cut ostomy wafer and refers to the range of possible aperture diameters that may be formed in the ostomy wafer 7 in the case of a Cut-To-Fit ostomy wafer.

In this table, the column "Colour" refers to the colour of the outermost layer of the ostomy appliance. "Neutral" refers to the presence of an outer comfort layer 6 having an opaque, neutral colour. In these examples the outer wall 3 is transparent and the inner wall 2 is opaque, e.g. white. "Clear" refers to an ostomy appliance without an outer comfort layer 6. In these examples the outermost layer is the outer wall 3 which is transparent. The inner wall 2 is opaque, e.g. white. All examples are provided with an inner comfort layer 5 that is an opaque, neutral colour. By "transparent" is meant a material that is substantially or fully transparent, or sufficiently translucent to permit viewing of the fill-level of the cavity through the outer wall 3.

TABLE

| Example No. | Type | Wafer Type | Wafer Size (mm) | Wafer Aperture Type | Aperture Size (mm) | Wall Size (mm) | Colour | Separation Filter? |
|---|---|---|---|---|---|---|---|---|
| 1 | Closed | Flat | 98 | Cut-To-Fit | 10-50 | 140 | Neutral | Yes |
| 2 | Closed | Flat | 98 | Pre-Cut | 25 | 140 | Neutral | Yes |
| 3 | Closed | Flat | 98 | Pre-Cut | 30 | 140 | Neutral | Yes |
| 4 | Closed | Flat | 98 | Pre-Cut | 35 | 140 | Neutral | Yes |
| 5 | Closed | Flat | 98 | Pre-Cut | 40 | 140 | Neutral | Yes |
| 6 | Closed | Flat | 107 | Cut-To-Fit | 10-60 | 170 | Neutral | Yes |
| 7 | Closed | Flat | 107 | Pre-Cut | 25 | 170 | Neutral | Yes |
| 8 | Closed | Flat | 107 | Pre-Cut | 30 | 170 | Neutral | Yes |
| 9 | Closed | Flat | 107 | Pre-Cut | 35 | 170 | Neutral | Yes |
| 10 | Closed | Flat | 107 | Pre-Cut | 40 | 170 | Neutral | Yes |
| 11 | Closed | Flat | 107 | Cut-To-Fit | 10-60 | 170 | Clear | Yes |
| 12 | Closed | Flat | 107 | Cut-To-Fit | 10-60 | 170 | Clear | No |
| 13 | Open | Flat | 98 | Cut-To-Fit | 10-50 | 140 | Neutral | Yes |
| 14 | Open | Flat | 98 | Pre-Cut | 25 | 140 | Neutral | Yes |
| 15 | Open | Flat | 98 | Pre-Cut | 30 | 140 | Neutral | Yes |
| 16 | Open | Flat | 98 | Pre-Cut | 35 | 140 | Neutral | Yes |
| 17 | Open | Flat | 107 | Cut-To-Fit | 10-60 | 170 | Neutral | Yes |
| 18 | Open | Flat | 107 | Pre-Cut | 25 | 170 | Neutral | Yes |
| 19 | Open | Flat | 107 | Pre-Cut | 30 | 170 | Neutral | Yes |
| 20 | Open | Flat | 107 | Pre-Cut | 35 | 170 | Neutral | Yes |
| 21 | Open | Flat | 107 | Pre-Cut | 40 | 170 | Neutral | Yes |
| 22 | Open | Flat | 107 | Cut-To-Fit | 10-60 | 170 | Clear | Yes |
| 23 | Open | Flat | 107 | Cut-To-Fit | 10-60 | 170 | Clear | No |
| 24 | Open | Flat | 107 | Pre-Cut | 25 | 170 | Clear | Yes |
| 25 | Open | Flat | 107 | Pre-Cut | 30 | 170 | Clear | Yes |
| 26 | Open | Flat | 107 | Pre-Cut | 35 | 170 | Clear | Yes |
| 27 | Open | Flat | 107 | Pre-Cut | 40 | 170 | Clear | Yes |
| 28 | Closed | Convex | 107 | Cut-To-Fit | 10-55 | 170 | Neutral | Yes |
| 29 | Closed | Convex | 107 | Cut-To-Fit | 10-55 | 170 | Clear | No |
| 30 | Open | Convex | 107 | Cut-To-Fit | 10-55 | 170 | Clear | Yes |
| 31 | Open | Convex | 107 | Cut-To-Fit | 10-55 | 170 | Neutral | Yes |
| 32 | Closed | Convex | 98 | Cut-To-Fit | 10-45 | 140 | Neutral | Yes |
| 33 | Closed | Convex | 107 | Cut-To-Fit | 10-45 | 170 | Neutral | Yes |
| 34 | Closed | Convex | 107 | Pre-Cut | 25 | 170 | Neutral | Yes |
| 35 | Closed | Convex | 107 | Pre-Cut | 30 | 170 | Neutral | Yes |
| 36 | Closed | Convex | 107 | Pre-Cut | 35 | 170 | Neutral | Yes |
| 37 | Open | Convex | 98 | Cut-To-Fit | 10-45 | 140 | Neutral | Yes |
| 38 | Open | Convex | 107 | Cut-To-Fit | 10-45 | 170 | Neutral | Yes |
| 39 | Open | Convex | 107 | Cut-To-Fit | 10-45 | 170 | Clear | Yes |

TABLE-continued

| Example No. | Type | Wafer Type | Wafer Size (mm) | Wafer Aperture Type | Aperture Size (mm) | Wall Size (mm) | Colour | Separation Filter? |
|---|---|---|---|---|---|---|---|---|
| 40 | Open | Convex | 107 | Pre-Cut | 25 | 170 | Neutral | Yes |
| 41 | Open | Convex | 107 | Pre-Cut | 30 | 170 | Neutral | Yes |
| 42 | Open | Convex | 107 | Pre-Cut | 35 | 170 | Neutral | Yes |
| 43 | Closed | Convex | 98 | Cut-To-Fit | 10-35 | 140 | Neutral | Yes |
| 44 | Closed | Convex | 107 | Cut-To-Fit | 10-35 | 170 | Neutral | Yes |
| 45 | Closed | Convex | 107 | Pre-Cut | 25 | 170 | Neutral | Yes |
| 46 | Closed | Convex | 107 | Pre-Cut | 30 | 170 | Neutral | Yes |
| 47 | Closed | Convex | 107 | Pre-Cut | 35 | 170 | Neutral | Yes |
| 48 | Open | Convex | 98 | Cut-To-Fit | 10-35 | 140 | Neutral | Yes |
| 49 | Open | Convex | 107 | Cut-To-Fit | 10-35 | 170 | Neutral | Yes |
| 50 | Open | Convex | 107 | Pre-Cut | 25 | 170 | Neutral | Yes |
| 51 | Open | Convex | 107 | Pre-Cut | 30 | 170 | Neutral | Yes |
| 52 | Open | Convex | 107 | Pre-Cut | 35 | 170 | Neutral | Yes |
| 53 | Closed | Convex | 98 | Cut-To-Fit | 10-25 | 140 | Neutral | Yes |
| 54 | Open | Convex | 98 | Cut-To-Fit | 10-25 | 140 | Neutral | Yes |
| 55 | Open | Convex | 107 | Cut-To-Fit | 10-25 | 170 | Neutral | Yes |
| 56 | Closed | Flexible | 107 | Cut-To-Fit | 10-55 | 170 | Neutral | Yes |
| 57 | Closed | Flexible | 107 | Cut-To-Fit | 10-55 | 170 | Clear | No |
| 58 | Open | Flexible | 107 | Cut-To-Fit | 10-55 | 170 | Clear | Yes |
| 59 | Open | Flexible | 107 | Cut-To-Fit | 10-55 | 170 | Neutral | Yes |
| 60 | Closed | Flexible | 98 | Cut-To-Fit | 10-45 | 140 | Neutral | Yes |
| 61 | Closed | Flexible | 107 | Cut-To-Fit | 10-45 | 170 | Neutral | Yes |
| 62 | Closed | Flexible | 107 | Pre-Cut | 25 | 170 | Neutral | Yes |
| 63 | Closed | Flexible | 107 | Pre-Cut | 30 | 170 | Neutral | Yes |
| 64 | Closed | Flexible | 107 | Pre-Cut | 35 | 170 | Neutral | Yes |
| 65 | Open | Flexible | 98 | Cut-To-Fit | 10-45 | 140 | Neutral | Yes |
| 66 | Open | Flexible | 107 | Cut-To-Fit | 10-45 | 170 | Neutral | Yes |
| 67 | Open | Flexible | 107 | Cut-To-Fit | 10-45 | 170 | Clear | Yes |
| 68 | Open | Flexible | 107 | Pre-Cut | 25 | 170 | Neutral | Yes |
| 69 | Open | Flexible | 107 | Pre-Cut | 30 | 170 | Neutral | Yes |
| 70 | Open | Flexible | 107 | Pre-Cut | 35 | 170 | Neutral | Yes |
| 71 | Closed | Flexible | 98 | Cut-To-Fit | 10-35 | 140 | Neutral | Yes |
| 72 | Closed | Flexible | 107 | Cut-To-Fit | 10-35 | 170 | Neutral | Yes |
| 73 | Closed | Flexible | 107 | Pre-Cut | 25 | 170 | Neutral | Yes |
| 74 | Closed | Flexible | 107 | Pre-Cut | 30 | 170 | Neutral | Yes |
| 75 | Closed | Flexible | 107 | Pre-Cut | 35 | 170 | Neutral | Yes |
| 76 | Open | Flexible | 98 | Cut-To-Fit | 10-35 | 140 | Neutral | Yes |
| 77 | Open | Flexible | 107 | Cut-To-Fit | 10-35 | 170 | Neutral | Yes |
| 78 | Open | Flexible | 107 | Pre-Cut | 25 | 170 | Neutral | Yes |
| 79 | Open | Flexible | 107 | Pre-Cut | 30 | 170 | Neutral | Yes |
| 80 | Open | Flexible | 107 | Pre-Cut | 35 | 170 | Neutral | Yes |
| 81 | Closed | Flexible | 98 | Cut-To-Fit | 10-25 | 140 | Neutral | Yes |
| 82 | Open | Flexible | 98 | Cut-To-Fit | 10-25 | 140 | Neutral | Yes |
| 83 | Open | Flexible | 107 | Cut-To-Fit | 10-25 | 170 | Neutral | Yes |

It is to be understood that at least some of the figures and descriptions of the disclosure have been simplified to focus on elements that are relevant for a clear understanding of the disclosure, while eliminating, for purposes of clarity, other elements that the reader skilled in the art will appreciate may also be required. Because such elements are well known to the reader skilled in the art, and because they do not necessarily facilitate a better understanding of the disclosure, a description of such elements is not provided herein.

The invention claimed is:

1. An ostomy appliance comprising a main body portion comprising an inner wall and an outer wall of flexible sheet material joined together to define a cavity for containing a stomal output;
   the inner wall comprising an inlet for receiving the stomal output into the cavity;
   the ostomy appliance further comprises an outer comfort layer overlying at least a portion of the outer wall;
   a separation wall located between the inner wall and the outer wall; and sealed together at an at least upper and side peripheral regions of the separation wall to at least the upper and side peripheral regions of the inner wall and to the outer wall to form a first chamber between the inner wall and separation wall and a second chamber between the separation wall and the outer wall, the separation wall further comprising a separation filter for filtering gases and/or liquids into the second chamber from solid matter contained in the stomal output as contained in the first chamber; and
   a gas vent with a gas filter provided in an upper portion of the outer wall and configured to allow the gases to exit the ostomy appliance,
   wherein the outer comfort layer comprises a first part and a second part which are joined to the outer wall so that the first part partially overlaps the second part in an overlap region, wherein the first part and the second part are separable from each other in the overlap region to form a window opening for viewing the cavity;
   wherein the overlap region is angled obliquely to a horizontal direction when a lower apex is vertically downward relative to an upper apex of the ostomy appliance;
   wherein the outer wall comprises one or more pleats which are configured to partially or fully unfold as the cavity receives the stomal output, the first part and the second part of the outer comfort layer being configured to slide over each other in the overlap region to accommodate expansion of the underlying outer wall;
   wherein the separation filter comprises one or more pleats aligned with the one or more pleats of the outer wall; and wherein the separation filter is configured to prevent at least stomal solids from passing from the first chamber, through the separation wall, into the second chamber, and contacting the gas filter.

2. The ostomy appliance as claimed in claim 1, wherein the window opening extends fully, or substantially fully, across a face of the outer wall.

3. The ostomy appliance of claim 1, wherein the first part and the second part of the outer comfort layer are joined to each other at a first end and at a second end of the overlap region.

4. The ostomy appliance as claimed in claim 3, wherein the first part and the second part are welded to each other at the first end and at the second end of the overlap region.

5. The ostomy appliance as claimed in claim 4, wherein a single weld is provided for joining in one operation the inner wall, the outer wall and the outer comfort layer, including the welding of the first part and the second part to each other at the first end and at the second end of the overlap region.

6. The ostomy appliance of claim 1, further comprising either an ostomy wafer that is located in register with the inlet of the inner wall, or a releasable coupling that is located in register with the inlet of the inner wall and that is configured for coupling with a body fitment component comprising an ostomy wafer.

7. An ostomy appliance comprising an inner wall and an outer wall of flexible sheet material joined together to define a cavity for containing a stomal output;
the inner wall comprising an inlet for receiving the stomal output into the cavity;
the inner wall and outer wall defining a central region, a first lateral wing region and a second lateral wing region;
a separation wall located between the inner wall and the outer wall within the cavity; and sealed together at an at least upper and side peripheral regions of the separation wall to at least the upper and side peripheral regions of the inner wall and to the outer wall to form a first chamber between the inner wall and separation wall and a second chamber between the separation wall and the outer wall, and the separation wall further comprising a separation filter for filtering gases and/or liquids into the second chamber from solid matter contained in the stomal output as contained in the first chamber; and
a gas vent with a gas filter provided in an upper portion of the outer wall and configured to allow the gases to exit the ostomy appliance,
wherein the outer wall comprises one or more pleats which are configured to partially or fully unfold as the cavity receives the stomal output to promote conformation of the inner wall against a body of an ostomate wearing the ostomy appliance;
wherein the separation filter comprises one or more pleats; and
wherein the separation filter is configured to prevent at least stomal solids from passing from the first chamber, through the separation wall, into the second chamber, and contacting the gas filter.

8. The ostomy appliance as claimed in claim 7, wherein the one or more pleats are configured to partially or fully unfold as the cavity receives the stomal output to promote displacement of the first lateral wing region and the second lateral wing region towards the body of the ostomate.

9. The ostomy appliance of claim 7, wherein the inner wall is free of pleats.

10. The ostomy appliance of claim 7, wherein the one or more pleats of the outer wall comprise two pleats which are arranged symmetrically about a vertical midline of the outer wall.

11. The ostomy appliance of claim 7, wherein the one or more pleats of the outer wall are orientated vertically when a lower apex is vertically downward relative to an upper apex of the ostomy appliance.

12. The ostomy appliance of claim 7, wherein the first lateral wing region and the second lateral wing region are foldable about a fold line that extends in a generally vertical direction when a lower apex is vertically downward relative to an upper apex of the ostomy appliance.

13. The ostomy appliance as claimed in claim 12, wherein at least one of the one or more pleats of the outer wall is aligned with each of the fold lines.

14. The ostomy appliance as claimed in claim 7, wherein the one or more pleats of the separation filter are aligned with the one or more pleats of the outer wall.

15. The ostomy appliance of claim 7, wherein a free edge of the inner wall and a free edge of the outer wall are joined by a weld line.

16. The ostomy appliance as claimed in claim 15, wherein an upper end and a lower end of each of the one or more pleats of the outer wall is traversed by the weld line.

17. The ostomy appliance of claim 7, further comprising an outer comfort layer overlying the outer wall, wherein the outer comfort layer is free of pleats.

18. The ostomy appliance of claim 7, further comprising either an ostomy wafer that is located in register with the inlet of the inner wall, or a releasable coupling that is located in register with the inlet of the inner wall and that is configured for coupling with a body fitment component comprising an ostomy wafer.

* * * * *